US007326536B2

(12) United States Patent
Glenn et al.

(10) Patent No.: US 7,326,536 B2
(45) Date of Patent: Feb. 5, 2008

(54) AGENTS FOR TREATMENT OF HCV AND METHODS OF USE

(75) Inventors: Jeffrey S. Glenn, Palo Alto, CA (US); Tina Marie Myers, Indianapolis, IN (US); John Irvin Glass, Germantown, MD (US)

(73) Assignees: Eli Lilly and Company, Indianapolis, IN (US); The Board of Trustees of the Leland Stanford Junior University, Palo Alto, CA (US)

( * ) Notice: Subject to any disclaimer, the term of this patent is extended or adjusted under 35 U.S.C. 154(b) by 165 days.

(21) Appl. No.: 10/481,261

(22) PCT Filed: May 3, 2002

(86) PCT No.: PCT/US02/13951

§ 371 (c)(1),
(2), (4) Date: Jul. 30, 2004

(87) PCT Pub. No.: WO02/089731

PCT Pub. Date: Nov. 14, 2002

(65) Prior Publication Data

US 2004/0265792 A1    Dec. 30, 2004

Related U.S. Application Data

(60) Provisional application No. 60/288,687, filed on May 3, 2001, provisional application No. 60/316,805, filed on Aug. 31, 2001.

(51) Int. Cl.
| | | |
|---|---|---|
| *C12Q 1/00* | (2006.01) | |
| *C12Q 1/66* | (2006.01) | |
| *C12Q 1/70* | (2006.01) | |
| *G01N 33/53* | (2006.01) | |
| *A61K 38/00* | (2006.01) | |
| *C07K 4/00* | (2006.01) | |
| *C07K 14/08* | (2006.01) | |

(52) U.S. Cl. .............................. 435/7.1; 435/4; 435/5; 435/7.2; 435/7.9; 435/8; 514/2; 530/300; 530/350

(58) Field of Classification Search .................... 435/4, 435/5, 7.1, 7.2, 7.9, 7.92; 514/1, 2; 530/300, 530/326, 327, 328, 350; 424/184.1, 185.1, 424/186.1, 189.1, 192.1, 206.1, 228.1
See application file for complete search history.

(56) References Cited

U.S. PATENT DOCUMENTS

| | | | | |
|---|---|---|---|---|
| 4,198,398 A | * | 4/1980 | Hudson et al. ................ | 514/17 |
| 5,380,668 A | * | 1/1995 | Herron ........................ | 436/510 |
| 5,591,440 A | * | 1/1997 | Carman et al. .......... | 424/227.1 |
| 5,747,239 A | * | 5/1998 | Wang et al. .................... | 435/5 |
| 6,287,761 B1 | * | 9/2001 | Deleys et al. ................... | 435/5 |
| 6,316,003 B1 | * | 11/2001 | Frankel et al. .......... | 424/196.11 |
| 6,986,892 B1 | * | 1/2006 | Coit et al. ............... | 424/228.1 |

OTHER PUBLICATIONS

Bressanelli et al., "Crystal structure of the RNA-dependent RNA polymerase of hepatitis C virus ," Proceedings of the National Academy of Sciences, USA, vol. 96 No. 23, pp. 13034-13039 (Nov. 1999).*
Choo et al., "Genetic Organization and Diversity of the Hepatitis C Virus ," Proceedings of the National Academy of Sciences, USA, vol. 88 No. 6, pp. 2451-2455 (Mar. 1991).*
GenPept BAA09071, "polyprotein [Hepatitis C virus]," NCBI printout, (Feb. 1999).*
Kim et al., "Subcellular localization of hepatitis C viral proteins in mammalian cells," ARchives of Virology, vol. 144 No. 2, pp. 329-343 (1999).*
Moradpour et al., "Membrane Association of the RNA-Dependent RNA Polymerase Is Essential for Hepatitis C Virus RNA Replication," Journal of Virology, vol. 78 No. 23, pp. 13278-13284 (Dec. 2004).*
Moradpour et al., "Function follows form: The structure of the N-terminal domain of HCV NS5A," Hepatology, vol. 42 No. 3, pp. 732-735 (Sep. 2005).*
Satoh et al., "Cleavage of Hepatitis C Virus Nonstructural Protein 5A by a Caspase-like Protease(s) in Mammalian Cells," Virology, vol. 270 No. 2, pp. 476-487 (May 2000).*
Takamizawa et al., "Structure and organization of the hepatitis C virus genome isolated from human carriers," Journal of Virology, vol. 65 No. 3, pp. 1105-1113 (Mar. 1993).*
Wong et al., "Liver-derived CTL in hepatitis C virus infection: breadth and specificity of responses in a cohort of persons with chronic infection," Journal of Immunology, vol. 160 No. 3, pp. 1479-1488 (Feb. 1998).*
Bartenschlager et al., "Candidate targets for hepatitis C virus-specific antiviral therapy," Intervirology, vol. 40 No. 5-6, pp. 378-393 (Sep.-Dec. 1997).*
Brass et al., "An Amino-terminal Amphiphathic -Helix Mediates Membrane Association of the Hepatitis C Virus Nonstructural Protein 5A," Journal of Biological Chemistry, vol. 277 No. 10, pp. 8130-8139 (Mar. 2002).*
Huang et al., "Recent development of therapeutics for chronic HCV infection," Antiviral REsearch, in press, (2006).*

(Continued)

*Primary Examiner*—Zachariah Lucas
(74) *Attorney, Agent, or Firm*—Carol L. Francis; Paula A. Borden; Bozicevic, Field & Francis LLP

(57) ABSTRACT

An amphipathic helix at the approximate N-terminus of Hepatitis C virus (HCV) nonstructural proteins mediates the association of these proteins with cytoplasmic membranes in infected cells. This association is essential for replication. Thus, assessing the ability of compounds or protocols to disrupt the association of such helices with cytoplasmic membranes permits identification of compounds and protocols which are useful in the treatment of HCV infection. Also useful in the invention are mimics, or function-disrupting ligands, of an amphipathic helix of the nonstructural proteins described herein and antibodies and fragments thereof immunoreactive with said helix.

17 Claims, 8 Drawing Sheets

OTHER PUBLICATIONS

Elazar et al., "An N-terminal amphipathic helix in hepatitis C virus (HCV) NS4B mediates membrane association, correct localization of replication complex proteins, and HCV RNA replication," Journal of Virology, vol. 78 No. 20, pp. 11393-11400 (Oct. 2004).*

Segrest et al., "Amphipathic helix motif: Classes and properties," Proteins, vol. 8 No. 2, pp. 103-117 (1990).*

Bienz, K., et al., "Structural and functional characterization of the poliovirus replication complex", J. Virol. (1992) 66:2740-2747.

Bienz, K., et al., "Kinetics and location of poliovirus macromolecular synthesis in correlation to virus-induced cytopathology", J. Virol. (1980) 100:390-399.

Brass, V. et al., "An amino-terminal amphipathic α-helix mediates membrane association of the hepatitis C virus nonstructural protein 5a", The journal of biological chemistry (2002) vol. 277, No. 10, pp. 8130-8139.

Chu, P.W. et al., "Molecular and ultrastructural analysis of heavy membrane fractions associated with the replication of kunjin virus RNA", Arch. Virol (1992) 125:177-191.

Enomoto, H., et al., "Mutations in the nonstructural protein 5a gene and response to interferon in patients with chronic hepatitis c virus 1b infection", N. Engl. J. Med. (1996) 334:77-81.

Froshauer, S., et al., "Alphavirus RNA replicase Is Located on the cytoplasmic surface of endosomes and lysosomes", J. Cell. Biol. (1988) 107:2075-2086.

Gale, M.J.J. et al., "Evidence that hepatitis c virus resistance to interferon is mediated through repression of the PKR protein kinase by the nonstructural 5a protein", Virol. (1997)290:217-227.

Hijikata, M., et al., "Proteolytic processing and membrane association of putative nonstructural proteins of hepatitis c virus", Proc. Natl. Acad. Sci. USA(1993)90:10773-10777.

Kusov, Y. Y., et al., "Membrane association and RNA binding of recombinant hepatitis a virus protein 2C", Arch. Virol. (1998) 143:931-944.

Kato, N., et al., "Hepatitis c virus nonstructural region 5a protein is a potent transcriptional activator", J. Virol (1997) 71:8856-8859.

Lazarus, L.H., et al., "Association of foot-and-mouth disease virus replicase with RNA template and cytoplasmic membranes", J Gen. Virol. (1974) 23:213-218.

Majumder, M., et al., "Hepatitis c virus NS5A physically associates with p53 and regulates p21/waf1 gene expression in a p53-dependent manner", J. Virol. (2001) 75:1401-1407.

Moradpour, D., et al., "Continuous human cell lines inducibly expressing hepatitis c virus structural and nonstructural proteins", Hepatol.(1998)28:192-201.

Paul, A.V., et al. "Studies of a putative amphipathic helix in the n-terminus of poliovirus Protein 2c", Virol. (1994) 199:188-199.

Rice, C.M., "Flaviviridae: the viruses and their replication", Fields Virology, Fields, B.N., et al., Ed. (1996) Lippincott-Raven Publications: Philadelphia, PA pp. 931-959 (Flaviviridae).

Schlegel, A., "Cellular origin and ultrastructure of membranes induced during poliovirus infection", J. Virol. (1996) 70:6576-6588.

Selby, M.J. et al. "Expression, identification and subcellular localization of the proteins encoded by the hepatitis C viral genome", J. Gen. Virol. (1993) 74:1103-1113.

Schmidt-Mende, et al., "Determinants for membrane association of the hepatitis c virus RNA-dependent RNA polymerase", The journal of biological chemistry, (1999) vol. 276, No. 47, pp. 44052-44063.

Tu, H. et al., "Hepatitis c virus RNA polymerase and NS5A complex with a snare-like protein", Virol. (1999) 263:30-41.

Tereina, N.L. et al., "Poliovirus 2c protein determinants of membrane binding and rearrangements in mammalian cells", J. Virol. (1997) 71:8962-8972.

Tanimoto, A., et al., "The amino terminal deletion mutants of hepatitis c virus constructural protein NS5A function as transcriptional activators in yeast", Biochem. Biophys. Res. Commun. (1997) 236:360-364.

Van Kuppeveld, F. et al., "Coxsackievirus protein 2b modifies endoplasmic reticulum membrane and plasma membrane permeability and facilitates virus release", The EMBO journal, (1997) vol. 16, No. 12, pp. 3519-3532.

* cited by examiner

| | | | |
|---|---|---|---|
| 1a | NS4B | 7-34 | IEQGMMLAEQFKQKALGLLQTASRHAEV |
| 1a | NS5A | 5-26 | LRDIWDWICEVLSDFKTWLKA |
| 1a | NS5B | 65-87 | QDVLKEVKAAASKVKANLLSVEE |
| 1a | NS5B | 107-125 | DVRCHARKAVAHINSVWKD |
| 1b | NS5A | 4-27 | WLRDVWDWICTVLTDFKTWLQSKL |
| 2a | NS5A | 4-27 | WLRDVWDWVCTILTDFKNWLTSKL |
| 2b | NS5A | 4-27 | WLRDIWEWVLSILTDFKNWLSAKL |
| 3a-K | NS5A | 4-27 | WLRIIWDWVCSVVSDFKTWLSAKI |
| 3a-NZL | NS5A | 4-27 | WLRTIWDWVCSVLADFKAWLSAKI |
| 3b | NS5A | 4-27 | WLHDIWDWVCIVLSDFKTWLSAKI |
| 4a | NS5A | 4-27 | WLWDVWDWVLHVLSDFKTCLKAKF |
| 10a | NS5A | 4-27 | WLYDIVNWVCTVLADFKLWLGAKI |
| 11a | NS5A | 4-27 | WLRDIWDWVCTVLSDFRVWLKSKL |

FIGURE 1

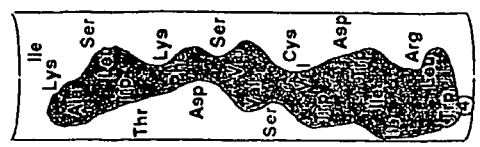
FIGURE 2E
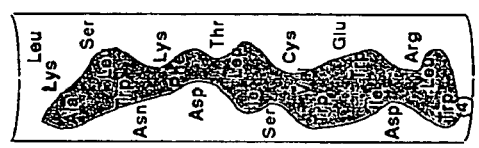
FIGURE 2D
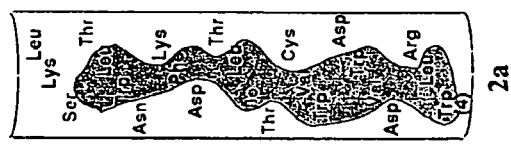
FIGURE 2C
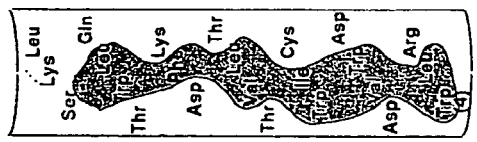
FIGURE 2B
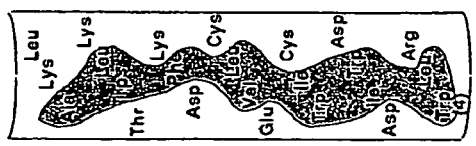
FIGURE 2A
FIGURE 2J
FIGURE 2I
FIGURE 2H
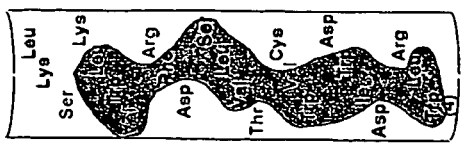
FIGURE 2G
FIGURE 2F
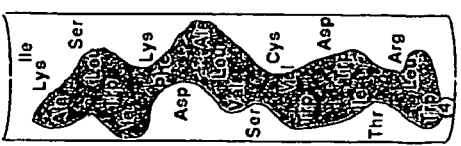
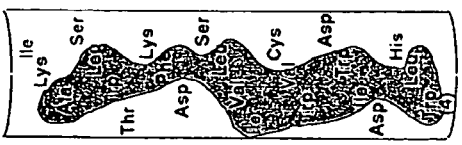
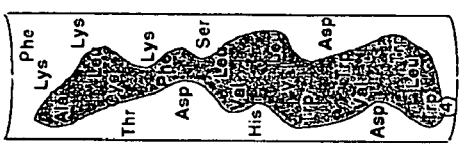

5ANHGFP

5AGFP

GFP

NS5A (448)

GFP (236)

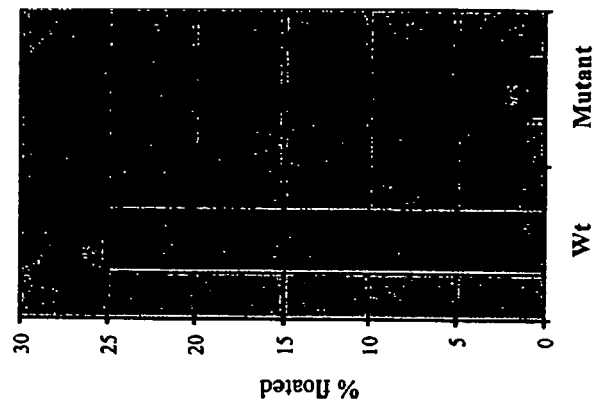
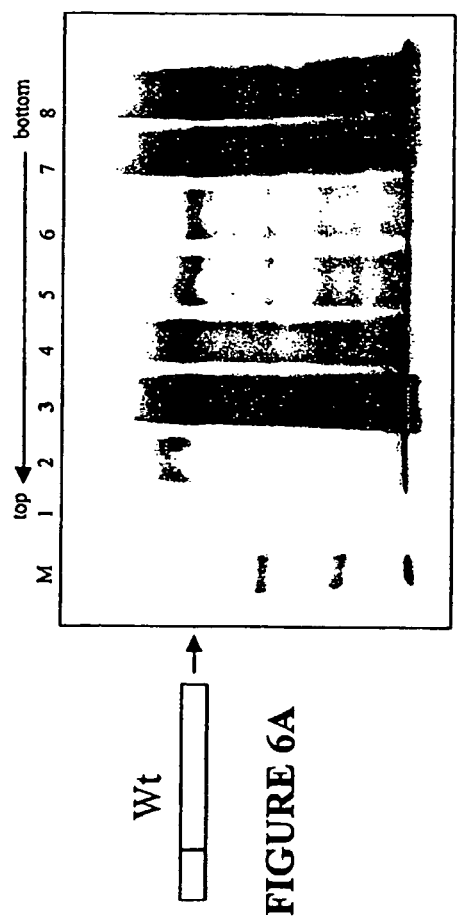
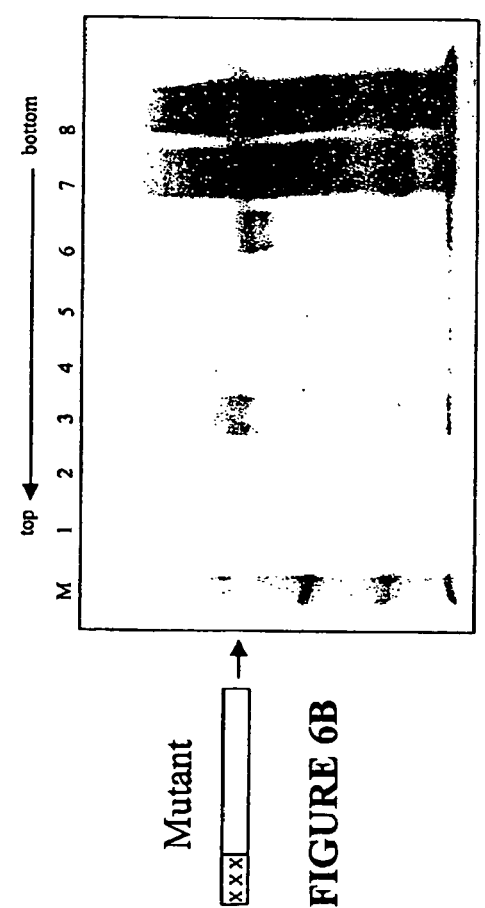
FIGURE 6A
FIGURE 6B
FIGURE 6C

SEQUENCE LISTING

<160> NUMBER OF SEQ ID NOS: 470

<210> SEQ ID NO 1
<211> LENGTH: 28
<212> TYPE: PRT
<213> ORGANISM: Hepatitis C virus

<400> SEQUENCE: 1

Ile Glu Gln Gly Met Met Leu Ala Glu Gln Phe Lys Gln Lys Ala Leu
1               5                   10                  15

Gly Leu Leu Gln Thr Ala Ser Arg His Ala Glu Val
            20                  25

<210> SEQ ID NO 2
<211> LENGTH: 21
<212> TYPE: PRT
<213> ORGANISM: Hepatitis C virus

<400> SEQUENCE: 2

Leu Arg Asp Ile Trp Asp Trp Ile Cys Glu Val Leu Ser Asp Phe Lys
1               5                   10                  15

Thr Trp Leu Lys Ala
            20

<210> SEQ ID NO 3
<211> LENGTH: 23
<212> TYPE: PRT
<213> ORGANISM: Hepatitis C virus

<400> SEQUENCE: 3

Gln Asp Val Leu Lys Glu Val Lys Ala Ala Ser Lys Val Lys Ala
1               5                   10                  15

Asn Leu Leu Ser Val Glu Glu
            20

<210> SEQ ID NO 4
<211> LENGTH: 19
<212> TYPE: PRT
<213> ORGANISM: Hepatitis C virus

<400> SEQUENCE: 4

Asp Val Arg Cys His Ala Arg Lys Ala Val Ala His Ile Asn Ser Val
1               5                   10                  15

Trp Lys Asp

<210> SEQ ID NO 5
<211> LENGTH: 24
<212> TYPE: PRT
<213> ORGANISM: Hepatitis C virus

<400> SEQUENCE: 5

Trp Leu Arg Asp Val Trp Asp Trp Ile Cys Thr Val Leu Thr Asp Phe
1               5                   10                  15

Lys Thr Trp Leu Gln Ser Lys Leu
            20

<210> SEQ ID NO 6
<211> LENGTH: 24
<212> TYPE: PRT
<213> ORGANISM: Hepatitis C virus -continued

```
<400> SEQUENCE: 6

Trp Leu Arg Asp Val Trp Asp Trp Val Cys Thr Ile Leu Thr Asp Phe
1               5                   10                  15

Lys Asn Trp Leu Thr Ser Lys Leu
            20

<210> SEQ ID NO 7
<211> LENGTH: 24
<212> TYPE: PRT
<213> ORGANISM: Hepatitis C virus

<400> SEQUENCE: 7

Trp Leu Arg Asp Ile Trp Glu Trp Val Leu Ser Ile Leu Thr Asp Phe
1               5                   10                  15

Lys Asn Trp Leu Ser Ala Lys Leu
            20

<210> SEQ ID NO 8
<211> LENGTH: 24
<212> TYPE: PRT
<213> ORGANISM: Hepatitis C virus

<400> SEQUENCE: 8

Trp Leu Arg Ile Ile Trp Asp Trp Val Cys Ser Val Val Ser Asp Phe
1               5                   10                  15

Lys Thr Trp Leu Ser Ala Lys Ile
            20

<210> SEQ ID NO 9
<211> LENGTH: 24
<212> TYPE: PRT
<213> ORGANISM: Hepatitis C virus

<400> SEQUENCE: 9

Trp Leu Arg Thr Ile Trp Asp Trp Val Cys Ser Val Leu Ala Asp Phe
1               5                   10                  15

Lys Ala Trp Leu Ser Ala Lys Ile
            20

<210> SEQ ID NO 10
<211> LENGTH: 24
<212> TYPE: PRT
<213> ORGANISM: Hepatitis C virus

<400> SEQUENCE: 10

Trp Leu His Asp Ile Trp Asp Trp Val Cys Ile Val Leu Ser Asp Phe
1               5                   10                  15

Lys Thr Trp Leu Ser Ala Lys Ile
            20

<210> SEQ ID NO 11
<211> LENGTH: 24
<212> TYPE: PRT
<213> ORGANISM: Hepatitis C virus

<400> SEQUENCE: 11

Trp Leu Trp Asp Val Trp Asp Trp Val Leu His Val Leu Ser Asp Phe
1               5                   10                  15

Lys Thr Cys Leu Lys Ala Lys Phe
            20
```

```
<210> SEQ ID NO 12
<211> LENGTH: 24
<212> TYPE: PRT
<213> ORGANISM: Hepatitis C virus

<400> SEQUENCE: 12

Trp Leu Tyr Asp Ile Val Asn Trp Val Cys Thr Val Leu Ala Asp Phe
1               5                   10                  15

Lys Leu Trp Leu Gly Ala Lys Ile
            20

<210> SEQ ID NO 13
<211> LENGTH: 24
<212> TYPE: PRT
<213> ORGANISM: Hepatitis C virus

<400> SEQUENCE: 13

Trp Leu Arg Asp Ile Trp Asp Trp Val Cys Thr Val Leu Ser Asp Phe
1               5                   10                  15

Arg Val Trp Leu Lys Ser Lys Leu
            20

<210> SEQ ID NO 14
<211> LENGTH: 27
<212> TYPE: PRT
<213> ORGANISM: Hepatitis C virus

<400> SEQUENCE: 14

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu
            20                  25

<210> SEQ ID NO 15
<211> LENGTH: 26
<212> TYPE: PRT
<213> ORGANISM: Artificial sequence
<220> FEATURE:
<223> OTHER INFORMATION: Mutated version of non-structural protein NS5A

<400> SEQUENCE: 15

Ser Gly Ser Trp Leu Arg Asp Asp Trp Asp Trp Glu Cys Glu Val Leu
1               5                   10                  15

Ser Asp Asp Lys Thr Trp Leu Lys Ala Lys
            20                  25

<210> SEQ ID NO 16
<211> LENGTH: 27
<212> TYPE: PRT
<213> ORGANISM: Artificial sequence
<220> FEATURE:
<223> OTHER INFORMATION: Mutated version of non-structural protein NS5A

<400> SEQUENCE: 16

Ser Gly Ser Trp Leu Arg Asp Asp Trp Asp Trp Glu Cys Thr Val Leu
1               5                   10                  15

Thr Asp Asp Lys Thr Trp Leu Gln Ser Lys Leu
            20                  25

<210> SEQ ID NO 17
<211> LENGTH: 84
<212> TYPE: RNA
<213> ORGANISM: Hepatitis C virus
```

```
<400> SEQUENCE: 17 ucaucgagc aagggaugau gcucgcugag caguucaagc agaaggcccu cggccuccug    60
cagaccgcgu cccgccaagc agag                                          84

<210> SEQ ID NO 18
<211> LENGTH: 28
<212> TYPE: PRT
<213> ORGANISM: Hepatitis C virus

<400> SEQUENCE: 18

Tyr Ile Glu Gln Gly Met Met Leu Ala Glu Gln Phe Lys Gln Lys Ala
1               5                   10                  15

Leu Gly Leu Leu Gln Thr Ala Ser Arg Gln Ala Glu
            20                  25

<210> SEQ ID NO 19
<211> LENGTH: 84
<212> TYPE: DNA
<213> ORGANISM: Hepatitis C virus

<400> SEQUENCE: 19
ctctgcttgg cgggacgcgg tctgcaggag gccgagggcc ttctgcttga actgctcagc    60
gagcatcatc ccttgctcga tgta                                          84

<210> SEQ ID NO 20
<211> LENGTH: 28
<212> TYPE: PRT
<213> ORGANISM: Hepatitis C virus

<400> SEQUENCE: 20

Leu Cys Leu Ala Gly Arg Gly Leu Gln Glu Ala Glu Gly Leu Leu Leu
1               5                   10                  15

Glu Leu Leu Ser Glu His His Pro Leu Leu Asp Val
            20                  25

<210> SEQ ID NO 21
<211> LENGTH: 6
<212> TYPE: PRT
<213> ORGANISM: Hepatitis C virus

<400> SEQUENCE: 21

Leu Gln Glu Ala Glu Gly
1               5

<210> SEQ ID NO 22
<211> LENGTH: 6
<212> TYPE: PRT
<213> ORGANISM: Hepatitis C virus

<400> SEQUENCE: 22

Cys Leu Ala Gly Arg Gly
1               5

<210> SEQ ID NO 23
<211> LENGTH: 6
<212> TYPE: PRT
<213> ORGANISM: Hepatitis C virus

<400> SEQUENCE: 23

Leu Glu Leu Leu Ser Glu
1               5
```

```
<210> SEQ ID NO 24
<211> LENGTH: 6
<212> TYPE: PRT
<213> ORGANISM: Hepatitis C virus

<400> SEQUENCE: 24

Gly Leu Gln Glu Ala Glu
1               5

<210> SEQ ID NO 25
<211> LENGTH: 6
<212> TYPE: PRT
<213> ORGANISM: Hepatitis C virus

<400> SEQUENCE: 25

Leu Leu Glu Leu Leu Ser
1               5

<210> SEQ ID NO 26
<211> LENGTH: 6
<212> TYPE: PRT
<213> ORGANISM: Hepatitis C virus

<400> SEQUENCE: 26

Gln Glu Ala Glu Gly Leu
1               5

<210> SEQ ID NO 27
<211> LENGTH: 6
<212> TYPE: PRT
<213> ORGANISM: Hepatitis C virus

<400> SEQUENCE: 27

Arg Gly Leu Gln Glu Ala
1               5

<210> SEQ ID NO 28
<211> LENGTH: 6
<212> TYPE: PRT
<213> ORGANISM: Hepatitis C virus

<400> SEQUENCE: 28

Leu Ala Gly Arg Gly Leu
1               5

<210> SEQ ID NO 29
<211> LENGTH: 6
<212> TYPE: PRT
<213> ORGANISM: Hepatitis C virus

<400> SEQUENCE: 29

Gly Arg Gly Leu Gln Glu
1               5

<210> SEQ ID NO 30
<211> LENGTH: 6
<212> TYPE: PRT
<213> ORGANISM: Hepatitis C virus

<400> SEQUENCE: 30

Glu Leu Leu Ser Glu His
1               5

<210> SEQ ID NO 31
```

```
<211> LENGTH: 6
<212> TYPE: PRT
<213> ORGANISM: Hepatitis C virus

<400> SEQUENCE: 31

Leu Leu Leu Glu Leu Leu
1               5

<210> SEQ ID NO 32
<211> LENGTH: 6
<212> TYPE: PRT
<213> ORGANISM: Hepatitis C virus

<400> SEQUENCE: 32

Leu Cys Leu Ala Gly Arg
1               5

<210> SEQ ID NO 33
<211> LENGTH: 6
<212> TYPE: PRT
<213> ORGANISM: Hepatitis C virus

<400> SEQUENCE: 33

His Pro Leu Leu Asp Val
1               5

<210> SEQ ID NO 34
<211> LENGTH: 6
<212> TYPE: PRT
<213> ORGANISM: Hepatitis C virus

<400> SEQUENCE: 34

Ala Glu Gly Leu Leu Leu
1               5

<210> SEQ ID NO 35
<211> LENGTH: 6
<212> TYPE: PRT
<213> ORGANISM: Hepatitis C virus

<400> SEQUENCE: 35

Ala Gly Arg Gly Leu Gln
1               5

<210> SEQ ID NO 36
<211> LENGTH: 6
<212> TYPE: PRT
<213> ORGANISM: Hepatitis C virus

<400> SEQUENCE: 36

Glu Ala Glu Gly Leu Leu
1               5

<210> SEQ ID NO 37
<211> LENGTH: 6
<212> TYPE: PRT
<213> ORGANISM: Hepatitis C virus

<400> SEQUENCE: 37

Leu Ser Glu His His Pro
1               5

<210> SEQ ID NO 38
<211> LENGTH: 6
<212> TYPE: PRT
```

```
<213> ORGANISM: Hepatitis C virus

<400> SEQUENCE: 38

His His Pro Leu Leu Asp
1               5

<210> SEQ ID NO 39
<211> LENGTH: 6
<212> TYPE: PRT
<213> ORGANISM: Hepatitis C virus

<400> SEQUENCE: 39

Glu Gly Leu Leu Leu Glu
1               5

<210> SEQ ID NO 40
<211> LENGTH: 6
<212> TYPE: PRT
<213> ORGANISM: Hepatitis C virus

<400> SEQUENCE: 40

Ser Glu His His Pro Leu
1               5

<210> SEQ ID NO 41
<211> LENGTH: 6
<212> TYPE: PRT
<213> ORGANISM: Hepatitis C virus

<400> SEQUENCE: 41

Leu Leu Ser Glu His His
1               5

<210> SEQ ID NO 42
<211> LENGTH: 6
<212> TYPE: PRT
<213> ORGANISM: Hepatitis C virus

<400> SEQUENCE: 42

Glu His His Pro Leu Leu
1               5

<210> SEQ ID NO 43
<211> LENGTH: 6
<212> TYPE: PRT
<213> ORGANISM: Hepatitis C virus

<400> SEQUENCE: 43

Gly Leu Leu Leu Glu Leu
1               5

<210> SEQ ID NO 44
<211> LENGTH: 7
<212> TYPE: PRT
<213> ORGANISM: Hepatitis C virus

<400> SEQUENCE: 44

Leu Glu Leu Leu Ser Glu His
1               5

<210> SEQ ID NO 45
<211> LENGTH: 7
<212> TYPE: PRT
<213> ORGANISM: Hepatitis C virus
```

```
<400> SEQUENCE: 45

Glu Leu Leu Ser Glu His His
1               5

<210> SEQ ID NO 46
<211> LENGTH: 7
<212> TYPE: PRT
<213> ORGANISM: Hepatitis C virus

<400> SEQUENCE: 46

Leu Leu Glu Leu Leu Ser Glu
1               5

<210> SEQ ID NO 47
<211> LENGTH: 7
<212> TYPE: PRT
<213> ORGANISM: Hepatitis C virus

<400> SEQUENCE: 47

Leu Leu Ser Glu His His Pro
1               5

<210> SEQ ID NO 48
<211> LENGTH: 7
<212> TYPE: PRT
<213> ORGANISM: Hepatitis C virus

<400> SEQUENCE: 48

His His Pro Leu Leu Asp Val
1               5

<210> SEQ ID NO 49
<211> LENGTH: 7
<212> TYPE: PRT
<213> ORGANISM: Hepatitis C virus

<400> SEQUENCE: 49

Gly Leu Leu Leu Glu Leu Leu
1               5

<210> SEQ ID NO 50
<211> LENGTH: 7
<212> TYPE: PRT
<213> ORGANISM: Hepatitis C virus

<400> SEQUENCE: 50

Leu Ala Gly Arg Gly Leu Gln
1               5

<210> SEQ ID NO 51
<211> LENGTH: 7
<212> TYPE: PRT
<213> ORGANISM: Hepatitis C virus

<400> SEQUENCE: 51

Leu Ser Glu His His Pro Leu
1               5

<210> SEQ ID NO 52
<211> LENGTH: 7
<212> TYPE: PRT
<213> ORGANISM: Hepatitis C virus

<400> SEQUENCE: 52
```

```
Leu Cys Leu Ala Gly Arg Gly
1               5

<210> SEQ ID NO 53
<211> LENGTH: 7
<212> TYPE: PRT
<213> ORGANISM: Hepatitis C virus

<400> SEQUENCE: 53

Leu Gln Glu Ala Glu Gly Leu
1               5

<210> SEQ ID NO 54
<211> LENGTH: 7
<212> TYPE: PRT
<213> ORGANISM: Hepatitis C virus

<400> SEQUENCE: 54

Ala Gly Arg Gly Leu Gln Glu
1               5

<210> SEQ ID NO 55
<211> LENGTH: 7
<212> TYPE: PRT
<213> ORGANISM: Hepatitis C virus

<400> SEQUENCE: 55

Ala Glu Gly Leu Leu Leu Glu
1               5

<210> SEQ ID NO 56
<211> LENGTH: 7
<212> TYPE: PRT
<213> ORGANISM: Hepatitis C virus

<400> SEQUENCE: 56

Gly Arg Gly Leu Gln Glu Ala
1               5

<210> SEQ ID NO 57
<211> LENGTH: 7
<212> TYPE: PRT
<213> ORGANISM: Hepatitis C virus

<400> SEQUENCE: 57

Arg Gly Leu Gln Glu Ala Glu
1               5

<210> SEQ ID NO 58
<211> LENGTH: 7
<212> TYPE: PRT
<213> ORGANISM: Hepatitis C virus

<400> SEQUENCE: 58

Gln Glu Ala Glu Gly Leu Leu
1               5

<210> SEQ ID NO 59
<211> LENGTH: 7
<212> TYPE: PRT
<213> ORGANISM: Hepatitis C virus

<400> SEQUENCE: 59

Ser Glu His His Pro Leu Leu
1               5
```

<210> SEQ ID NO 60
<211> LENGTH: 7
<212> TYPE: PRT
<213> ORGANISM: Hepatitis C virus

<400> SEQUENCE: 60

Glu His His Pro Leu Leu Asp
1               5

<210> SEQ ID NO 61
<211> LENGTH: 7
<212> TYPE: PRT
<213> ORGANISM: Hepatitis C virus

<400> SEQUENCE: 61

Gly Leu Gln Glu Ala Glu Gly
1               5

<210> SEQ ID NO 62
<211> LENGTH: 7
<212> TYPE: PRT
<213> ORGANISM: Hepatitis C virus

<400> SEQUENCE: 62

Glu Gly Leu Leu Leu Glu Leu
1               5

<210> SEQ ID NO 63
<211> LENGTH: 7
<212> TYPE: PRT
<213> ORGANISM: Hepatitis C virus

<400> SEQUENCE: 63

Leu Leu Leu Glu Leu Leu Ser
1               5

<210> SEQ ID NO 64
<211> LENGTH: 7
<212> TYPE: PRT
<213> ORGANISM: Hepatitis C virus

<400> SEQUENCE: 64

Glu Ala Glu Gly Leu Leu Leu
1               5

<210> SEQ ID NO 65
<211> LENGTH: 7
<212> TYPE: PRT
<213> ORGANISM: Hepatitis C virus

<400> SEQUENCE: 65

Cys Leu Ala Gly Arg Gly Leu
1               5

<210> SEQ ID NO 66
<211> LENGTH: 8
<212> TYPE: PRT
<213> ORGANISM: Hepatitis C virus

<400> SEQUENCE: 66

Cys Leu Ala Gly Arg Gly Leu Gln
1               5

<210> SEQ ID NO 67
<211> LENGTH: 8
<212> TYPE: PRT
<213> ORGANISM: Hepatitis C virus

<400> SEQUENCE: 67

Gln Glu Ala Glu Gly Leu Leu Leu
1               5

<210> SEQ ID NO 68
<211> LENGTH: 8
<212> TYPE: PRT
<213> ORGANISM: Hepatitis C virus

<400> SEQUENCE: 68

Leu Ala Gly Arg Gly Leu Gln Glu
1               5

<210> SEQ ID NO 69
<211> LENGTH: 8
<212> TYPE: PRT
<213> ORGANISM: Hepatitis C virus

<400> SEQUENCE: 69

Leu Cys Leu Ala Gly Arg Gly Leu
1               5

<210> SEQ ID NO 70
<211> LENGTH: 8
<212> TYPE: PRT
<213> ORGANISM: Hepatitis C virus

<400> SEQUENCE: 70

Ala Gly Arg Gly Leu Gln Glu Ala
1               5

<210> SEQ ID NO 71
<211> LENGTH: 8
<212> TYPE: PRT
<213> ORGANISM: Hepatitis C virus

<400> SEQUENCE: 71

Leu Leu Leu Glu Leu Leu Ser Glu
1               5

<210> SEQ ID NO 72
<211> LENGTH: 8
<212> TYPE: PRT
<213> ORGANISM: Hepatitis C virus

<400> SEQUENCE: 72

Leu Glu Leu Leu Ser Glu His His
1               5

<210> SEQ ID NO 73
<211> LENGTH: 8
<212> TYPE: PRT
<213> ORGANISM: Hepatitis C virus

<400> SEQUENCE: 73

Ala Glu Gly Leu Leu Leu Glu Leu
1               5

<210> SEQ ID NO 74
<211> LENGTH: 8

-continued

<212> TYPE: PRT
<213> ORGANISM: Hepatitis C virus

<400> SEQUENCE: 74

Glu Gly Leu Leu Leu Glu Leu Leu
1               5

<210> SEQ ID NO 75
<211> LENGTH: 8
<212> TYPE: PRT
<213> ORGANISM: Hepatitis C virus

<400> SEQUENCE: 75

Leu Leu Ser Glu His His Pro Leu
1               5

<210> SEQ ID NO 76
<211> LENGTH: 8
<212> TYPE: PRT
<213> ORGANISM: Hepatitis C virus

<400> SEQUENCE: 76

Gly Arg Gly Leu Gln Glu Ala Glu
1               5

<210> SEQ ID NO 77
<211> LENGTH: 8
<212> TYPE: PRT
<213> ORGANISM: Hepatitis C virus

<400> SEQUENCE: 77

Glu Ala Glu Gly Leu Leu Leu Glu
1               5

<210> SEQ ID NO 78
<211> LENGTH: 8
<212> TYPE: PRT
<213> ORGANISM: Hepatitis C virus

<400> SEQUENCE: 78

Arg Gly Leu Gln Glu Ala Glu Gly
1               5

<210> SEQ ID NO 79
<211> LENGTH: 8
<212> TYPE: PRT
<213> ORGANISM: Hepatitis C virus

<400> SEQUENCE: 79

Leu Leu Glu Leu Leu Ser Glu His
1               5

<210> SEQ ID NO 80
<211> LENGTH: 8
<212> TYPE: PRT
<213> ORGANISM: Hepatitis C virus

<400> SEQUENCE: 80

Ser Glu His His Pro Leu Leu Asp
1               5

<210> SEQ ID NO 81
<211> LENGTH: 8
<212> TYPE: PRT
<213> ORGANISM: Hepatitis C virus

```
<400> SEQUENCE: 81

Leu Ser Glu His His Pro Leu Leu
1               5

<210> SEQ ID NO 82
<211> LENGTH: 8
<212> TYPE: PRT
<213> ORGANISM: Hepatitis C virus

<400> SEQUENCE: 82

Leu Gln Glu Ala Glu Gly Leu Leu
1               5

<210> SEQ ID NO 83
<211> LENGTH: 8
<212> TYPE: PRT
<213> ORGANISM: Hepatitis C virus

<400> SEQUENCE: 83

Glu Leu Leu Ser Glu His His Pro
1               5

<210> SEQ ID NO 84
<211> LENGTH: 8
<212> TYPE: PRT
<213> ORGANISM: Hepatitis C virus

<400> SEQUENCE: 84

Gly Leu Leu Leu Glu Leu Leu Ser
1               5

<210> SEQ ID NO 85
<211> LENGTH: 8
<212> TYPE: PRT
<213> ORGANISM: Hepatitis C virus

<400> SEQUENCE: 85

Glu His His Pro Leu Leu Asp Val
1               5

<210> SEQ ID NO 86
<211> LENGTH: 8
<212> TYPE: PRT
<213> ORGANISM: Hepatitis C virus

<400> SEQUENCE: 86

Gly Leu Gln Glu Ala Glu Gly Leu
1               5

<210> SEQ ID NO 87
<211> LENGTH: 9
<212> TYPE: PRT
<213> ORGANISM: Hepatitis C virus

<400> SEQUENCE: 87

Leu Leu Ser Glu His His Pro Leu Leu
1               5

<210> SEQ ID NO 88
<211> LENGTH: 9
<212> TYPE: PRT
<213> ORGANISM: Hepatitis C virus

<400> SEQUENCE: 88
```

```
Leu Glu Leu Leu Ser Glu His His Pro
1               5
```

<210> SEQ ID NO 89
<211> LENGTH: 9
<212> TYPE: PRT
<213> ORGANISM: Hepatitis C virus

<400> SEQUENCE: 89

```
Arg Gly Leu Gln Glu Ala Glu Gly Leu
1               5
```

<210> SEQ ID NO 90
<211> LENGTH: 9
<212> TYPE: PRT
<213> ORGANISM: Hepatitis C virus

<400> SEQUENCE: 90

```
Glu Leu Leu Ser Glu His His Pro Leu
1               5
```

<210> SEQ ID NO 91
<211> LENGTH: 9
<212> TYPE: PRT
<213> ORGANISM: Hepatitis C virus

<400> SEQUENCE: 91

```
Leu Cys Leu Ala Gly Arg Gly Leu Gln
1               5
```

<210> SEQ ID NO 92
<211> LENGTH: 9
<212> TYPE: PRT
<213> ORGANISM: Hepatitis C virus

<400> SEQUENCE: 92

```
Ala Gly Arg Gly Leu Gln Glu Ala Glu
1               5
```

<210> SEQ ID NO 93
<211> LENGTH: 9
<212> TYPE: PRT
<213> ORGANISM: Hepatitis C virus

<400> SEQUENCE: 93

```
Gly Leu Leu Leu Glu Leu Leu Ser Glu
1               5
```

<210> SEQ ID NO 94
<211> LENGTH: 9
<212> TYPE: PRT
<213> ORGANISM: Hepatitis C virus

<400> SEQUENCE: 94

```
Leu Ser Glu His His Pro Leu Leu Asp
1               5
```

<210> SEQ ID NO 95
<211> LENGTH: 9
<212> TYPE: PRT
<213> ORGANISM: Hepatitis C virus

<400> SEQUENCE: 95

```
Glu Gly Leu Leu Leu Glu Leu Leu Ser
```

```
<210> SEQ ID NO 96
<211> LENGTH: 9
<212> TYPE: PRT
<213> ORGANISM: Hepatitis C virus

<400> SEQUENCE: 96

Gly Leu Gln Glu Ala Glu Gly Leu Leu
1               5

<210> SEQ ID NO 97
<211> LENGTH: 9
<212> TYPE: PRT
<213> ORGANISM: Hepatitis C virus

<400> SEQUENCE: 97

Ala Glu Gly Leu Leu Glu Leu Leu
1               5

<210> SEQ ID NO 98
<211> LENGTH: 9
<212> TYPE: PRT
<213> ORGANISM: Hepatitis C virus

<400> SEQUENCE: 98

Gln Glu Ala Glu Gly Leu Leu Leu Glu
1               5

<210> SEQ ID NO 99
<211> LENGTH: 9
<212> TYPE: PRT
<213> ORGANISM: Hepatitis C virus

<400> SEQUENCE: 99

Ser Glu His His Pro Leu Leu Asp Val
1               5

<210> SEQ ID NO 100
<211> LENGTH: 9
<212> TYPE: PRT
<213> ORGANISM: Hepatitis C virus

<400> SEQUENCE: 100

Leu Leu Leu Glu Leu Leu Ser Glu His
1               5

<210> SEQ ID NO 101
<211> LENGTH: 9
<212> TYPE: PRT
<213> ORGANISM: Hepatitis C virus

<400> SEQUENCE: 101

Gly Arg Gly Leu Gln Glu Ala Glu Gly
1               5

<210> SEQ ID NO 102
<211> LENGTH: 9
<212> TYPE: PRT
<213> ORGANISM: Hepatitis C virus

<400> SEQUENCE: 102

Cys Leu Ala Gly Arg Gly Leu Gln Glu
1               5
```

```
<210> SEQ ID NO 103
<211> LENGTH: 9
<212> TYPE: PRT
<213> ORGANISM: Hepatitis C virus

<400> SEQUENCE: 103

Glu Ala Glu Gly Leu Leu Leu Glu Leu
1               5

<210> SEQ ID NO 104
<211> LENGTH: 9
<212> TYPE: PRT
<213> ORGANISM: Hepatitis C virus

<400> SEQUENCE: 104

Leu Ala Gly Arg Gly Leu Gln Glu Ala
1               5

<210> SEQ ID NO 105
<211> LENGTH: 9
<212> TYPE: PRT
<213> ORGANISM: Hepatitis C virus

<400> SEQUENCE: 105

Leu Leu Glu Leu Leu Ser Glu His His
1               5

<210> SEQ ID NO 106
<211> LENGTH: 9
<212> TYPE: PRT
<213> ORGANISM: Hepatitis C virus

<400> SEQUENCE: 106

Leu Gln Glu Ala Glu Gly Leu Leu Leu
1               5

<210> SEQ ID NO 107
<211> LENGTH: 10
<212> TYPE: PRT
<213> ORGANISM: Hepatitis C virus

<400> SEQUENCE: 107

Leu Ser Glu His His Pro Leu Leu Asp Val
1               5                   10

<210> SEQ ID NO 108
<211> LENGTH: 10
<212> TYPE: PRT
<213> ORGANISM: Hepatitis C virus

<400> SEQUENCE: 108

Leu Glu Leu Leu Ser Glu His His Pro Leu
1               5                   10

<210> SEQ ID NO 109
<211> LENGTH: 10
<212> TYPE: PRT
<213> ORGANISM: Hepatitis C virus

<400> SEQUENCE: 109

Arg Gly Leu Gln Glu Ala Glu Gly Leu Leu
1               5                   10

<210> SEQ ID NO 110
```

```
<211> LENGTH: 10
<212> TYPE: PRT
<213> ORGANISM: Hepatitis C virus

<400> SEQUENCE: 110

Leu Leu Ser Glu His His Pro Leu Leu Asp
1               5                   10

<210> SEQ ID NO 111
<211> LENGTH: 10
<212> TYPE: PRT
<213> ORGANISM: Hepatitis C virus

<400> SEQUENCE: 111

Ala Glu Gly Leu Leu Leu Glu Leu Leu Ser
1               5                   10

<210> SEQ ID NO 112
<211> LENGTH: 10
<212> TYPE: PRT
<213> ORGANISM: Hepatitis C virus

<400> SEQUENCE: 112

Gly Leu Gln Glu Ala Glu Gly Leu Leu Leu
1               5                   10

<210> SEQ ID NO 113
<211> LENGTH: 10
<212> TYPE: PRT
<213> ORGANISM: Hepatitis C virus

<400> SEQUENCE: 113

Glu Gly Leu Leu Leu Glu Leu Leu Ser Glu
1               5                   10

<210> SEQ ID NO 114
<211> LENGTH: 10
<212> TYPE: PRT
<213> ORGANISM: Hepatitis C virus

<400> SEQUENCE: 114

Leu Cys Leu Ala Gly Arg Gly Leu Gln Glu
1               5                   10

<210> SEQ ID NO 115
<211> LENGTH: 10
<212> TYPE: PRT
<213> ORGANISM: Hepatitis C virus

<400> SEQUENCE: 115

Leu Leu Leu Glu Leu Leu Ser Glu His His
1               5                   10

<210> SEQ ID NO 116
<211> LENGTH: 10
<212> TYPE: PRT
<213> ORGANISM: Hepatitis C virus

<400> SEQUENCE: 116

Glu Ala Glu Gly Leu Leu Leu Glu Leu Leu
1               5                   10

<210> SEQ ID NO 117
<211> LENGTH: 10
<212> TYPE: PRT
```

<210> SEQ ID NO 118
<211> LENGTH: 10
<212> TYPE: PRT
<213> ORGANISM: Hepatitis C virus

<400> SEQUENCE: 117

Gly Leu Leu Leu Glu Leu Leu Ser Glu His
1               5                   10

<210> SEQ ID NO 118
<211> LENGTH: 10
<212> TYPE: PRT
<213> ORGANISM: Hepatitis C virus

<400> SEQUENCE: 118

Glu Leu Leu Ser Glu His His Pro Leu Leu
1               5                   10

<210> SEQ ID NO 119
<211> LENGTH: 10
<212> TYPE: PRT
<213> ORGANISM: Hepatitis C virus

<400> SEQUENCE: 119

Gly Arg Gly Leu Gln Glu Ala Glu Gly Leu
1               5                   10

<210> SEQ ID NO 120
<211> LENGTH: 10
<212> TYPE: PRT
<213> ORGANISM: Hepatitis C virus

<400> SEQUENCE: 120

Leu Gln Glu Ala Glu Gly Leu Leu Leu Glu
1               5                   10

<210> SEQ ID NO 121
<211> LENGTH: 10
<212> TYPE: PRT
<213> ORGANISM: Hepatitis C virus

<400> SEQUENCE: 121

Leu Leu Glu Leu Leu Ser Glu His His Pro
1               5                   10

<210> SEQ ID NO 122
<211> LENGTH: 10
<212> TYPE: PRT
<213> ORGANISM: Hepatitis C virus

<400> SEQUENCE: 122

Cys Leu Ala Gly Arg Gly Leu Gln Glu Ala
1               5                   10

<210> SEQ ID NO 123
<211> LENGTH: 10
<212> TYPE: PRT
<213> ORGANISM: Hepatitis C virus

<400> SEQUENCE: 123

Gln Glu Ala Glu Gly Leu Leu Leu Glu Leu
1               5                   10

<210> SEQ ID NO 124
<211> LENGTH: 10
<212> TYPE: PRT
<213> ORGANISM: Hepatitis C virus

```
<400> SEQUENCE: 124

Ala Gly Arg Gly Leu Gln Glu Ala Glu Gly
1               5                   10

<210> SEQ ID NO 125
<211> LENGTH: 10
<212> TYPE: PRT
<213> ORGANISM: Hepatitis C virus

<400> SEQUENCE: 125

Leu Ala Gly Arg Gly Leu Gln Glu Ala Glu
1               5                   10

<210> SEQ ID NO 126
<211> LENGTH: 11
<212> TYPE: PRT
<213> ORGANISM: Hepatitis C virus

<400> SEQUENCE: 126

Leu Leu Glu Leu Leu Ser Glu His His Pro Leu
1               5                   10

<210> SEQ ID NO 127
<211> LENGTH: 11
<212> TYPE: PRT
<213> ORGANISM: Hepatitis C virus

<400> SEQUENCE: 127

Cys Leu Ala Gly Arg Gly Leu Gln Glu Ala Glu
1               5                   10

<210> SEQ ID NO 128
<211> LENGTH: 11
<212> TYPE: PRT
<213> ORGANISM: Hepatitis C virus

<400> SEQUENCE: 128

Arg Gly Leu Gln Glu Ala Glu Gly Leu Leu Leu
1               5                   10

<210> SEQ ID NO 129
<211> LENGTH: 11
<212> TYPE: PRT
<213> ORGANISM: Hepatitis C virus

<400> SEQUENCE: 129

Leu Ala Gly Arg Gly Leu Gln Glu Ala Glu Gly
1               5                   10

<210> SEQ ID NO 130
<211> LENGTH: 11
<212> TYPE: PRT
<213> ORGANISM: Hepatitis C virus

<400> SEQUENCE: 130

Leu Gln Glu Ala Glu Gly Leu Leu Leu Glu Leu
1               5                   10

<210> SEQ ID NO 131
<211> LENGTH: 11
<212> TYPE: PRT
<213> ORGANISM: Hepatitis C virus

<400> SEQUENCE: 131
```

```
Leu Leu Leu Glu Leu Leu Ser Glu His His Pro
1               5                   10
```

<210> SEQ ID NO 132
<211> LENGTH: 11
<212> TYPE: PRT
<213> ORGANISM: Hepatitis C virus

<400> SEQUENCE: 132

```
Glu Leu Leu Ser Glu His His Pro Leu Leu Asp
1               5                   10
```

<210> SEQ ID NO 133
<211> LENGTH: 11
<212> TYPE: PRT
<213> ORGANISM: Hepatitis C virus

<400> SEQUENCE: 133

```
Ala Gly Arg Gly Leu Gln Glu Ala Glu Gly Leu
1               5                   10
```

<210> SEQ ID NO 134
<211> LENGTH: 11
<212> TYPE: PRT
<213> ORGANISM: Hepatitis C virus

<400> SEQUENCE: 134

```
Leu Leu Ser Glu His His Pro Leu Leu Asp Val
1               5                   10
```

<210> SEQ ID NO 135
<211> LENGTH: 11
<212> TYPE: PRT
<213> ORGANISM: Hepatitis C virus

<400> SEQUENCE: 135

```
Leu Cys Leu Ala Gly Arg Gly Leu Gln Glu Ala
1               5                   10
```

<210> SEQ ID NO 136
<211> LENGTH: 11
<212> TYPE: PRT
<213> ORGANISM: Hepatitis C virus

<400> SEQUENCE: 136

```
Gly Leu Leu Leu Glu Leu Leu Ser Glu His His
1               5                   10
```

<210> SEQ ID NO 137
<211> LENGTH: 11
<212> TYPE: PRT
<213> ORGANISM: Hepatitis C virus

<400> SEQUENCE: 137

```
Leu Glu Leu Leu Ser Glu His His Pro Leu Leu
1               5                   10
```

<210> SEQ ID NO 138
<211> LENGTH: 11
<212> TYPE: PRT
<213> ORGANISM: Hepatitis C virus

<400> SEQUENCE: 138

```
Gln Glu Ala Glu Gly Leu Leu Leu Glu Leu Leu
1               5                   10
```

```
<210> SEQ ID NO 139
<211> LENGTH: 11
<212> TYPE: PRT
<213> ORGANISM: Hepatitis C virus

<400> SEQUENCE: 139

Glu Gly Leu Leu Leu Glu Leu Leu Ser Glu His
1               5                   10

<210> SEQ ID NO 140
<211> LENGTH: 11
<212> TYPE: PRT
<213> ORGANISM: Hepatitis C virus

<400> SEQUENCE: 140

Gly Arg Gly Leu Gln Glu Ala Glu Gly Leu Leu
1               5                   10

<210> SEQ ID NO 141
<211> LENGTH: 11
<212> TYPE: PRT
<213> ORGANISM: Hepatitis C virus

<400> SEQUENCE: 141

Ala Glu Gly Leu Leu Leu Glu Leu Leu Ser Glu
1               5                   10

<210> SEQ ID NO 142
<211> LENGTH: 11
<212> TYPE: PRT
<213> ORGANISM: Hepatitis C virus

<400> SEQUENCE: 142

Gly Leu Gln Glu Ala Glu Gly Leu Leu Leu Glu
1               5                   10

<210> SEQ ID NO 143
<211> LENGTH: 11
<212> TYPE: PRT
<213> ORGANISM: Hepatitis C virus

<400> SEQUENCE: 143

Glu Ala Glu Gly Leu Leu Leu Glu Leu Leu Ser
1               5                   10

<210> SEQ ID NO 144
<211> LENGTH: 12
<212> TYPE: PRT
<213> ORGANISM: Hepatitis C virus

<400> SEQUENCE: 144

Glu Gly Leu Leu Leu Glu Leu Leu Ser Glu His His
1               5                   10

<210> SEQ ID NO 145
<211> LENGTH: 12
<212> TYPE: PRT
<213> ORGANISM: Hepatitis C virus

<400> SEQUENCE: 145

Arg Gly Leu Gln Glu Ala Glu Gly Leu Leu Leu Glu
1               5                   10
```

-continued

```
<210> SEQ ID NO 146
<211> LENGTH: 12
<212> TYPE: PRT
<213> ORGANISM: Hepatitis C virus

<400> SEQUENCE: 146

Gly Leu Leu Leu Glu Leu Leu Ser Glu His His Pro
1               5                   10

<210> SEQ ID NO 147
<211> LENGTH: 12
<212> TYPE: PRT
<213> ORGANISM: Hepatitis C virus

<400> SEQUENCE: 147

Leu Gln Glu Ala Glu Gly Leu Leu Leu Glu Leu Leu
1               5                   10

<210> SEQ ID NO 148
<211> LENGTH: 12
<212> TYPE: PRT
<213> ORGANISM: Hepatitis C virus

<400> SEQUENCE: 148

Gly Leu Gln Glu Ala Glu Gly Leu Leu Leu Glu Leu
1               5                   10

<210> SEQ ID NO 149
<211> LENGTH: 12
<212> TYPE: PRT
<213> ORGANISM: Hepatitis C virus

<400> SEQUENCE: 149

Leu Ala Gly Arg Gly Leu Gln Glu Ala Glu Gly Leu
1               5                   10

<210> SEQ ID NO 150
<211> LENGTH: 12
<212> TYPE: PRT
<213> ORGANISM: Hepatitis C virus

<400> SEQUENCE: 150

Gly Arg Gly Leu Gln Glu Ala Glu Gly Leu Leu Leu
1               5                   10

<210> SEQ ID NO 151
<211> LENGTH: 12
<212> TYPE: PRT
<213> ORGANISM: Hepatitis C virus

<400> SEQUENCE: 151

Gln Glu Ala Glu Gly Leu Leu Leu Glu Leu Leu Ser
1               5                   10

<210> SEQ ID NO 152
<211> LENGTH: 12
<212> TYPE: PRT
<213> ORGANISM: Hepatitis C virus

<400> SEQUENCE: 152

Ala Glu Gly Leu Leu Leu Glu Leu Leu Ser Glu His
1               5                   10

<210> SEQ ID NO 153
<211> LENGTH: 12
```

```
<212> TYPE: PRT
<213> ORGANISM: Hepatitis C virus

<400> SEQUENCE: 153

Ala Gly Arg Gly Leu Gln Glu Ala Glu Gly Leu Leu
1               5                   10

<210> SEQ ID NO 154
<211> LENGTH: 12
<212> TYPE: PRT
<213> ORGANISM: Hepatitis C virus

<400> SEQUENCE: 154

Leu Glu Leu Leu Ser Glu His His Pro Leu Leu Asp
1               5                   10

<210> SEQ ID NO 155
<211> LENGTH: 12
<212> TYPE: PRT
<213> ORGANISM: Hepatitis C virus

<400> SEQUENCE: 155

Leu Cys Leu Ala Gly Arg Gly Leu Gln Glu Ala Glu
1               5                   10

<210> SEQ ID NO 156
<211> LENGTH: 12
<212> TYPE: PRT
<213> ORGANISM: Hepatitis C virus

<400> SEQUENCE: 156

Leu Leu Leu Glu Leu Leu Ser Glu His His Pro Leu
1               5                   10

<210> SEQ ID NO 157
<211> LENGTH: 12
<212> TYPE: PRT
<213> ORGANISM: Hepatitis C virus

<400> SEQUENCE: 157

Leu Leu Glu Leu Leu Ser Glu His His Pro Leu Leu
1               5                   10

<210> SEQ ID NO 158
<211> LENGTH: 12
<212> TYPE: PRT
<213> ORGANISM: Hepatitis C virus

<400> SEQUENCE: 158

Glu Leu Leu Ser Glu His His Pro Leu Leu Asp Val
1               5                   10

<210> SEQ ID NO 159
<211> LENGTH: 12
<212> TYPE: PRT
<213> ORGANISM: Hepatitis C virus

<400> SEQUENCE: 159

Glu Ala Glu Gly Leu Leu Leu Glu Leu Leu Ser Glu
1               5                   10

<210> SEQ ID NO 160
<211> LENGTH: 12
<212> TYPE: PRT
<213> ORGANISM: Hepatitis C virus
```

```
<400> SEQUENCE: 160

Cys Leu Ala Gly Arg Gly Leu Gln Glu Ala Glu Gly
1               5                   10

<210> SEQ ID NO 161
<211> LENGTH: 13
<212> TYPE: PRT
<213> ORGANISM: Hepatitis C virus

<400> SEQUENCE: 161

Cys Leu Ala Gly Arg Gly Leu Gln Glu Ala Glu Gly Leu
1               5                   10

<210> SEQ ID NO 162
<211> LENGTH: 13
<212> TYPE: PRT
<213> ORGANISM: Hepatitis C virus

<400> SEQUENCE: 162

Arg Gly Leu Gln Glu Ala Glu Gly Leu Leu Glu Leu
1               5                   10

<210> SEQ ID NO 163
<211> LENGTH: 13
<212> TYPE: PRT
<213> ORGANISM: Hepatitis C virus

<400> SEQUENCE: 163

Leu Leu Glu Leu Leu Ser Glu His His Pro Leu Leu Asp
1               5                   10

<210> SEQ ID NO 164
<211> LENGTH: 13
<212> TYPE: PRT
<213> ORGANISM: Hepatitis C virus

<400> SEQUENCE: 164

Gly Arg Gly Leu Gln Glu Ala Glu Gly Leu Leu Leu Glu
1               5                   10

<210> SEQ ID NO 165
<211> LENGTH: 13
<212> TYPE: PRT
<213> ORGANISM: Hepatitis C virus

<400> SEQUENCE: 165

Leu Cys Leu Ala Gly Arg Gly Leu Gln Glu Ala Glu Gly
1               5                   10

<210> SEQ ID NO 166
<211> LENGTH: 13
<212> TYPE: PRT
<213> ORGANISM: Hepatitis C virus

<400> SEQUENCE: 166

Leu Glu Leu Leu Ser Glu His His Pro Leu Leu Asp Val
1               5                   10

<210> SEQ ID NO 167
<211> LENGTH: 13
<212> TYPE: PRT
<213> ORGANISM: Hepatitis C virus

<400> SEQUENCE: 167
```

```
Glu Gly Leu Leu Leu Glu Leu Leu Ser Glu His His Pro
1               5                   10
```

<210> SEQ ID NO 168
<211> LENGTH: 13
<212> TYPE: PRT
<213> ORGANISM: Hepatitis C virus

<400> SEQUENCE: 168

```
Glu Ala Glu Gly Leu Leu Leu Glu Leu Leu Ser Glu His
1               5                   10
```

<210> SEQ ID NO 169
<211> LENGTH: 13
<212> TYPE: PRT
<213> ORGANISM: Hepatitis C virus

<400> SEQUENCE: 169

```
Gly Leu Gln Glu Ala Glu Gly Leu Leu Leu Glu Leu Leu
1               5                   10
```

<210> SEQ ID NO 170
<211> LENGTH: 13
<212> TYPE: PRT
<213> ORGANISM: Hepatitis C virus

<400> SEQUENCE: 170

```
Ala Gly Arg Gly Leu Gln Glu Ala Glu Gly Leu Leu Leu
1               5                   10
```

<210> SEQ ID NO 171
<211> LENGTH: 13
<212> TYPE: PRT
<213> ORGANISM: Hepatitis C virus

<400> SEQUENCE: 171

```
Ala Glu Gly Leu Leu Leu Glu Leu Leu Ser Glu His His
1               5                   10
```

<210> SEQ ID NO 172
<211> LENGTH: 13
<212> TYPE: PRT
<213> ORGANISM: Hepatitis C virus

<400> SEQUENCE: 172

```
Leu Ala Gly Arg Gly Leu Gln Glu Ala Glu Gly Leu Leu
1               5                   10
```

<210> SEQ ID NO 173
<211> LENGTH: 13
<212> TYPE: PRT
<213> ORGANISM: Hepatitis C virus

<400> SEQUENCE: 173

```
Gln Glu Ala Glu Gly Leu Leu Leu Glu Leu Leu Ser Glu
1               5                   10
```

<210> SEQ ID NO 174
<211> LENGTH: 13
<212> TYPE: PRT
<213> ORGANISM: Hepatitis C virus

<400> SEQUENCE: 174

Leu Leu Leu Glu Leu Leu Ser Glu His His Pro Leu Leu

```
<210> SEQ ID NO 175
<211> LENGTH: 13
<212> TYPE: PRT
<213> ORGANISM: Hepatitis C virus

<400> SEQUENCE: 175

Leu Gln Glu Ala Glu Gly Leu Leu Leu Glu Leu Leu Ser
1               5                   10

<210> SEQ ID NO 176
<211> LENGTH: 13
<212> TYPE: PRT
<213> ORGANISM: Hepatitis C virus

<400> SEQUENCE: 176

Gly Leu Leu Leu Glu Leu Leu Ser Glu His His Pro Leu
1               5                   10

<210> SEQ ID NO 177
<211> LENGTH: 14
<212> TYPE: PRT
<213> ORGANISM: Hepatitis C virus

<400> SEQUENCE: 177

Glu Ala Glu Gly Leu Leu Leu Glu Leu Leu Ser Glu His His
1               5                   10

<210> SEQ ID NO 178
<211> LENGTH: 14
<212> TYPE: PRT
<213> ORGANISM: Hepatitis C virus

<400> SEQUENCE: 178

Glu Gly Leu Leu Leu Glu Leu Leu Ser Glu His His Pro Leu
1               5                   10

<210> SEQ ID NO 179
<211> LENGTH: 14
<212> TYPE: PRT
<213> ORGANISM: Hepatitis C virus

<400> SEQUENCE: 179

Ala Gly Arg Gly Leu Gln Glu Ala Glu Gly Leu Leu Leu Glu
1               5                   10

<210> SEQ ID NO 180
<211> LENGTH: 14
<212> TYPE: PRT
<213> ORGANISM: Hepatitis C virus

<400> SEQUENCE: 180

Leu Cys Leu Ala Gly Arg Gly Leu Gln Glu Ala Glu Gly Leu
1               5                   10

<210> SEQ ID NO 181
<211> LENGTH: 14
<212> TYPE: PRT
<213> ORGANISM: Hepatitis C virus

<400> SEQUENCE: 181

Gly Leu Leu Leu Glu Leu Leu Ser Glu His His Pro Leu Leu
1               5                   10
```

<210> SEQ ID NO 182
<211> LENGTH: 14
<212> TYPE: PRT
<213> ORGANISM: Hepatitis C virus

<400> SEQUENCE: 182

Gln Glu Ala Glu Gly Leu Leu Leu Glu Leu Leu Ser Glu His
1               5                   10

<210> SEQ ID NO 183
<211> LENGTH: 14
<212> TYPE: PRT
<213> ORGANISM: Hepatitis C virus

<400> SEQUENCE: 183

Arg Gly Leu Gln Glu Ala Glu Gly Leu Leu Leu Glu Leu Leu
1               5                   10

<210> SEQ ID NO 184
<211> LENGTH: 14
<212> TYPE: PRT
<213> ORGANISM: Hepatitis C virus

<400> SEQUENCE: 184

Leu Leu Leu Glu Leu Leu Ser Glu His His Pro Leu Leu Asp
1               5                   10

<210> SEQ ID NO 185
<211> LENGTH: 14
<212> TYPE: PRT
<213> ORGANISM: Hepatitis C virus

<400> SEQUENCE: 185

Leu Gln Glu Ala Glu Gly Leu Leu Leu Glu Leu Leu Ser Glu
1               5                   10

<210> SEQ ID NO 186
<211> LENGTH: 14
<212> TYPE: PRT
<213> ORGANISM: Hepatitis C virus

<400> SEQUENCE: 186

Leu Leu Glu Leu Leu Ser Glu His His Pro Leu Leu Asp Val
1               5                   10

<210> SEQ ID NO 187
<211> LENGTH: 14
<212> TYPE: PRT
<213> ORGANISM: Hepatitis C virus

<400> SEQUENCE: 187

Gly Leu Gln Glu Ala Glu Gly Leu Leu Leu Glu Leu Leu Ser
1               5                   10

<210> SEQ ID NO 188
<211> LENGTH: 14
<212> TYPE: PRT
<213> ORGANISM: Hepatitis C virus

<400> SEQUENCE: 188

Gly Arg Gly Leu Gln Glu Ala Glu Gly Leu Leu Leu Glu Leu
1               5                   10

<210> SEQ ID NO 189

```
<211> LENGTH: 14
<212> TYPE: PRT
<213> ORGANISM: Hepatitis C virus

<400> SEQUENCE: 189

Ala Glu Gly Leu Leu Glu Leu Leu Ser Glu His His Pro
1               5                   10

<210> SEQ ID NO 190
<211> LENGTH: 14
<212> TYPE: PRT
<213> ORGANISM: Hepatitis C virus

<400> SEQUENCE: 190

Cys Leu Ala Gly Arg Gly Leu Gln Glu Ala Glu Gly Leu Leu
1               5                   10

<210> SEQ ID NO 191
<211> LENGTH: 14
<212> TYPE: PRT
<213> ORGANISM: Hepatitis C virus

<400> SEQUENCE: 191

Leu Ala Gly Arg Gly Leu Gln Glu Ala Glu Gly Leu Leu Leu
1               5                   10

<210> SEQ ID NO 192
<211> LENGTH: 15
<212> TYPE: PRT
<213> ORGANISM: Hepatitis C virus

<400> SEQUENCE: 192

Leu Leu Leu Glu Leu Leu Ser Glu His His Pro Leu Leu Asp Val
1               5                   10                  15

<210> SEQ ID NO 193
<211> LENGTH: 15
<212> TYPE: PRT
<213> ORGANISM: Hepatitis C virus

<400> SEQUENCE: 193

Ala Gly Arg Gly Leu Gln Glu Ala Glu Gly Leu Leu Leu Glu Leu
1               5                   10                  15

<210> SEQ ID NO 194
<211> LENGTH: 15
<212> TYPE: PRT
<213> ORGANISM: Hepatitis C virus

<400> SEQUENCE: 194

Ala Glu Gly Leu Leu Leu Glu Leu Leu Ser Glu His His Pro Leu
1               5                   10                  15

<210> SEQ ID NO 195
<211> LENGTH: 15
<212> TYPE: PRT
<213> ORGANISM: Hepatitis C virus

<400> SEQUENCE: 195

Gly Leu Leu Leu Glu Leu Leu Ser Glu His His Pro Leu Leu Asp
1               5                   10                  15

<210> SEQ ID NO 196
<211> LENGTH: 15
<212> TYPE: PRT
```

-continued

<213> ORGANISM: Hepatitis C virus

<400> SEQUENCE: 196

Leu Gln Glu Ala Glu Gly Leu Leu Glu Leu Leu Ser Glu His
1               5                   10                  15

<210> SEQ ID NO 197
<211> LENGTH: 15
<212> TYPE: PRT
<213> ORGANISM: Hepatitis C virus

<400> SEQUENCE: 197

Gly Leu Gln Glu Ala Glu Gly Leu Leu Glu Leu Leu Ser Glu
1               5                   10                  15

<210> SEQ ID NO 198
<211> LENGTH: 15
<212> TYPE: PRT
<213> ORGANISM: Hepatitis C virus

<400> SEQUENCE: 198

Leu Cys Leu Ala Gly Arg Gly Leu Gln Glu Ala Glu Gly Leu Leu
1               5                   10                  15

<210> SEQ ID NO 199
<211> LENGTH: 15
<212> TYPE: PRT
<213> ORGANISM: Hepatitis C virus

<400> SEQUENCE: 199

Glu Ala Glu Gly Leu Leu Glu Leu Leu Ser Glu His His Pro
1               5                   10                  15

<210> SEQ ID NO 200
<211> LENGTH: 15
<212> TYPE: PRT
<213> ORGANISM: Hepatitis C virus

<400> SEQUENCE: 200

Gly Arg Gly Leu Gln Glu Ala Glu Gly Leu Leu Leu Glu Leu Leu
1               5                   10                  15

<210> SEQ ID NO 201
<211> LENGTH: 15
<212> TYPE: PRT
<213> ORGANISM: Hepatitis C virus

<400> SEQUENCE: 201

Gln Glu Ala Glu Gly Leu Leu Leu Glu Leu Leu Ser Glu His His
1               5                   10                  15

<210> SEQ ID NO 202
<211> LENGTH: 15
<212> TYPE: PRT
<213> ORGANISM: Hepatitis C virus

<400> SEQUENCE: 202

Leu Ala Gly Arg Gly Leu Gln Glu Ala Glu Gly Leu Leu Leu Glu
1               5                   10                  15

<210> SEQ ID NO 203
<211> LENGTH: 15
<212> TYPE: PRT
<213> ORGANISM: Hepatitis C virus

```
<400> SEQUENCE: 203

Cys Leu Ala Gly Arg Gly Leu Gln Glu Ala Glu Gly Leu Leu Leu
1               5                   10                  15

<210> SEQ ID NO 204
<211> LENGTH: 15
<212> TYPE: PRT
<213> ORGANISM: Hepatitis C virus

<400> SEQUENCE: 204

Glu Gly Leu Leu Leu Glu Leu Leu Ser Glu His His Pro Leu Leu
1               5                   10                  15

<210> SEQ ID NO 205
<211> LENGTH: 15
<212> TYPE: PRT
<213> ORGANISM: Hepatitis C virus

<400> SEQUENCE: 205

Arg Gly Leu Gln Glu Ala Glu Gly Leu Leu Leu Glu Leu Leu Ser
1               5                   10                  15

<210> SEQ ID NO 206
<211> LENGTH: 16
<212> TYPE: PRT
<213> ORGANISM: Hepatitis C virus

<400> SEQUENCE: 206

Leu Ala Gly Arg Gly Leu Gln Glu Ala Glu Gly Leu Leu Leu Glu Leu
1               5                   10                  15

<210> SEQ ID NO 207
<211> LENGTH: 16
<212> TYPE: PRT
<213> ORGANISM: Hepatitis C virus

<400> SEQUENCE: 207

Gly Leu Leu Leu Glu Leu Leu Ser Glu His His Pro Leu Leu Asp Val
1               5                   10                  15

<210> SEQ ID NO 208
<211> LENGTH: 16
<212> TYPE: PRT
<213> ORGANISM: Hepatitis C virus

<400> SEQUENCE: 208

Gly Arg Gly Leu Gln Glu Ala Glu Gly Leu Leu Leu Glu Leu Leu Ser
1               5                   10                  15

<210> SEQ ID NO 209
<211> LENGTH: 16
<212> TYPE: PRT
<213> ORGANISM: Hepatitis C virus

<400> SEQUENCE: 209

Ala Gly Arg Gly Leu Gln Glu Ala Glu Gly Leu Leu Leu Glu Leu Leu
1               5                   10                  15

<210> SEQ ID NO 210
<211> LENGTH: 16
<212> TYPE: PRT
<213> ORGANISM: Hepatitis C virus

<400> SEQUENCE: 210
```

```
Gly Leu Gln Glu Ala Glu Gly Leu Leu Leu Glu Leu Leu Ser Glu His
1               5                   10                  15
```

<210> SEQ ID NO 211
<211> LENGTH: 16
<212> TYPE: PRT
<213> ORGANISM: Hepatitis C virus

<400> SEQUENCE: 211

```
Arg Gly Leu Gln Glu Ala Glu Gly Leu Leu Leu Glu Leu Leu Ser Glu
1               5                   10                  15
```

<210> SEQ ID NO 212
<211> LENGTH: 16
<212> TYPE: PRT
<213> ORGANISM: Hepatitis C virus

<400> SEQUENCE: 212

```
Leu Gln Glu Ala Glu Gly Leu Leu Leu Glu Leu Leu Ser Glu His His
1               5                   10                  15
```

<210> SEQ ID NO 213
<211> LENGTH: 16
<212> TYPE: PRT
<213> ORGANISM: Hepatitis C virus

<400> SEQUENCE: 213

```
Cys Leu Ala Gly Arg Gly Leu Gln Glu Ala Glu Gly Leu Leu Leu Glu
1               5                   10                  15
```

<210> SEQ ID NO 214
<211> LENGTH: 16
<212> TYPE: PRT
<213> ORGANISM: Hepatitis C virus

<400> SEQUENCE: 214

```
Gln Glu Ala Glu Gly Leu Leu Leu Glu Leu Leu Ser Glu His His Pro
1               5                   10                  15
```

<210> SEQ ID NO 215
<211> LENGTH: 16
<212> TYPE: PRT
<213> ORGANISM: Hepatitis C virus

<400> SEQUENCE: 215

```
Ala Glu Gly Leu Leu Leu Glu Leu Leu Ser Glu His His Pro Leu Leu
1               5                   10                  15
```

<210> SEQ ID NO 216
<211> LENGTH: 16
<212> TYPE: PRT
<213> ORGANISM: Hepatitis C virus

<400> SEQUENCE: 216

```
Glu Ala Glu Gly Leu Leu Leu Glu Leu Leu Ser Glu His His Pro Leu
1               5                   10                  15
```

<210> SEQ ID NO 217
<211> LENGTH: 16
<212> TYPE: PRT
<213> ORGANISM: Hepatitis C virus

<400> SEQUENCE: 217

```
Leu Cys Leu Ala Gly Arg Gly Leu Gln Glu Ala Glu Gly Leu Leu Leu
1               5                   10                  15
```

```
<210> SEQ ID NO 218
<211> LENGTH: 16
<212> TYPE: PRT
<213> ORGANISM: Hepatitis C virus

<400> SEQUENCE: 218

Glu Gly Leu Leu Leu Glu Leu Leu Ser Glu His His Pro Leu Leu Asp
1               5                   10                  15

<210> SEQ ID NO 219
<211> LENGTH: 17
<212> TYPE: PRT
<213> ORGANISM: Hepatitis C virus

<400> SEQUENCE: 219

Leu Cys Leu Ala Gly Arg Gly Leu Gln Glu Ala Glu Gly Leu Leu Leu
1               5                   10                  15

Glu

<210> SEQ ID NO 220
<211> LENGTH: 17
<212> TYPE: PRT
<213> ORGANISM: Hepatitis C virus

<400> SEQUENCE: 220

Gln Glu Ala Glu Gly Leu Leu Leu Glu Leu Leu Ser Glu His His Pro
1               5                   10                  15

Leu

<210> SEQ ID NO 221
<211> LENGTH: 17
<212> TYPE: PRT
<213> ORGANISM: Hepatitis C virus

<400> SEQUENCE: 221

Glu Ala Glu Gly Leu Leu Leu Glu Leu Leu Ser Glu His His Pro Leu
1               5                   10                  15

Leu

<210> SEQ ID NO 222
<211> LENGTH: 17
<212> TYPE: PRT
<213> ORGANISM: Hepatitis C virus

<400> SEQUENCE: 222

Arg Gly Leu Gln Glu Ala Glu Gly Leu Leu Leu Glu Leu Leu Ser Glu
1               5                   10                  15

His

<210> SEQ ID NO 223
<211> LENGTH: 17
<212> TYPE: PRT
<213> ORGANISM: Hepatitis C virus

<400> SEQUENCE: 223

Cys Leu Ala Gly Arg Gly Leu Gln Glu Ala Glu Gly Leu Leu Leu Glu
1               5                   10                  15

Leu

<210> SEQ ID NO 224
```

```
<211> LENGTH: 17
<212> TYPE: PRT
<213> ORGANISM: Hepatitis C virus

<400> SEQUENCE: 224

Gly Arg Gly Leu Gln Glu Ala Glu Gly Leu Leu Leu Glu Leu Leu Ser
1               5                   10                  15

Glu

<210> SEQ ID NO 225
<211> LENGTH: 17
<212> TYPE: PRT
<213> ORGANISM: Hepatitis C virus

<400> SEQUENCE: 225

Leu Ala Gly Arg Gly Leu Gln Glu Ala Glu Gly Leu Leu Leu Glu Leu
1               5                   10                  15

Leu

<210> SEQ ID NO 226
<211> LENGTH: 17
<212> TYPE: PRT
<213> ORGANISM: Hepatitis C virus

<400> SEQUENCE: 226

Ala Gly Arg Gly Leu Gln Glu Ala Glu Gly Leu Leu Leu Glu Leu Leu
1               5                   10                  15

Ser

<210> SEQ ID NO 227
<211> LENGTH: 17
<212> TYPE: PRT
<213> ORGANISM: Hepatitis C virus

<400> SEQUENCE: 227

Gly Leu Gln Glu Ala Glu Gly Leu Leu Leu Glu Leu Leu Ser Glu His
1               5                   10                  15

His

<210> SEQ ID NO 228
<211> LENGTH: 17
<212> TYPE: PRT
<213> ORGANISM: Hepatitis C virus

<400> SEQUENCE: 228

Glu Gly Leu Leu Leu Glu Leu Leu Ser Glu His His Pro Leu Leu Asp
1               5                   10                  15

Val

<210> SEQ ID NO 229
<211> LENGTH: 17
<212> TYPE: PRT
<213> ORGANISM: Hepatitis C virus

<400> SEQUENCE: 229

Ala Glu Gly Leu Leu Leu Glu Leu Leu Ser Glu His His Pro Leu Leu
1               5                   10                  15

Asp

<210> SEQ ID NO 230
<211> LENGTH: 17
```

```
<212> TYPE: PRT
<213> ORGANISM: Hepatitis C virus

<400> SEQUENCE: 230

Leu Gln Glu Ala Glu Gly Leu Leu Glu Leu Leu Ser Glu His His
1               5                   10                  15

Pro

<210> SEQ ID NO 231
<211> LENGTH: 18
<212> TYPE: PRT
<213> ORGANISM: Hepatitis C virus

<400> SEQUENCE: 231

Cys Leu Ala Gly Arg Gly Leu Gln Glu Ala Glu Gly Leu Leu Glu
1               5                   10                  15

Leu Leu

<210> SEQ ID NO 232
<211> LENGTH: 18
<212> TYPE: PRT
<213> ORGANISM: Hepatitis C virus

<400> SEQUENCE: 232

Leu Gln Glu Ala Glu Gly Leu Leu Glu Leu Leu Ser Glu His His
1               5                   10                  15

Pro Leu

<210> SEQ ID NO 233
<211> LENGTH: 18
<212> TYPE: PRT
<213> ORGANISM: Hepatitis C virus

<400> SEQUENCE: 233

Gly Arg Gly Leu Gln Glu Ala Glu Gly Leu Leu Leu Glu Leu Leu Ser
1               5                   10                  15

Glu His

<210> SEQ ID NO 234
<211> LENGTH: 18
<212> TYPE: PRT
<213> ORGANISM: Hepatitis C virus

<400> SEQUENCE: 234

Glu Ala Glu Gly Leu Leu Leu Glu Leu Leu Ser Glu His His Pro Leu
1               5                   10                  15

Leu Asp

<210> SEQ ID NO 235
<211> LENGTH: 18
<212> TYPE: PRT
<213> ORGANISM: Hepatitis C virus

<400> SEQUENCE: 235

Ala Glu Gly Leu Leu Leu Glu Leu Leu Ser Glu His His Pro Leu Leu
1               5                   10                  15

Asp Val

<210> SEQ ID NO 236
<211> LENGTH: 18
<212> TYPE: PRT
```

<213> ORGANISM: Hepatitis C virus

<400> SEQUENCE: 236

Gly Leu Gln Glu Ala Glu Gly Leu Leu Leu Glu Leu Leu Ser Glu His
1               5                   10                  15

His Pro

<210> SEQ ID NO 237
<211> LENGTH: 18
<212> TYPE: PRT
<213> ORGANISM: Hepatitis C virus

<400> SEQUENCE: 237

Arg Gly Leu Gln Glu Ala Glu Gly Leu Leu Leu Glu Leu Leu Ser Glu
1               5                   10                  15

His His

<210> SEQ ID NO 238
<211> LENGTH: 18
<212> TYPE: PRT
<213> ORGANISM: Hepatitis C virus

<400> SEQUENCE: 238

Gln Glu Ala Glu Gly Leu Leu Leu Glu Leu Leu Ser Glu His His Pro
1               5                   10                  15

Leu Leu

<210> SEQ ID NO 239
<211> LENGTH: 18
<212> TYPE: PRT
<213> ORGANISM: Hepatitis C virus

<400> SEQUENCE: 239

Leu Ala Gly Arg Gly Leu Gln Glu Ala Glu Gly Leu Leu Leu Glu Leu
1               5                   10                  15

Leu Ser

<210> SEQ ID NO 240
<211> LENGTH: 18
<212> TYPE: PRT
<213> ORGANISM: Hepatitis C virus

<400> SEQUENCE: 240

Leu Cys Leu Ala Gly Arg Gly Leu Gln Glu Ala Glu Gly Leu Leu Leu
1               5                   10                  15

Glu Leu

<210> SEQ ID NO 241
<211> LENGTH: 18
<212> TYPE: PRT
<213> ORGANISM: Hepatitis C virus

<400> SEQUENCE: 241

Ala Gly Arg Gly Leu Gln Glu Ala Glu Gly Leu Leu Leu Glu Leu Leu
1               5                   10                  15

Ser Glu

<210> SEQ ID NO 242
<211> LENGTH: 19
<212> TYPE: PRT
<213> ORGANISM: Hepatitis C virus

```
<400> SEQUENCE: 242

Ala Gly Arg Gly Leu Gln Glu Ala Glu Gly Leu Leu Leu Glu Leu Leu
1               5                   10                  15

Ser Glu His

<210> SEQ ID NO 243
<211> LENGTH: 19
<212> TYPE: PRT
<213> ORGANISM: Hepatitis C virus

<400> SEQUENCE: 243

Gly Leu Gln Glu Ala Glu Gly Leu Leu Leu Glu Leu Leu Ser Glu His
1               5                   10                  15

His Pro Leu

<210> SEQ ID NO 244
<211> LENGTH: 19
<212> TYPE: PRT
<213> ORGANISM: Hepatitis C virus

<400> SEQUENCE: 244

Gly Arg Gly Leu Gln Glu Ala Glu Gly Leu Leu Leu Glu Leu Leu Ser
1               5                   10                  15

Glu His His

<210> SEQ ID NO 245
<211> LENGTH: 19
<212> TYPE: PRT
<213> ORGANISM: Hepatitis C virus

<400> SEQUENCE: 245

Leu Cys Leu Ala Gly Arg Gly Leu Gln Glu Ala Glu Gly Leu Leu Leu
1               5                   10                  15

Glu Leu Leu

<210> SEQ ID NO 246
<211> LENGTH: 19
<212> TYPE: PRT
<213> ORGANISM: Hepatitis C virus

<400> SEQUENCE: 246

Cys Leu Ala Gly Arg Gly Leu Gln Glu Ala Glu Gly Leu Leu Leu Glu
1               5                   10                  15

Leu Leu Ser

<210> SEQ ID NO 247
<211> LENGTH: 19
<212> TYPE: PRT
<213> ORGANISM: Hepatitis C virus

<400> SEQUENCE: 247

Arg Gly Leu Gln Glu Ala Glu Gly Leu Leu Leu Glu Leu Leu Ser Glu
1               5                   10                  15

His His Pro

<210> SEQ ID NO 248
<211> LENGTH: 19
<212> TYPE: PRT
<213> ORGANISM: Hepatitis C virus
```

```
<400> SEQUENCE: 248

Leu Ala Gly Arg Gly Leu Gln Glu Ala Glu Gly Leu Leu Leu Glu Leu
1               5                   10                  15

Leu Ser Glu

<210> SEQ ID NO 249
<211> LENGTH: 19
<212> TYPE: PRT
<213> ORGANISM: Hepatitis C virus

<400> SEQUENCE: 249

Gln Glu Ala Glu Gly Leu Leu Leu Glu Leu Leu Ser Glu His His Pro
1               5                   10                  15

Leu Leu Asp

<210> SEQ ID NO 250
<211> LENGTH: 19
<212> TYPE: PRT
<213> ORGANISM: Hepatitis C virus

<400> SEQUENCE: 250

Leu Gln Glu Ala Glu Gly Leu Leu Leu Glu Leu Leu Ser Glu His His
1               5                   10                  15

Pro Leu Leu

<210> SEQ ID NO 251
<211> LENGTH: 19
<212> TYPE: PRT
<213> ORGANISM: Hepatitis C virus

<400> SEQUENCE: 251

Glu Ala Glu Gly Leu Leu Leu Glu Leu Leu Ser Glu His His Pro Leu
1               5                   10                  15

Leu Asp Val

<210> SEQ ID NO 252
<211> LENGTH: 20
<212> TYPE: PRT
<213> ORGANISM: Hepatitis C virus

<400> SEQUENCE: 252

Arg Gly Leu Gln Glu Ala Glu Gly Leu Leu Leu Glu Leu Leu Ser Glu
1               5                   10                  15

His His Pro Leu
            20

<210> SEQ ID NO 253
<211> LENGTH: 20
<212> TYPE: PRT
<213> ORGANISM: Hepatitis C virus

<400> SEQUENCE: 253

Gly Leu Gln Glu Ala Glu Gly Leu Leu Leu Glu Leu Leu Ser Glu His
1               5                   10                  15

His Pro Leu Leu
            20

<210> SEQ ID NO 254
<211> LENGTH: 20
<212> TYPE: PRT
<213> ORGANISM: Hepatitis C virus
```

<400> SEQUENCE: 254

Ala Gly Arg Gly Leu Gln Glu Ala Glu Gly Leu Leu Leu Glu Leu Leu
1               5                   10                  15

Ser Glu His His
            20

<210> SEQ ID NO 255
<211> LENGTH: 20
<212> TYPE: PRT
<213> ORGANISM: Hepatitis C virus

<400> SEQUENCE: 255

Leu Ala Gly Arg Gly Leu Gln Glu Ala Glu Gly Leu Leu Leu Glu Leu
1               5                   10                  15

Leu Ser Glu His
            20

<210> SEQ ID NO 256
<211> LENGTH: 20
<212> TYPE: PRT
<213> ORGANISM: Hepatitis C virus

<400> SEQUENCE: 256

Gly Arg Gly Leu Gln Glu Ala Glu Gly Leu Leu Leu Glu Leu Leu Ser
1               5                   10                  15

Glu His His Pro
            20

<210> SEQ ID NO 257
<211> LENGTH: 20
<212> TYPE: PRT
<213> ORGANISM: Hepatitis C virus

<400> SEQUENCE: 257

Leu Cys Leu Ala Gly Arg Gly Leu Gln Glu Ala Glu Gly Leu Leu Leu
1               5                   10                  15

Glu Leu Leu Ser
            20

<210> SEQ ID NO 258
<211> LENGTH: 20
<212> TYPE: PRT
<213> ORGANISM: Hepatitis C virus

<400> SEQUENCE: 258

Leu Gln Glu Ala Glu Gly Leu Leu Leu Glu Leu Leu Ser Glu His His
1               5                   10                  15

Pro Leu Leu Asp
            20

<210> SEQ ID NO 259
<211> LENGTH: 20
<212> TYPE: PRT
<213> ORGANISM: Hepatitis C virus

<400> SEQUENCE: 259

Gln Glu Ala Glu Gly Leu Leu Leu Glu Leu Leu Ser Glu His His Pro
1               5                   10                  15

Leu Leu Asp Val
            20

<210> SEQ ID NO 260
<211> LENGTH: 20
<212> TYPE: PRT
<213> ORGANISM: Hepatitis C virus

<400> SEQUENCE: 260

Cys Leu Ala Gly Arg Gly Leu Gln Glu Ala Glu Gly Leu Leu Leu Glu
1               5                   10                  15

Leu Leu Ser Glu
            20

<210> SEQ ID NO 261
<211> LENGTH: 21
<212> TYPE: PRT
<213> ORGANISM: Hepatitis C virus

<400> SEQUENCE: 261

Leu Cys Leu Ala Gly Arg Gly Leu Gln Glu Ala Glu Gly Leu Leu Leu
1               5                   10                  15

Glu Leu Leu Ser Glu
            20

<210> SEQ ID NO 262
<211> LENGTH: 21
<212> TYPE: PRT
<213> ORGANISM: Hepatitis C virus

<400> SEQUENCE: 262

Arg Gly Leu Gln Glu Ala Glu Gly Leu Leu Leu Glu Leu Leu Ser Glu
1               5                   10                  15

His His Pro Leu Leu
            20

<210> SEQ ID NO 263
<211> LENGTH: 21
<212> TYPE: PRT
<213> ORGANISM: Hepatitis C virus

<400> SEQUENCE: 263

Leu Gln Glu Ala Glu Gly Leu Leu Leu Glu Leu Leu Ser Glu His His
1               5                   10                  15

Pro Leu Leu Asp Val
            20

<210> SEQ ID NO 264
<211> LENGTH: 21
<212> TYPE: PRT
<213> ORGANISM: Hepatitis C virus

<400> SEQUENCE: 264

Gly Arg Gly Leu Gln Glu Ala Glu Gly Leu Leu Leu Glu Leu Leu Ser
1               5                   10                  15

Glu His His Pro Leu
            20

<210> SEQ ID NO 265
<211> LENGTH: 21
<212> TYPE: PRT
<213> ORGANISM: Hepatitis C virus

<400> SEQUENCE: 265

Ala Gly Arg Gly Leu Gln Glu Ala Glu Gly Leu Leu Leu Glu Leu Leu

```
1               5                   10                  15

Ser Glu His His Pro
            20

<210> SEQ ID NO 266
<211> LENGTH: 21
<212> TYPE: PRT
<213> ORGANISM: Hepatitis C virus

<400> SEQUENCE: 266

Leu Ala Gly Arg Gly Leu Gln Glu Ala Glu Gly Leu Leu Leu Glu Leu
1               5                   10                  15

Leu Ser Glu His His
            20

<210> SEQ ID NO 267
<211> LENGTH: 21
<212> TYPE: PRT
<213> ORGANISM: Hepatitis C virus

<400> SEQUENCE: 267

Cys Leu Ala Gly Arg Gly Leu Gln Glu Ala Glu Gly Leu Leu Leu Glu
1               5                   10                  15

Leu Leu Ser Glu His
            20

<210> SEQ ID NO 268
<211> LENGTH: 21
<212> TYPE: PRT
<213> ORGANISM: Hepatitis C virus

<400> SEQUENCE: 268

Gly Leu Gln Glu Ala Glu Gly Leu Leu Leu Glu Leu Leu Ser Glu His
1               5                   10                  15

His Pro Leu Leu Asp
            20

<210> SEQ ID NO 269
<211> LENGTH: 22
<212> TYPE: PRT
<213> ORGANISM: Hepatitis C virus

<400> SEQUENCE: 269

Gly Leu Gln Glu Ala Glu Gly Leu Leu Leu Glu Leu Leu Ser Glu His
1               5                   10                  15

His Pro Leu Leu Asp Val
            20

<210> SEQ ID NO 270
<211> LENGTH: 22
<212> TYPE: PRT
<213> ORGANISM: Hepatitis C virus

<400> SEQUENCE: 270

Ala Gly Arg Gly Leu Gln Glu Ala Glu Gly Leu Leu Leu Glu Leu Leu
1               5                   10                  15

Ser Glu His His Pro Leu
            20

<210> SEQ ID NO 271
<211> LENGTH: 22
<212> TYPE: PRT
```

<213> ORGANISM: Hepatitis C virus

<400> SEQUENCE: 271

Cys Leu Ala Gly Arg Gly Leu Gln Glu Ala Glu Gly Leu Leu Leu Glu
1               5                   10                  15
Leu Leu Ser Glu His His
            20

<210> SEQ ID NO 272
<211> LENGTH: 22
<212> TYPE: PRT
<213> ORGANISM: Hepatitis C virus

<400> SEQUENCE: 272

Gly Arg Gly Leu Gln Glu Ala Glu Gly Leu Leu Leu Glu Leu Leu Ser
1               5                   10                  15
Glu His His Pro Leu Leu
            20

<210> SEQ ID NO 273
<211> LENGTH: 22
<212> TYPE: PRT
<213> ORGANISM: Hepatitis C virus

<400> SEQUENCE: 273

Arg Gly Leu Gln Glu Ala Glu Gly Leu Leu Leu Glu Leu Leu Ser Glu
1               5                   10                  15
His His Pro Leu Leu Asp
            20

<210> SEQ ID NO 274
<211> LENGTH: 22
<212> TYPE: PRT
<213> ORGANISM: Hepatitis C virus

<400> SEQUENCE: 274

Leu Ala Gly Arg Gly Leu Gln Glu Ala Glu Gly Leu Leu Leu Glu Leu
1               5                   10                  15
Leu Ser Glu His His Pro
            20

<210> SEQ ID NO 275
<211> LENGTH: 22
<212> TYPE: PRT
<213> ORGANISM: Hepatitis C virus

<400> SEQUENCE: 275

Leu Cys Leu Ala Gly Arg Gly Leu Gln Glu Ala Glu Gly Leu Leu Leu
1               5                   10                  15
Glu Leu Leu Ser Glu His
            20

<210> SEQ ID NO 276
<211> LENGTH: 23
<212> TYPE: PRT
<213> ORGANISM: Hepatitis C virus

<400> SEQUENCE: 276

Cys Leu Ala Gly Arg Gly Leu Gln Glu Ala Glu Gly Leu Leu Leu Glu
1               5                   10                  15
Leu Leu Ser Glu His His Pro
            20

<210> SEQ ID NO 277
<211> LENGTH: 23
<212> TYPE: PRT
<213> ORGANISM: Hepatitis C virus

<400> SEQUENCE: 277

Gly Arg Gly Leu Gln Glu Ala Glu Gly Leu Leu Leu Glu Leu Leu Ser
1               5                   10                  15

Glu His His Pro Leu Leu Asp
            20

<210> SEQ ID NO 278
<211> LENGTH: 23
<212> TYPE: PRT
<213> ORGANISM: Hepatitis C virus

<400> SEQUENCE: 278

Leu Cys Leu Ala Gly Arg Gly Leu Gln Glu Ala Glu Gly Leu Leu Leu
1               5                   10                  15

Glu Leu Leu Ser Glu His His
            20

<210> SEQ ID NO 279
<211> LENGTH: 23
<212> TYPE: PRT
<213> ORGANISM: Hepatitis C virus

<400> SEQUENCE: 279

Leu Ala Gly Arg Gly Leu Gln Glu Ala Glu Gly Leu Leu Leu Glu Leu
1               5                   10                  15

Leu Ser Glu His His Pro Leu
            20

<210> SEQ ID NO 280
<211> LENGTH: 23
<212> TYPE: PRT
<213> ORGANISM: Hepatitis C virus

<400> SEQUENCE: 280

Arg Gly Leu Gln Glu Ala Glu Gly Leu Leu Leu Glu Leu Leu Ser Glu
1               5                   10                  15

His His Pro Leu Leu Asp Val
            20

<210> SEQ ID NO 281
<211> LENGTH: 23
<212> TYPE: PRT
<213> ORGANISM: Hepatitis C virus

<400> SEQUENCE: 281

Ala Gly Arg Gly Leu Gln Glu Ala Glu Gly Leu Leu Leu Glu Leu Leu
1               5                   10                  15

Ser Glu His His Pro Leu Leu
            20

<210> SEQ ID NO 282
<211> LENGTH: 24
<212> TYPE: PRT
<213> ORGANISM: Hepatitis C virus

<400> SEQUENCE: 282

```
Ala Gly Arg Gly Leu Gln Glu Ala Glu Gly Leu Leu Leu Glu Leu Leu
1               5                   10                  15

Ser Glu His His Pro Leu Leu Asp
            20
```

<210> SEQ ID NO 283
<211> LENGTH: 24
<212> TYPE: PRT
<213> ORGANISM: Hepatitis C virus

<400> SEQUENCE: 283

```
Cys Leu Ala Gly Arg Gly Leu Gln Glu Ala Glu Gly Leu Leu Leu Glu
1               5                   10                  15

Leu Leu Ser Glu His His Pro Leu
            20
```

<210> SEQ ID NO 284
<211> LENGTH: 24
<212> TYPE: PRT
<213> ORGANISM: Hepatitis C virus

<400> SEQUENCE: 284

```
Leu Cys Leu Ala Gly Arg Gly Leu Gln Glu Ala Glu Gly Leu Leu Leu
1               5                   10                  15

Glu Leu Leu Ser Glu His His Pro
            20
```

<210> SEQ ID NO 285
<211> LENGTH: 24
<212> TYPE: PRT
<213> ORGANISM: Hepatitis C virus

<400> SEQUENCE: 285

```
Gly Arg Gly Leu Gln Glu Ala Glu Gly Leu Leu Leu Glu Leu Leu Ser
1               5                   10                  15

Glu His His Pro Leu Leu Asp Val
            20
```

<210> SEQ ID NO 286
<211> LENGTH: 24
<212> TYPE: PRT
<213> ORGANISM: Hepatitis C virus

<400> SEQUENCE: 286

```
Leu Ala Gly Arg Gly Leu Gln Glu Ala Glu Gly Leu Leu Leu Glu Leu
1               5                   10                  15

Leu Ser Glu His His Pro Leu Leu
            20
```

<210> SEQ ID NO 287
<211> LENGTH: 25
<212> TYPE: PRT
<213> ORGANISM: Hepatitis C virus

<400> SEQUENCE: 287

```
Ala Gly Arg Gly Leu Gln Glu Ala Glu Gly Leu Leu Leu Glu Leu Leu
1               5                   10                  15

Ser Glu His His Pro Leu Leu Asp Val
            20                  25
```

<210> SEQ ID NO 288
<211> LENGTH: 25

-continued

```
<212> TYPE: PRT
<213> ORGANISM: Hepatitis C virus

<400> SEQUENCE: 288

Leu Cys Leu Ala Gly Arg Gly Leu Gln Glu Ala Glu Gly Leu Leu
1               5                   10                  15

Glu Leu Leu Ser Glu His His Pro Leu
            20                  25

<210> SEQ ID NO 289
<211> LENGTH: 25
<212> TYPE: PRT
<213> ORGANISM: Hepatitis C virus

<400> SEQUENCE: 289

Leu Ala Gly Arg Gly Leu Gln Glu Ala Glu Gly Leu Leu Leu Glu Leu
1               5                   10                  15

Leu Ser Glu His His Pro Leu Leu Asp
            20                  25

<210> SEQ ID NO 290
<211> LENGTH: 25
<212> TYPE: PRT
<213> ORGANISM: Hepatitis C virus

<400> SEQUENCE: 290

Cys Leu Ala Gly Arg Gly Leu Gln Glu Ala Glu Gly Leu Leu Leu Glu
1               5                   10                  15

Leu Leu Ser Glu His His Pro Leu Leu
            20                  25

<210> SEQ ID NO 291
<211> LENGTH: 26
<212> TYPE: PRT
<213> ORGANISM: Hepatitis C virus

<400> SEQUENCE: 291

Leu Cys Leu Ala Gly Arg Gly Leu Gln Glu Ala Glu Gly Leu Leu
1               5                   10                  15

Glu Leu Leu Ser Glu His His Pro Leu Leu
            20                  25

<210> SEQ ID NO 292
<211> LENGTH: 26
<212> TYPE: PRT
<213> ORGANISM: Hepatitis C virus

<400> SEQUENCE: 292

Leu Ala Gly Arg Gly Leu Gln Glu Ala Glu Gly Leu Leu Leu Glu Leu
1               5                   10                  15

Leu Ser Glu His His Pro Leu Leu Asp Val
            20                  25

<210> SEQ ID NO 293
<211> LENGTH: 26
<212> TYPE: PRT
<213> ORGANISM: Hepatitis C virus

<400> SEQUENCE: 293

Cys Leu Ala Gly Arg Gly Leu Gln Glu Ala Glu Gly Leu Leu Leu Glu
1               5                   10                  15

Leu Leu Ser Glu His His Pro Leu Leu Asp
```

<210> SEQ ID NO 294
<211> LENGTH: 27
<212> TYPE: PRT
<213> ORGANISM: Hepatitis C virus

<400> SEQUENCE: 294

Leu Cys Leu Ala Gly Arg Gly Leu Gln Glu Ala Glu Gly Leu Leu
1               5                   10                  15

Glu Leu Leu Ser Glu His His Pro Leu Leu Asp
            20                  25

<210> SEQ ID NO 295
<211> LENGTH: 27
<212> TYPE: PRT
<213> ORGANISM: Hepatitis C virus

<400> SEQUENCE: 295

Cys Leu Ala Gly Arg Gly Leu Gln Glu Ala Glu Gly Leu Leu Glu
1               5                   10                  15

Leu Leu Ser Glu His His Pro Leu Leu Asp Val
            20                  25

<210> SEQ ID NO 296
<211> LENGTH: 72
<212> TYPE: RNA
<213> ORGANISM: Hepatitis C virus

<400> SEQUENCE: 296
uggcuaaggg acaucuggga cuggauaugc gaggugcuga gcgacuuuaa gaccuggcug    60
aaagccaagc uc                                                        72

<210> SEQ ID NO 297
<211> LENGTH: 24
<212> TYPE: PRT
<213> ORGANISM: Hepatitis C virus

<400> SEQUENCE: 297

Trp Leu Arg Asp Ile Trp Asp Trp Ile Cys Glu Val Leu Ser Asp Phe
1               5                   10                  15

Lys Thr Trp Leu Lys Ala Lys Leu
            20

<210> SEQ ID NO 298
<211> LENGTH: 72
<212> TYPE: DNA
<213> ORGANISM: Hepatitis C virus

<400> SEQUENCE: 298
gagcttggct ttcagccagg tcttaaagtc gctcagcacc tcgcatatcc agtcccagat    60
gtcccttagc ca                                                        72

<210> SEQ ID NO 299
<211> LENGTH: 22
<212> TYPE: PRT
<213> ORGANISM: Hepatitis C virus

<400> SEQUENCE: 299

Glu Leu Gly Phe Gln Pro Gly Leu Lys Val Ala Gln His Leu Ala Tyr
1               5                   10                  15

```
Pro Val Pro Asp Val Pro
            20

<210> SEQ ID NO 300
<211> LENGTH: 6
<212> TYPE: PRT
<213> ORGANISM: Hepatitis C virus

<400> SEQUENCE: 300

Ala Gln His Leu Ala Tyr
1               5

<210> SEQ ID NO 301
<211> LENGTH: 6
<212> TYPE: PRT
<213> ORGANISM: Hepatitis C virus

<400> SEQUENCE: 301

Leu Gly Phe Gln Pro Gly
1               5

<210> SEQ ID NO 302
<211> LENGTH: 6
<212> TYPE: PRT
<213> ORGANISM: Hepatitis C virus

<400> SEQUENCE: 302

Gly Leu Lys Val Ala Gln
1               5

<210> SEQ ID NO 303
<211> LENGTH: 6
<212> TYPE: PRT
<213> ORGANISM: Hepatitis C virus

<400> SEQUENCE: 303

Glu Leu Gly Phe Gln Pro
1               5

<210> SEQ ID NO 304
<211> LENGTH: 6
<212> TYPE: PRT
<213> ORGANISM: Hepatitis C virus

<400> SEQUENCE: 304

Pro Val Pro Asp Val Pro
1               5

<210> SEQ ID NO 305
<211> LENGTH: 6
<212> TYPE: PRT
<213> ORGANISM: Hepatitis C virus

<400> SEQUENCE: 305

Phe Gln Pro Gly Leu Lys
1               5

<210> SEQ ID NO 306
<211> LENGTH: 6
<212> TYPE: PRT
<213> ORGANISM: Hepatitis C virus

<400> SEQUENCE: 306

Gly Phe Gln Pro Gly Leu
1               5
```

<210> SEQ ID NO 307
<211> LENGTH: 6
<212> TYPE: PRT
<213> ORGANISM: Hepatitis C virus

<400> SEQUENCE: 307

Val Ala Gln His Leu Ala
1               5

<210> SEQ ID NO 308
<211> LENGTH: 6
<212> TYPE: PRT
<213> ORGANISM: Hepatitis C virus

<400> SEQUENCE: 308

Leu Lys Val Ala Gln His
1               5

<210> SEQ ID NO 309
<211> LENGTH: 6
<212> TYPE: PRT
<213> ORGANISM: Hepatitis C virus

<400> SEQUENCE: 309

His Leu Ala Tyr Pro Val
1               5

<210> SEQ ID NO 310
<211> LENGTH: 6
<212> TYPE: PRT
<213> ORGANISM: Hepatitis C virus

<400> SEQUENCE: 310

Lys Val Ala Gln His Leu
1               5

<210> SEQ ID NO 311
<211> LENGTH: 6
<212> TYPE: PRT
<213> ORGANISM: Hepatitis C virus

<400> SEQUENCE: 311

Gln Pro Gly Leu Lys Val
1               5

<210> SEQ ID NO 312
<211> LENGTH: 6
<212> TYPE: PRT
<213> ORGANISM: Hepatitis C virus

<400> SEQUENCE: 312

Leu Ala Tyr Pro Val Pro
1               5

<210> SEQ ID NO 313
<211> LENGTH: 6
<212> TYPE: PRT
<213> ORGANISM: Hepatitis C virus

<400> SEQUENCE: 313

Tyr Pro Val Pro Asp Val
1               5

```
<210> SEQ ID NO 314
<211> LENGTH: 6
<212> TYPE: PRT
<213> ORGANISM: Hepatitis C virus

<400> SEQUENCE: 314

Gln His Leu Ala Tyr Pro
1               5

<210> SEQ ID NO 315
<211> LENGTH: 6
<212> TYPE: PRT
<213> ORGANISM: Hepatitis C virus

<400> SEQUENCE: 315

Pro Gly Leu Lys Val Ala
1               5

<210> SEQ ID NO 316
<211> LENGTH: 6
<212> TYPE: PRT
<213> ORGANISM: Hepatitis C virus

<400> SEQUENCE: 316

Ala Tyr Pro Val Pro Asp
1               5

<210> SEQ ID NO 317
<211> LENGTH: 7
<212> TYPE: PRT
<213> ORGANISM: Hepatitis C virus

<400> SEQUENCE: 317

Gln Pro Gly Leu Lys Val Ala
1               5

<210> SEQ ID NO 318
<211> LENGTH: 7
<212> TYPE: PRT
<213> ORGANISM: Hepatitis C virus

<400> SEQUENCE: 318

Glu Leu Gly Phe Gln Pro Gly
1               5

<210> SEQ ID NO 319
<211> LENGTH: 7
<212> TYPE: PRT
<213> ORGANISM: Hepatitis C virus

<400> SEQUENCE: 319

His Leu Ala Tyr Pro Val Pro
1               5

<210> SEQ ID NO 320
<211> LENGTH: 7
<212> TYPE: PRT
<213> ORGANISM: Hepatitis C virus

<400> SEQUENCE: 320

Leu Ala Tyr Pro Val Pro Asp
1               5

<210> SEQ ID NO 321
<211> LENGTH: 7
```

```
<212> TYPE: PRT
<213> ORGANISM: Hepatitis C virus

<400> SEQUENCE: 321

Ala Gln His Leu Ala Tyr Pro
1               5

<210> SEQ ID NO 322
<211> LENGTH: 7
<212> TYPE: PRT
<213> ORGANISM: Hepatitis C virus

<400> SEQUENCE: 322

Phe Gln Pro Gly Leu Lys Val
1               5

<210> SEQ ID NO 323
<211> LENGTH: 7
<212> TYPE: PRT
<213> ORGANISM: Hepatitis C virus

<400> SEQUENCE: 323

Lys Val Ala Gln His Leu Ala
1               5

<210> SEQ ID NO 324
<211> LENGTH: 7
<212> TYPE: PRT
<213> ORGANISM: Hepatitis C virus

<400> SEQUENCE: 324

Leu Gly Phe Gln Pro Gly Leu
1               5

<210> SEQ ID NO 325
<211> LENGTH: 7
<212> TYPE: PRT
<213> ORGANISM: Hepatitis C virus

<400> SEQUENCE: 325

Ala Tyr Pro Val Pro Asp Val
1               5

<210> SEQ ID NO 326
<211> LENGTH: 7
<212> TYPE: PRT
<213> ORGANISM: Hepatitis C virus

<400> SEQUENCE: 326

Pro Gly Leu Lys Val Ala Gln
1               5

<210> SEQ ID NO 327
<211> LENGTH: 7
<212> TYPE: PRT
<213> ORGANISM: Hepatitis C virus

<400> SEQUENCE: 327

Leu Lys Val Ala Gln His Leu
1               5

<210> SEQ ID NO 328
<211> LENGTH: 7
<212> TYPE: PRT
<213> ORGANISM: Hepatitis C virus
```

```
<400> SEQUENCE: 328

Gly Leu Lys Val Ala Gln His
1               5

<210> SEQ ID NO 329
<211> LENGTH: 7
<212> TYPE: PRT
<213> ORGANISM: Hepatitis C virus

<400> SEQUENCE: 329

Val Ala Gln His Leu Ala Tyr
1               5

<210> SEQ ID NO 330
<211> LENGTH: 7
<212> TYPE: PRT
<213> ORGANISM: Hepatitis C virus

<400> SEQUENCE: 330

Gly Phe Gln Pro Gly Leu Lys
1               5

<210> SEQ ID NO 331
<211> LENGTH: 7
<212> TYPE: PRT
<213> ORGANISM: Hepatitis C virus

<400> SEQUENCE: 331

Gln His Leu Ala Tyr Pro Val
1               5

<210> SEQ ID NO 332
<211> LENGTH: 7
<212> TYPE: PRT
<213> ORGANISM: Hepatitis C virus

<400> SEQUENCE: 332

Tyr Pro Val Pro Asp Val Pro
1               5

<210> SEQ ID NO 333
<211> LENGTH: 8
<212> TYPE: PRT
<213> ORGANISM: Hepatitis C virus

<400> SEQUENCE: 333

Ala Tyr Pro Val Pro Asp Val Pro
1               5

<210> SEQ ID NO 334
<211> LENGTH: 8
<212> TYPE: PRT
<213> ORGANISM: Hepatitis C virus

<400> SEQUENCE: 334

Pro Gly Leu Lys Val Ala Gln His
1               5

<210> SEQ ID NO 335
<211> LENGTH: 8
<212> TYPE: PRT
<213> ORGANISM: Hepatitis C virus

<400> SEQUENCE: 335
```

```
Gln His Leu Ala Tyr Pro Val Pro
1               5

<210> SEQ ID NO 336
<211> LENGTH: 8
<212> TYPE: PRT
<213> ORGANISM: Hepatitis C virus

<400> SEQUENCE: 336

Leu Ala Tyr Pro Val Pro Asp Val
1               5

<210> SEQ ID NO 337
<211> LENGTH: 8
<212> TYPE: PRT
<213> ORGANISM: Hepatitis C virus

<400> SEQUENCE: 337

Leu Lys Val Ala Gln His Leu Ala
1               5

<210> SEQ ID NO 338
<211> LENGTH: 8
<212> TYPE: PRT
<213> ORGANISM: Hepatitis C virus

<400> SEQUENCE: 338

Gly Leu Lys Val Ala Gln His Leu
1               5

<210> SEQ ID NO 339
<211> LENGTH: 8
<212> TYPE: PRT
<213> ORGANISM: Hepatitis C virus

<400> SEQUENCE: 339

Gly Phe Gln Pro Gly Leu Lys Val
1               5

<210> SEQ ID NO 340
<211> LENGTH: 8
<212> TYPE: PRT
<213> ORGANISM: Hepatitis C virus

<400> SEQUENCE: 340

Ala Gln His Leu Ala Tyr Pro Val
1               5

<210> SEQ ID NO 341
<211> LENGTH: 8
<212> TYPE: PRT
<213> ORGANISM: Hepatitis C virus

<400> SEQUENCE: 341

Val Ala Gln His Leu Ala Tyr Pro
1               5

<210> SEQ ID NO 342
<211> LENGTH: 8
<212> TYPE: PRT
<213> ORGANISM: Hepatitis C virus

<400> SEQUENCE: 342

Lys Val Ala Gln His Leu Ala Tyr
```

1               5

<210> SEQ ID NO 343
<211> LENGTH: 8
<212> TYPE: PRT
<213> ORGANISM: Hepatitis C virus

<400> SEQUENCE: 343

Glu Leu Gly Phe Gln Pro Gly Leu
1               5

<210> SEQ ID NO 344
<211> LENGTH: 8
<212> TYPE: PRT
<213> ORGANISM: Hepatitis C virus

<400> SEQUENCE: 344

Leu Gly Phe Gln Pro Gly Leu Lys
1               5

<210> SEQ ID NO 345
<211> LENGTH: 8
<212> TYPE: PRT
<213> ORGANISM: Hepatitis C virus

<400> SEQUENCE: 345

Phe Gln Pro Gly Leu Lys Val Ala
1               5

<210> SEQ ID NO 346
<211> LENGTH: 8
<212> TYPE: PRT
<213> ORGANISM: Hepatitis C virus

<400> SEQUENCE: 346

His Leu Ala Tyr Pro Val Pro Asp
1               5

<210> SEQ ID NO 347
<211> LENGTH: 8
<212> TYPE: PRT
<213> ORGANISM: Hepatitis C virus

<400> SEQUENCE: 347

Gln Pro Gly Leu Lys Val Ala Gln
1               5

<210> SEQ ID NO 348
<211> LENGTH: 9
<212> TYPE: PRT
<213> ORGANISM: Hepatitis C virus

<400> SEQUENCE: 348

Glu Leu Gly Phe Gln Pro Gly Leu Lys
1               5

<210> SEQ ID NO 349
<211> LENGTH: 9
<212> TYPE: PRT
<213> ORGANISM: Hepatitis C virus

<400> SEQUENCE: 349

Val Ala Gln His Leu Ala Tyr Pro Val
1               5

```
<210> SEQ ID NO 350
<211> LENGTH: 9
<212> TYPE: PRT
<213> ORGANISM: Hepatitis C virus

<400> SEQUENCE: 350

Leu Gly Phe Gln Pro Gly Leu Lys Val
1               5

<210> SEQ ID NO 351
<211> LENGTH: 9
<212> TYPE: PRT
<213> ORGANISM: Hepatitis C virus

<400> SEQUENCE: 351

Gln Pro Gly Leu Lys Val Ala Gln His
1               5

<210> SEQ ID NO 352
<211> LENGTH: 9
<212> TYPE: PRT
<213> ORGANISM: Hepatitis C virus

<400> SEQUENCE: 352

Lys Val Ala Gln His Leu Ala Tyr Pro
1               5

<210> SEQ ID NO 353
<211> LENGTH: 9
<212> TYPE: PRT
<213> ORGANISM: Hepatitis C virus

<400> SEQUENCE: 353

Pro Gly Leu Lys Val Ala Gln His Leu
1               5

<210> SEQ ID NO 354
<211> LENGTH: 9
<212> TYPE: PRT
<213> ORGANISM: Hepatitis C virus

<400> SEQUENCE: 354

Phe Gln Pro Gly Leu Lys Val Ala Gln
1               5

<210> SEQ ID NO 355
<211> LENGTH: 9
<212> TYPE: PRT
<213> ORGANISM: Hepatitis C virus

<400> SEQUENCE: 355

Gly Leu Lys Val Ala Gln His Leu Ala
1               5

<210> SEQ ID NO 356
<211> LENGTH: 9
<212> TYPE: PRT
<213> ORGANISM: Hepatitis C virus

<400> SEQUENCE: 356

Leu Ala Tyr Pro Val Pro Asp Val Pro
1               5

<210> SEQ ID NO 357
```

-continued

<211> LENGTH: 9
<212> TYPE: PRT
<213> ORGANISM: Hepatitis C virus

<400> SEQUENCE: 357

His Leu Ala Tyr Pro Val Pro Asp Val
1 5

<210> SEQ ID NO 358
<211> LENGTH: 9
<212> TYPE: PRT
<213> ORGANISM: Hepatitis C virus

<400> SEQUENCE: 358

Gly Phe Gln Pro Gly Leu Lys Val Ala
1 5

<210> SEQ ID NO 359
<211> LENGTH: 9
<212> TYPE: PRT
<213> ORGANISM: Hepatitis C virus

<400> SEQUENCE: 359

Ala Gln His Leu Ala Tyr Pro Val Pro
1 5

<210> SEQ ID NO 360
<211> LENGTH: 9
<212> TYPE: PRT
<213> ORGANISM: Hepatitis C virus

<400> SEQUENCE: 360

Gln His Leu Ala Tyr Pro Val Pro Asp
1 5

<210> SEQ ID NO 361
<211> LENGTH: 9
<212> TYPE: PRT
<213> ORGANISM: Hepatitis C virus

<400> SEQUENCE: 361

Leu Lys Val Ala Gln His Leu Ala Tyr
1 5

<210> SEQ ID NO 362
<211> LENGTH: 10
<212> TYPE: PRT
<213> ORGANISM: Hepatitis C virus

<400> SEQUENCE: 362

Gln Pro Gly Leu Lys Val Ala Gln His Leu
1 5 10

<210> SEQ ID NO 363
<211> LENGTH: 10
<212> TYPE: PRT
<213> ORGANISM: Hepatitis C virus

<400> SEQUENCE: 363

Pro Gly Leu Lys Val Ala Gln His Leu Ala
1 5 10

<210> SEQ ID NO 364
<211> LENGTH: 10
<212> TYPE: PRT

-continued

<213> ORGANISM: Hepatitis C virus

<400> SEQUENCE: 364

His Leu Ala Tyr Pro Val Pro Asp Val Pro
1               5                   10

<210> SEQ ID NO 365
<211> LENGTH: 10
<212> TYPE: PRT
<213> ORGANISM: Hepatitis C virus

<400> SEQUENCE: 365

Gly Leu Lys Val Ala Gln His Leu Ala Tyr
1               5                   10

<210> SEQ ID NO 366
<211> LENGTH: 10
<212> TYPE: PRT
<213> ORGANISM: Hepatitis C virus

<400> SEQUENCE: 366

Val Ala Gln His Leu Ala Tyr Pro Val Pro
1               5                   10

<210> SEQ ID NO 367
<211> LENGTH: 10
<212> TYPE: PRT
<213> ORGANISM: Hepatitis C virus

<400> SEQUENCE: 367

Lys Val Ala Gln His Leu Ala Tyr Pro Val
1               5                   10

<210> SEQ ID NO 368
<211> LENGTH: 10
<212> TYPE: PRT
<213> ORGANISM: Hepatitis C virus

<400> SEQUENCE: 368

Gly Phe Gln Pro Gly Leu Lys Val Ala Gln
1               5                   10

<210> SEQ ID NO 369
<211> LENGTH: 10
<212> TYPE: PRT
<213> ORGANISM: Hepatitis C virus

<400> SEQUENCE: 369

Gln His Leu Ala Tyr Pro Val Pro Asp Val
1               5                   10

<210> SEQ ID NO 370
<211> LENGTH: 10
<212> TYPE: PRT
<213> ORGANISM: Hepatitis C virus

<400> SEQUENCE: 370

Ala Gln His Leu Ala Tyr Pro Val Pro Asp
1               5                   10

<210> SEQ ID NO 371
<211> LENGTH: 10
<212> TYPE: PRT
<213> ORGANISM: Hepatitis C virus

<400> SEQUENCE: 371

Phe Gln Pro Gly Leu Lys Val Ala Gln His
1               5                   10

<210> SEQ ID NO 372
<211> LENGTH: 10
<212> TYPE: PRT
<213> ORGANISM: Hepatitis C virus

<400> SEQUENCE: 372

Glu Leu Gly Phe Gln Pro Gly Leu Lys Val
1               5                   10

<210> SEQ ID NO 373
<211> LENGTH: 10
<212> TYPE: PRT
<213> ORGANISM: Hepatitis C virus

<400> SEQUENCE: 373

Leu Lys Val Ala Gln His Leu Ala Tyr Pro
1               5                   10

<210> SEQ ID NO 374
<211> LENGTH: 10
<212> TYPE: PRT
<213> ORGANISM: Hepatitis C virus

<400> SEQUENCE: 374

Leu Gly Phe Gln Pro Gly Leu Lys Val Ala
1               5                   10

<210> SEQ ID NO 375
<211> LENGTH: 11
<212> TYPE: PRT
<213> ORGANISM: Hepatitis C virus

<400> SEQUENCE: 375

Gln His Leu Ala Tyr Pro Val Pro Asp Val Pro
1               5                   10

<210> SEQ ID NO 376
<211> LENGTH: 11
<212> TYPE: PRT
<213> ORGANISM: Hepatitis C virus

<400> SEQUENCE: 376

Leu Lys Val Ala Gln His Leu Ala Tyr Pro Val
1               5                   10

<210> SEQ ID NO 377
<211> LENGTH: 11
<212> TYPE: PRT
<213> ORGANISM: Hepatitis C virus

<400> SEQUENCE: 377

Val Ala Gln His Leu Ala Tyr Pro Val Pro Asp
1               5                   10

<210> SEQ ID NO 378
<211> LENGTH: 11
<212> TYPE: PRT
<213> ORGANISM: Hepatitis C virus

<400> SEQUENCE: 378

-continued

Pro Gly Leu Lys Val Ala Gln His Leu Ala Tyr
1               5                   10

<210> SEQ ID NO 379
<211> LENGTH: 11
<212> TYPE: PRT
<213> ORGANISM: Hepatitis C virus

<400> SEQUENCE: 379

Leu Gly Phe Gln Pro Gly Leu Lys Val Ala Gln
1               5                   10

<210> SEQ ID NO 380
<211> LENGTH: 11
<212> TYPE: PRT
<213> ORGANISM: Hepatitis C virus

<400> SEQUENCE: 380

Lys Val Ala Gln His Leu Ala Tyr Pro Val Pro
1               5                   10

<210> SEQ ID NO 381
<211> LENGTH: 11
<212> TYPE: PRT
<213> ORGANISM: Hepatitis C virus

<400> SEQUENCE: 381

Glu Leu Gly Phe Gln Pro Gly Leu Lys Val Ala
1               5                   10

<210> SEQ ID NO 382
<211> LENGTH: 11
<212> TYPE: PRT
<213> ORGANISM: Hepatitis C virus

<400> SEQUENCE: 382

Gly Leu Lys Val Ala Gln His Leu Ala Tyr Pro
1               5                   10

<210> SEQ ID NO 383
<211> LENGTH: 11
<212> TYPE: PRT
<213> ORGANISM: Hepatitis C virus

<400> SEQUENCE: 383

Ala Gln His Leu Ala Tyr Pro Val Pro Asp Val
1               5                   10

<210> SEQ ID NO 384
<211> LENGTH: 11
<212> TYPE: PRT
<213> ORGANISM: Hepatitis C virus

<400> SEQUENCE: 384

Phe Gln Pro Gly Leu Lys Val Ala Gln His Leu
1               5                   10

<210> SEQ ID NO 385
<211> LENGTH: 11
<212> TYPE: PRT
<213> ORGANISM: Hepatitis C virus

<400> SEQUENCE: 385

Gln Pro Gly Leu Lys Val Ala Gln His Leu Ala
1               5                   10

```
<210> SEQ ID NO 386
<211> LENGTH: 11
<212> TYPE: PRT
<213> ORGANISM: Hepatitis C virus

<400> SEQUENCE: 386

Gly Phe Gln Pro Gly Leu Lys Val Ala Gln His
1               5                   10

<210> SEQ ID NO 387
<211> LENGTH: 12
<212> TYPE: PRT
<213> ORGANISM: Hepatitis C virus

<400> SEQUENCE: 387

Leu Gly Phe Gln Pro Gly Leu Lys Val Ala Gln His
1               5                   10

<210> SEQ ID NO 388
<211> LENGTH: 12
<212> TYPE: PRT
<213> ORGANISM: Hepatitis C virus

<400> SEQUENCE: 388

Pro Gly Leu Lys Val Ala Gln His Leu Ala Tyr Pro
1               5                   10

<210> SEQ ID NO 389
<211> LENGTH: 12
<212> TYPE: PRT
<213> ORGANISM: Hepatitis C virus

<400> SEQUENCE: 389

Leu Lys Val Ala Gln His Leu Ala Tyr Pro Val Pro
1               5                   10

<210> SEQ ID NO 390
<211> LENGTH: 12
<212> TYPE: PRT
<213> ORGANISM: Hepatitis C virus

<400> SEQUENCE: 390

Gly Phe Gln Pro Gly Leu Lys Val Ala Gln His Leu
1               5                   10

<210> SEQ ID NO 391
<211> LENGTH: 12
<212> TYPE: PRT
<213> ORGANISM: Hepatitis C virus

<400> SEQUENCE: 391

Val Ala Gln His Leu Ala Tyr Pro Val Pro Asp Val
1               5                   10

<210> SEQ ID NO 392
<211> LENGTH: 12
<212> TYPE: PRT
<213> ORGANISM: Hepatitis C virus

<400> SEQUENCE: 392

Gln Pro Gly Leu Lys Val Ala Gln His Leu Ala Tyr
1               5                   10
```

<210> SEQ ID NO 393
<211> LENGTH: 12
<212> TYPE: PRT
<213> ORGANISM: Hepatitis C virus

<400> SEQUENCE: 393

Glu Leu Gly Phe Gln Pro Gly Leu Lys Val Ala Gln
1               5                   10

<210> SEQ ID NO 394
<211> LENGTH: 12
<212> TYPE: PRT
<213> ORGANISM: Hepatitis C virus

<400> SEQUENCE: 394

Ala Gln His Leu Ala Tyr Pro Val Pro Asp Val Pro
1               5                   10

<210> SEQ ID NO 395
<211> LENGTH: 12
<212> TYPE: PRT
<213> ORGANISM: Hepatitis C virus

<400> SEQUENCE: 395

Lys Val Ala Gln His Leu Ala Tyr Pro Val Pro Asp
1               5                   10

<210> SEQ ID NO 396
<211> LENGTH: 12
<212> TYPE: PRT
<213> ORGANISM: Hepatitis C virus

<400> SEQUENCE: 396

Phe Gln Pro Gly Leu Lys Val Ala Gln His Leu Ala
1               5                   10

<210> SEQ ID NO 397
<211> LENGTH: 12
<212> TYPE: PRT
<213> ORGANISM: Hepatitis C virus

<400> SEQUENCE: 397

Gly Leu Lys Val Ala Gln His Leu Ala Tyr Pro Val
1               5                   10

<210> SEQ ID NO 398
<211> LENGTH: 13
<212> TYPE: PRT
<213> ORGANISM: Hepatitis C virus

<400> SEQUENCE: 398

Leu Gly Phe Gln Pro Gly Leu Lys Val Ala Gln His Leu
1               5                   10

<210> SEQ ID NO 399
<211> LENGTH: 13
<212> TYPE: PRT
<213> ORGANISM: Hepatitis C virus

<400> SEQUENCE: 399

Val Ala Gln His Leu Ala Tyr Pro Val Pro Asp Val Pro
1               5                   10

<210> SEQ ID NO 400
<211> LENGTH: 13

```
<212> TYPE: PRT
<213> ORGANISM: Hepatitis C virus

<400> SEQUENCE: 400

Pro Gly Leu Lys Val Ala Gln His Leu Ala Tyr Pro Val
1               5                   10

<210> SEQ ID NO 401
<211> LENGTH: 13
<212> TYPE: PRT
<213> ORGANISM: Hepatitis C virus

<400> SEQUENCE: 401

Gly Phe Gln Pro Gly Leu Lys Val Ala Gln His Leu Ala
1               5                   10

<210> SEQ ID NO 402
<211> LENGTH: 13
<212> TYPE: PRT
<213> ORGANISM: Hepatitis C virus

<400> SEQUENCE: 402

Leu Lys Val Ala Gln His Leu Ala Tyr Pro Val Pro Asp
1               5                   10

<210> SEQ ID NO 403
<211> LENGTH: 13
<212> TYPE: PRT
<213> ORGANISM: Hepatitis C virus

<400> SEQUENCE: 403

Gln Pro Gly Leu Lys Val Ala Gln His Leu Ala Tyr Pro
1               5                   10

<210> SEQ ID NO 404
<211> LENGTH: 13
<212> TYPE: PRT
<213> ORGANISM: Hepatitis C virus

<400> SEQUENCE: 404

Glu Leu Gly Phe Gln Pro Gly Leu Lys Val Ala Gln His
1               5                   10

<210> SEQ ID NO 405
<211> LENGTH: 13
<212> TYPE: PRT
<213> ORGANISM: Hepatitis C virus

<400> SEQUENCE: 405

Gly Leu Lys Val Ala Gln His Leu Ala Tyr Pro Val Pro
1               5                   10

<210> SEQ ID NO 406
<211> LENGTH: 13
<212> TYPE: PRT
<213> ORGANISM: Hepatitis C virus

<400> SEQUENCE: 406

Phe Gln Pro Gly Leu Lys Val Ala Gln His Leu Ala Tyr
1               5                   10

<210> SEQ ID NO 407
<211> LENGTH: 13
<212> TYPE: PRT
<213> ORGANISM: Hepatitis C virus
```

<400> SEQUENCE: 407

Lys Val Ala Gln His Leu Ala Tyr Pro Val Pro Asp Val
1               5                   10

<210> SEQ ID NO 408
<211> LENGTH: 14
<212> TYPE: PRT
<213> ORGANISM: Hepatitis C virus

<400> SEQUENCE: 408

Glu Leu Gly Phe Gln Pro Gly Leu Lys Val Ala Gln His Leu
1               5                   10

<210> SEQ ID NO 409
<211> LENGTH: 14
<212> TYPE: PRT
<213> ORGANISM: Hepatitis C virus

<400> SEQUENCE: 409

Gln Pro Gly Leu Lys Val Ala Gln His Leu Ala Tyr Pro Val
1               5                   10

<210> SEQ ID NO 410
<211> LENGTH: 14
<212> TYPE: PRT
<213> ORGANISM: Hepatitis C virus

<400> SEQUENCE: 410

Gly Phe Gln Pro Gly Leu Lys Val Ala Gln His Leu Ala Tyr
1               5                   10

<210> SEQ ID NO 411
<211> LENGTH: 14
<212> TYPE: PRT
<213> ORGANISM: Hepatitis C virus

<400> SEQUENCE: 411

Leu Gly Phe Gln Pro Gly Leu Lys Val Ala Gln His Leu Ala
1               5                   10

<210> SEQ ID NO 412
<211> LENGTH: 14
<212> TYPE: PRT
<213> ORGANISM: Hepatitis C virus

<400> SEQUENCE: 412

Phe Gln Pro Gly Leu Lys Val Ala Gln His Leu Ala Tyr Pro
1               5                   10

<210> SEQ ID NO 413
<211> LENGTH: 14
<212> TYPE: PRT
<213> ORGANISM: Hepatitis C virus

<400> SEQUENCE: 413

Lys Val Ala Gln His Leu Ala Tyr Pro Val Pro Asp Val Pro
1               5                   10

<210> SEQ ID NO 414
<211> LENGTH: 14
<212> TYPE: PRT
<213> ORGANISM: Hepatitis C virus

<400> SEQUENCE: 414

Pro Gly Leu Lys Val Ala Gln His Leu Ala Tyr Pro Val Pro
1               5                   10

<210> SEQ ID NO 415
<211> LENGTH: 14
<212> TYPE: PRT
<213> ORGANISM: Hepatitis C virus

<400> SEQUENCE: 415

Leu Lys Val Ala Gln His Leu Ala Tyr Pro Val Pro Asp Val
1               5                   10

<210> SEQ ID NO 416
<211> LENGTH: 14
<212> TYPE: PRT
<213> ORGANISM: Hepatitis C virus

<400> SEQUENCE: 416

Gly Leu Lys Val Ala Gln His Leu Ala Tyr Pro Val Pro Asp
1               5                   10

<210> SEQ ID NO 417
<211> LENGTH: 15
<212> TYPE: PRT
<213> ORGANISM: Hepatitis C virus

<400> SEQUENCE: 417

Gly Leu Lys Val Ala Gln His Leu Ala Tyr Pro Val Pro Asp Val
1               5                   10                  15

<210> SEQ ID NO 418
<211> LENGTH: 15
<212> TYPE: PRT
<213> ORGANISM: Hepatitis C virus

<400> SEQUENCE: 418

Pro Gly Leu Lys Val Ala Gln His Leu Ala Tyr Pro Val Pro Asp
1               5                   10                  15

<210> SEQ ID NO 419
<211> LENGTH: 15
<212> TYPE: PRT
<213> ORGANISM: Hepatitis C virus

<400> SEQUENCE: 419

Glu Leu Gly Phe Gln Pro Gly Leu Lys Val Ala Gln His Leu Ala
1               5                   10                  15

<210> SEQ ID NO 420
<211> LENGTH: 15
<212> TYPE: PRT
<213> ORGANISM: Hepatitis C virus

<400> SEQUENCE: 420

Leu Gly Phe Gln Pro Gly Leu Lys Val Ala Gln His Leu Ala Tyr
1               5                   10                  15

<210> SEQ ID NO 421
<211> LENGTH: 15
<212> TYPE: PRT
<213> ORGANISM: Hepatitis C virus

<400> SEQUENCE: 421

Gly Phe Gln Pro Gly Leu Lys Val Ala Gln His Leu Ala Tyr Pro

```
<210> SEQ ID NO 422
<211> LENGTH: 15
<212> TYPE: PRT
<213> ORGANISM: Hepatitis C virus

<400> SEQUENCE: 422

Gln Pro Gly Leu Lys Val Ala Gln His Leu Ala Tyr Pro Val Pro
1               5                   10                  15

<210> SEQ ID NO 423
<211> LENGTH: 15
<212> TYPE: PRT
<213> ORGANISM: Hepatitis C virus

<400> SEQUENCE: 423

Phe Gln Pro Gly Leu Lys Val Ala Gln His Leu Ala Tyr Pro Val
1               5                   10                  15

<210> SEQ ID NO 424
<211> LENGTH: 15
<212> TYPE: PRT
<213> ORGANISM: Hepatitis C virus

<400> SEQUENCE: 424

Leu Lys Val Ala Gln His Leu Ala Tyr Pro Val Pro Asp Val Pro
1               5                   10                  15

<210> SEQ ID NO 425
<211> LENGTH: 16
<212> TYPE: PRT
<213> ORGANISM: Hepatitis C virus

<400> SEQUENCE: 425

Phe Gln Pro Gly Leu Lys Val Ala Gln His Leu Ala Tyr Pro Val Pro
1               5                   10                  15

<210> SEQ ID NO 426
<211> LENGTH: 16
<212> TYPE: PRT
<213> ORGANISM: Hepatitis C virus

<400> SEQUENCE: 426

Gly Phe Gln Pro Gly Leu Lys Val Ala Gln His Leu Ala Tyr Pro Val
1               5                   10                  15

<210> SEQ ID NO 427
<211> LENGTH: 16
<212> TYPE: PRT
<213> ORGANISM: Hepatitis C virus

<400> SEQUENCE: 427

Gly Leu Lys Val Ala Gln His Leu Ala Tyr Pro Val Pro Asp Val Pro
1               5                   10                  15

<210> SEQ ID NO 428
<211> LENGTH: 16
<212> TYPE: PRT
<213> ORGANISM: Hepatitis C virus

<400> SEQUENCE: 428

Pro Gly Leu Lys Val Ala Gln His Leu Ala Tyr Pro Val Pro Asp Val
1               5                   10                  15
```

<210> SEQ ID NO 429
<211> LENGTH: 16
<212> TYPE: PRT
<213> ORGANISM: Hepatitis C virus

<400> SEQUENCE: 429

Gln Pro Gly Leu Lys Val Ala Gln His Leu Ala Tyr Pro Val Pro Asp
1               5                   10                  15

<210> SEQ ID NO 430
<211> LENGTH: 16
<212> TYPE: PRT
<213> ORGANISM: Hepatitis C virus

<400> SEQUENCE: 430

Glu Leu Gly Phe Gln Pro Gly Leu Lys Val Ala Gln His Leu Ala Tyr
1               5                   10                  15

<210> SEQ ID NO 431
<211> LENGTH: 16
<212> TYPE: PRT
<213> ORGANISM: Hepatitis C virus

<400> SEQUENCE: 431

Leu Gly Phe Gln Pro Gly Leu Lys Val Ala Gln His Leu Ala Tyr Pro
1               5                   10                  15

<210> SEQ ID NO 432
<211> LENGTH: 17
<212> TYPE: PRT
<213> ORGANISM: Hepatitis C virus

<400> SEQUENCE: 432

Gly Phe Gln Pro Gly Leu Lys Val Ala Gln His Leu Ala Tyr Pro Val
1               5                   10                  15

Pro

<210> SEQ ID NO 433
<211> LENGTH: 17
<212> TYPE: PRT
<213> ORGANISM: Hepatitis C virus

<400> SEQUENCE: 433

Phe Gln Pro Gly Leu Lys Val Ala Gln His Leu Ala Tyr Pro Val Pro
1               5                   10                  15

Asp

<210> SEQ ID NO 434
<211> LENGTH: 17
<212> TYPE: PRT
<213> ORGANISM: Hepatitis C virus

<400> SEQUENCE: 434

Gln Pro Gly Leu Lys Val Ala Gln His Leu Ala Tyr Pro Val Pro Asp
1               5                   10                  15

Val

<210> SEQ ID NO 435
<211> LENGTH: 17
<212> TYPE: PRT
<213> ORGANISM: Hepatitis C virus

<400> SEQUENCE: 435

```
Pro Gly Leu Lys Val Ala Gln His Leu Ala Tyr Pro Val Pro Asp Val
1               5                   10                  15
Pro
```

<210> SEQ ID NO 436
<211> LENGTH: 17
<212> TYPE: PRT
<213> ORGANISM: Hepatitis C virus

<400> SEQUENCE: 436

```
Leu Gly Phe Gln Pro Gly Leu Lys Val Ala Gln His Leu Ala Tyr Pro
1               5                   10                  15
Val
```

<210> SEQ ID NO 437
<211> LENGTH: 17
<212> TYPE: PRT
<213> ORGANISM: Hepatitis C virus

<400> SEQUENCE: 437

```
Glu Leu Gly Phe Gln Pro Gly Leu Lys Val Ala Gln His Leu Ala Tyr
1               5                   10                  15
Pro
```

<210> SEQ ID NO 438
<211> LENGTH: 18
<212> TYPE: PRT
<213> ORGANISM: Hepatitis C virus

<400> SEQUENCE: 438

```
Glu Leu Gly Phe Gln Pro Gly Leu Lys Val Ala Gln His Leu Ala Tyr
1               5                   10                  15
Pro Val
```

<210> SEQ ID NO 439
<211> LENGTH: 18
<212> TYPE: PRT
<213> ORGANISM: Hepatitis C virus

<400> SEQUENCE: 439

```
Gln Pro Gly Leu Lys Val Ala Gln His Leu Ala Tyr Pro Val Pro Asp
1               5                   10                  15
Val Pro
```

<210> SEQ ID NO 440
<211> LENGTH: 18
<212> TYPE: PRT
<213> ORGANISM: Hepatitis C virus

<400> SEQUENCE: 440

```
Leu Gly Phe Gln Pro Gly Leu Lys Val Ala Gln His Leu Ala Tyr Pro
1               5                   10                  15
Val Pro
```

<210> SEQ ID NO 441
<211> LENGTH: 18
<212> TYPE: PRT
<213> ORGANISM: Hepatitis C virus

<400> SEQUENCE: 441

```
Phe Gln Pro Gly Leu Lys Val Ala Gln His Leu Ala Tyr Pro Val Pro
1               5                   10                  15

Asp Val
```

<210> SEQ ID NO 442
<211> LENGTH: 18
<212> TYPE: PRT
<213> ORGANISM: Hepatitis C virus

<400> SEQUENCE: 442

```
Gly Phe Gln Pro Gly Leu Lys Val Ala Gln His Leu Ala Tyr Pro Val
1               5                   10                  15

Pro Asp
```

<210> SEQ ID NO 443
<211> LENGTH: 19
<212> TYPE: PRT
<213> ORGANISM: Hepatitis C virus

<400> SEQUENCE: 443

```
Phe Gln Pro Gly Leu Lys Val Ala Gln His Leu Ala Tyr Pro Val Pro
1               5                   10                  15

Asp Val Pro
```

<210> SEQ ID NO 444
<211> LENGTH: 19
<212> TYPE: PRT
<213> ORGANISM: Hepatitis C virus

<400> SEQUENCE: 444

```
Leu Gly Phe Gln Pro Gly Leu Lys Val Ala Gln His Leu Ala Tyr Pro
1               5                   10                  15

Val Pro Asp
```

<210> SEQ ID NO 445
<211> LENGTH: 19
<212> TYPE: PRT
<213> ORGANISM: Hepatitis C virus

<400> SEQUENCE: 445

```
Gly Phe Gln Pro Gly Leu Lys Val Ala Gln His Leu Ala Tyr Pro Val
1               5                   10                  15

Pro Asp Val
```

<210> SEQ ID NO 446
<211> LENGTH: 19
<212> TYPE: PRT
<213> ORGANISM: Hepatitis C virus

<400> SEQUENCE: 446

```
Glu Leu Gly Phe Gln Pro Gly Leu Lys Val Ala Gln His Leu Ala Tyr
1               5                   10                  15

Pro Val Pro
```

<210> SEQ ID NO 447
<211> LENGTH: 20
<212> TYPE: PRT
<213> ORGANISM: Hepatitis C virus

<400> SEQUENCE: 447

```
Leu Gly Phe Gln Pro Gly Leu Lys Val Ala Gln His Leu Ala Tyr Pro
```

```
1               5              10              15
Val Pro Asp Val
            20

<210> SEQ ID NO 448
<211> LENGTH: 20
<212> TYPE: PRT
<213> ORGANISM: Hepatitis C virus

<400> SEQUENCE: 448

Glu Leu Gly Phe Gln Pro Gly Leu Lys Val Ala Gln His Leu Ala Tyr
1               5                   10                  15

Pro Val Pro Asp
            20

<210> SEQ ID NO 449
<211> LENGTH: 20
<212> TYPE: PRT
<213> ORGANISM: Hepatitis C virus

<400> SEQUENCE: 449

Gly Phe Gln Pro Gly Leu Lys Val Ala Gln His Leu Ala Tyr Pro Val
1               5                   10                  15

Pro Asp Val Pro
            20

<210> SEQ ID NO 450
<211> LENGTH: 21
<212> TYPE: PRT
<213> ORGANISM: Hepatitis C virus

<400> SEQUENCE: 450

Glu Leu Gly Phe Gln Pro Gly Leu Lys Val Ala Gln His Leu Ala Tyr
1               5                   10                  15

Pro Val Pro Asp Val
            20

<210> SEQ ID NO 451
<211> LENGTH: 21
<212> TYPE: PRT
<213> ORGANISM: Hepatitis C virus

<400> SEQUENCE: 451

Leu Gly Phe Gln Pro Gly Leu Lys Val Ala Gln His Leu Ala Tyr Pro
1               5                   10                  15

Val Pro Asp Val Pro
            20

<210> SEQ ID NO 452
<211> LENGTH: 63
<212> TYPE: DNA
<213> ORGANISM: Artificial sequence
<220> FEATURE:
<223> OTHER INFORMATION: PCR primer

<400> SEQUENCE: 452
tccggctcct ggctaaggga cgactgggac tgggaatgcg aggtgctgag cgacgataag    60
acc                                                                  63

<210> SEQ ID NO 453
<211> LENGTH: 45
<212> TYPE: DNA
```

-continued

```
<213> ORGANISM: Artificial sequence
<220> FEATURE:
<223> OTHER INFORMATION: PCR primer

<400> SEQUENCE: 453
gattgggatt gggaatgcac ggtgttgact gatgacaaga cctgg         45

<210> SEQ ID NO 454
<211> LENGTH: 13
<212> TYPE: PRT
<213> ORGANISM: Hepatitis C virus

<400> SEQUENCE: 454

His Asp Ser Phe Ala Asn Ala Thr Gly Arg Phe Trp Pro
1               5                   10

<210> SEQ ID NO 455
<211> LENGTH: 13
<212> TYPE: PRT
<213> ORGANISM: Hepatitis C virus

<400> SEQUENCE: 455

Gln Gly Thr Ser Pro Ser Arg Leu Ala Val Pro Leu Ala
1               5                   10

<210> SEQ ID NO 456
<211> LENGTH: 13
<212> TYPE: PRT
<213> ORGANISM: Hepatitis C virus

<400> SEQUENCE: 456

Ile Ser Ser Lys Thr Gly Met Ser Ser Glu Pro Pro Ser
1               5                   10

<210> SEQ ID NO 457
<211> LENGTH: 13
<212> TYPE: PRT
<213> ORGANISM: Hepatitis C virus

<400> SEQUENCE: 457

Ile Leu Ser Ser Ile Asp Ala Leu Gly Ser Asp Ser His
1               5                   10

<210> SEQ ID NO 458
<211> LENGTH: 13
<212> TYPE: PRT
<213> ORGANISM: Hepatitis C virus

<400> SEQUENCE: 458

Leu Asp Asp Arg Ser Val Pro Thr Val Ile Ser Gln Arg
1               5                   10

<210> SEQ ID NO 459
<211> LENGTH: 13
<212> TYPE: PRT
<213> ORGANISM: Hepatitis C virus

<400> SEQUENCE: 459

Tyr Pro Ser Lys Pro Gly Asn Val Thr Pro Lys Ala Pro
1               5                   10

<210> SEQ ID NO 460
<211> LENGTH: 9
<212> TYPE: PRT
<213> ORGANISM: Hepatitis C virus
```

```
<400> SEQUENCE: 460

Gln Ala Gln Gly Glu Arg Ala Leu Lys
1               5

<210> SEQ ID NO 461
<211> LENGTH: 13
<212> TYPE: PRT
<213> ORGANISM: Hepatitis C virus

<400> SEQUENCE: 461

Thr Asp Lys Arg Ala Ser Pro Leu Thr Val Gln Ala Arg
1               5                   10

<210> SEQ ID NO 462
<211> LENGTH: 29
<212> TYPE: PRT
<213> ORGANISM: Hepatitis C virus

<400> SEQUENCE: 462

Tyr Ile Glu Gln Gly Met Met Leu Ala Glu Gln Phe Lys Gln Lys Ala
1               5                   10                  15

Leu Gly Leu Leu Gln Thr Ala Ser Arg His Ala Glu Val
            20                  25

<210> SEQ ID NO 463
<211> LENGTH: 17
<212> TYPE: PRT
<213> ORGANISM: Artificial sequence
<220> FEATURE:
<223> OTHER INFORMATION: Mutated version of non-structural protein NS5A

<400> SEQUENCE: 463

Leu Arg Asp Val Trp Asp Trp Ile Cys Thr Val Leu Thr Asp Phe Lys
1               5                   10                  15

Thr

<210> SEQ ID NO 464
<211> LENGTH: 10
<212> TYPE: PRT
<213> ORGANISM: Artificial sequence
<220> FEATURE:
<223> OTHER INFORMATION: Mutated version of non-structural protein NS5A

<400> SEQUENCE: 464

Leu Arg Asp Val Trp Asp Trp Ile Cys Thr
1               5                   10

<210> SEQ ID NO 465
<211> LENGTH: 12
<212> TYPE: PRT
<213> ORGANISM: Artificial sequence
<220> FEATURE:
<223> OTHER INFORMATION: Mutated version of non-structural protein NS5A

<400> SEQUENCE: 465

Asp Val Trp Asp Trp Ile Cys Thr Val Leu Thr Asp
1               5                   10

<210> SEQ ID NO 466
<211> LENGTH: 11
<212> TYPE: PRT
<213> ORGANISM: Artificial sequence
<220> FEATURE:
<223> OTHER INFORMATION: Mutated version of non-structural protein NS5A
```

-continued

```
<400> SEQUENCE: 466

Ser Trp Leu Arg Asp Val Trp Asp Trp Ile Cys
1               5                   10

<210> SEQ ID NO 467
<211> LENGTH: 27
<212> TYPE: PRT
<213> ORGANISM: Artificial sequence
<220> FEATURE:
<223> OTHER INFORMATION: Mutated version of non-structural protein NS5A
<220> FEATURE:
<221> NAME/KEY: MISC_FEATURE
<222> LOCATION: (4)..(4)
<223> OTHER INFORMATION: Xaa is W, A or F
<220> FEATURE:
<221> NAME/KEY: MISC_FEATURE
<222> LOCATION: (5)..(5)
<223> OTHER INFORMATION: Xaa is L, A, or K
<220> FEATURE:
<221> NAME/KEY: MISC_FEATURE
<222> LOCATION: (6)..(6)
<223> OTHER INFORMATION: Xaa is R, A, or N
<220> FEATURE:
<221> NAME/KEY: MISC_FEATURE
<222> LOCATION: (7)..(7)
<223> OTHER INFORMATION: Xaa is D, A, or S
<220> FEATURE:
<221> NAME/KEY: MISC_FEATURE
<222> LOCATION: (8)..(8)
<223> OTHER INFORMATION: Xaa is V, I, D, or S
<220> FEATURE:
<221> NAME/KEY: MISC_FEATURE
<222> LOCATION: (9)..(9)
<223> OTHER INFORMATION: Xaa is W, A, or F
<220> FEATURE:
<221> NAME/KEY: MISC_FEATURE
<222> LOCATION: (10)..(10)
<223> OTHER INFORMATION: Xaa is D, A, or S
<220> FEATURE:
<221> NAME/KEY: MISC_FEATURE
<222> LOCATION: (11)..(11)
<223> OTHER INFORMATION: Xaa is W, A, or F
<220> FEATURE:
<221> NAME/KEY: MISC_FEATURE
<222> LOCATION: (12)..(12)
<223> OTHER INFORMATION: Xaa is I, E, or L
<220> FEATURE:
<221> NAME/KEY: MISC_FEATURE
<222> LOCATION: (13)..(13)
<223> OTHER INFORMATION: Xaa is C, A, or S
<220> FEATURE:
<221> NAME/KEY: MISC_FEATURE
<222> LOCATION: (14)..(14)
<223> OTHER INFORMATION: Xaa is T, E, A, or W
<220> FEATURE:
<221> NAME/KEY: MISC_FEATURE
<222> LOCATION: (15)..(15)
<223> OTHER INFORMATION: Xaa is V, D, or S
<220> FEATURE:
<221> NAME/KEY: MISC_FEATURE
<222> LOCATION: (16)..(16)
<223> OTHER INFORMATION: Xaa is L, A, or K
<220> FEATURE:
<221> NAME/KEY: MISC_FEATURE
<222> LOCATION: (17)..(17)
<223> OTHER INFORMATION: Xaa is T, S, A, or W
<220> FEATURE:
<221> NAME/KEY: MISC_FEATURE
<222> LOCATION: (18)..(18)
<223> OTHER INFORMATION: Xaa is D, A, or S
<220> FEATURE:
<221> NAME/KEY: MISC_FEATURE
<222> LOCATION: (19)..(19)
<223> OTHER INFORMATION: Xaa is F, D, or L
<220> FEATURE:
<221> NAME/KEY: MISC_FEATURE
```

```
<222> LOCATION: (20)..(20)
<223> OTHER INFORMATION: Xaa is K, A, or L
<220> FEATURE:
<221> NAME/KEY: MISC_FEATURE
<222> LOCATION: (21)..(21)
<223> OTHER INFORMATION: Xaa is T, A, or W
<220> FEATURE:
<221> NAME/KEY: MISC_FEATURE
<222> LOCATION: (22)..(22)
<223> OTHER INFORMATION: Xaa is W, A, or F
<220> FEATURE:
<221> NAME/KEY: MISC_FEATURE
<222> LOCATION: (23)..(23)
<223> OTHER INFORMATION: Xaa is L, A, or K
<220> FEATURE:
<221> NAME/KEY: MISC_FEATURE
<222> LOCATION: (4)..(23)
<223> OTHER INFORMATION: In another embodiment Xaa at residues 4, 5, 7,
     9, 11, 13, 16, 18,
     19 or 23 may be D or Xaa ot residue 19 is A

<400> SEQUENCE: 467

Ser Gly Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Gln Ser Lys Leu
            20                  25

<210> SEQ ID NO 468
<211> LENGTH: 17
<212> TYPE: PRT
<213> ORGANISM: Artificial sequence
<220> FEATURE:
<223> OTHER INFORMATION: Mutated version of non-structural protein NS5A
<220> FEATURE:
<221> NAME/KEY: MISC_FEATURE
<222> LOCATION: (1)..(2)
<223> OTHER INFORMATION: if Xaa is present at these residues, Xaa at
     residue 1 is L and at
     residue 2 is R.
<220> FEATURE:
<221> NAME/KEY: MISC_FEATURE
<222> LOCATION: (11)..(17)
<223> OTHER INFORMATION: Xaa at these residues is optionally present
     when Xaa at residue
     1 & 2 are present.  When present, Xaa at residue 11 is V, at
     residue
     12 is L, at residue 13 is T, at residue 14 is D, at residue
     15 is F,
     at residue 16 is K, at residue 17 is T
<220> FEATURE:
<221> NAME/KEY: MISC_FEATURE
<222> LOCATION: (11)..(14)
<223> OTHER INFORMATION: When Xaa at residue 14 is present Xaa at
     residues (11) .. (13) is
     present also and Xaa at residue 14 is D, at residue 11 is V, at
     residue 12 is L, at residue 13 is T

<400> SEQUENCE: 468

Xaa Xaa Asp Val Trp Asp Trp Ile Cys Thr Xaa Xaa Xaa Xaa Xaa Xaa
1               5                   10                  15

Xaa

<210> SEQ ID NO 469
<211> LENGTH: 24
<212> TYPE: PRT
<213> ORGANISM: Hepatitis C virus

<400> SEQUENCE: 469

Trp Leu Arg Asp Ile Trp Asp Trp Ile Cys Glu Val Leu Cys Asp Phe
1               5                   10                  15

Lys Thr Trp Leu Lys Ala Lys Leu
```

-continued

```
            20

<210> SEQ ID NO 470
<211> LENGTH: 24
<212> TYPE: PRT
<213> ORGANISM: Hepatitis C virus

<400> SEQUENCE: 470

Trp Leu Arg Asp Asp Trp Asp Trp Glu Cys Glu Val Leu Ser Asp Asp
1               5                   10                  15

Lys Thr Trp Leu Lys Ala Lys Leu
            20
```

AGENTS FOR TREATMENT OF HCV AND METHODS OF USE

FIELD OF THE INVENTION

The invention relates generally to Hepatitis C virus (HCV) infection, and more specifically to interrupting the mechanism of infection by HCV and to methods to identify agents, which effect this interruption. The invention also relates to interfering with the ability of HCV components to bind with cellular membranes of an infected cell.

BACKGROUND

Hepatitis C virus (HCV) establishes a chronic infection in a high percentage of infected individuals and is associated with progressive liver pathology, including cirrhosis and hepatocellular carcinoma. Antiviral drugs such as interferon alpha and ribavarin have had limited success in controlling HCV infection. As a result, it has become the leading cause for liver transplantation in the U.S. The HCV polyprotein comprises, from the amino terminus to the carboxy terminus, the core protein (C), the envelope proteins (E1 and E2), p7, a membrane bound protein, whose function is unknown and the non-structural proteins (NS2, NS3, NS4A, NS4B, NS5A and NS5B) which are believed to be important for replication. C codes for the core nucleocapsid protein, E1 and E2 are envelope proteins that coat the virus, NS2, NS3 and NS4A are involved in proteolytic processing of the HCV polyprotein, and NS5B has RNA polymerase activity. The functions of NS4B and NS5A are unknown.

Hepatitis C virus is a significant cause of morbidity and mortality, infecting over 100,000,000 people worldwide. Annual HCV related costs in the United States are about $1 billion. Current therapies are clearly inadequate; the best available treatment at present is the combination of interferon and ribavirin, a treatment which is inconveniently lengthy as it typically lasts over one and a half years, difficult to tolerate in that most patients have flu-like symptoms, and extremely expensive as the cost is in the range of thousands of dollars annually. Not only does the present treatment have these disadvantages, but it is also not particularly effective.

Certain interactions of viral proteins with cell membranes have previously been described. For example, in poliovirus and Hepatitis A virus, the nonstructural protein 2C contains a membrane associating amphipathic helix (See Teterina, N. L., et al., *J. Virol.* (1997) 71:8962-8972 (poliovirus); and Kusov, Y. Y., et al., *Arch. Virol.* (1998) 143:931-944 (Hepatitis A). This membrane association appears to play a role in RNA synthesis in poliovirus (Paul, A. V., et al., *Virol.* (1994) 199:188-199). Replication complexes are localized on the host endoplasmic reticulum (ER) and Golgi in the case of poliovirus (Bienz, K., et al., *J. Virol.* (1992) 66:2740-2747), and infection with poliovirus induces rearrangements of membranes derived from host ER and Golgi (Schlegel, A., et al., *J. Virol.* (1996) 70:6576-6588).

It is also known that the Hepatitis C nonstructural 5A protein illustrated below is a potent transcriptional activator (Kato, N., et al., *J. Virol.* (1997) 71:8856-8859); that amino terminal deletion mutants of Hepatitis C virus nonstructural protein NS5A function as transcriptional activators in yeast (Tanimoto, A., et al., *Biochem. Biophys. Res. Commun.* (1997) 236:360-364); and that this nonstructural protein physically associates with p53 and regulates p21/Waf1 gene expression in a p53 dependent manner (Majumder, M., et al., *J. Virol.* (2001) 75:1401-1407).

It has also been reported that a number of positive strand RNA viruses, like HCV, replicate in association with cytoplasmic membranes, although the precise manner of such association and replication is not understood. See, for example, Lazarus, L. H., et al., *J. Gen. Virol.* (1974) 23:213-218 (foot and mouth disease); Bienz, K., et al., *Virol.* (1980) 100:390-399 (polio); Froshauer, S., et al., *J. Cell. Biol.* (1988) 107:2075-2086 (alphavirus); Chu, P. W., et al., *Arch. Virol.* (1992) 125:177-191 (Kunjin virus); Rice, C. M., in *Fields Virology*, Fields, B. N., et al., Ed. (1996) Lippincott-Raven Publications: Philadelphia, Pa., pages 931-959 (*Flaviviridae*).

It is also known that NS5A, the nonstructural Hepatitis C protein used for illustration below is associated with cell membranes (Selby, M. J., et al., *J. Gen. Virol.* (1993) 74:1103-1113; Hijikata, M., et al., *Proc. Natl. Acad. Sci. USA* (1993) 90:10773-10777; Moradpour, D., et al., *Hepatol.* (1998) 28:192-201). This protein, NS5A, also has been reported to interact with other host cell proteins such as PKR protein kinase (Gale, M. J. J., et al., *Virol.* (1997) 290:217-227) and a SNARE-like protein (Tu, H., et al., *Virol.* (1999) 263:30-41). NS5A has also been implicated in determining the response to interferon therapy in some groups of patients (Gale, M. J. J., et al., *Virol.*, supra); Enomoto, H., et al., *N. Engl. J. Med.* (1996) 334:77-81.

There exists a need in the art for compositions, including peptide therapeutics, and methods employing the same, to prevent or inhibit infections due to Hepatitis C Virus, including inhibiting replication and/or pathogenesis due to HCV, with minimal or no adverse side effects.

SUMMARY OF THE INVENTION

The present invention is based on the discovery that the presence of an amphipathic helix located near the N-terminus of certain nonstructural proteins of HCV is required to associate these proteins with the cellular membranes in the infected host. Three such HCV nonstructural proteins, NS4B, NS5A and NS5B are known to be associated with the host cellular membranes and thus participate in the replication of HCV, which is considered to occur in association with cytoplasmic membranes and thus are implicated in the participation of replication of HCV. These proteins contain at least one amphipathic helix of about 20-25 amino acids in the N-terminal region which, when disrupted, can result in failure of these proteins to properly associate with cellular membranes. The ability of candidate reagents to interfere with this binding can readily be assessed by linking the amphipathic helix to a label, such as a reporter protein, and assessing the effects of candidate agents on the position of the reporter in the cell. Such an assay can be conducted in cell culture, and thus can overcome one significant obstacle to discovery of additional treatments for Hepatitis C viral infection.

There is a plethora of alternative methods other than this straightforward approach to assess the ability of a candidate substance or protocol to disrupt the necessary binding between the relevant amphipathic helix and the cytoplasmic cellular membranes. These approaches will be described in greater detail below.

Thus, in one aspect, the invention is directed to a method to identify a compound or protocol which is useful in treating HCV infection, which method comprises assessing the ability of a candidate compound or protocol to disrupt the binding of a peptide comprising an amphipathic helix derived from a Hepatitis C nonstructural protein, in particular NS4B, NS5A or NS5B, to cellular membranes.

This can be done, for example, by simply assessing the binding of a candidate compound to said peptide, wherein a compound which binds said peptide is identified as an anti-HCV agent. Alternatively, the ability of a candidate compound to inhibit the binding of a peptide containing the amphipathic helix to a membrane preparation from eukaryotic cells can be evaluated. In these aspects, the assay can be carried out using straightforward laboratory procedures, not even involving cell culture.

Another alternative method to identify compounds that are effective anti-HCV agents comprises providing cells which contain an amphipathic helix derived from Hepatitis C viral nonstructural proteins NS4B, NS5A or NS5B coupled to a detectable label; treating one sample of said cells with the candidate compound or protocol and maintaining a sample of said cells in the absence of said candidate compound or protocol; comparing the location of the label in cells treated with said compound or protocol as compared to cells not treated with said compound or protocol, whereby when cells in the presence of the candidate compound or protocol show a different cellular distribution of label as compared to cells not treated with said compound or protocol, said compound or protocol is identified as an agent or protocol for treating HCV.

Alternatively, a compound or protocol can be identified as an anti-HCV agent by linking the amphipathic helix derived from the N-terminal region of certain HCV nonstructural proteins and a reporter or label and observing the behavior of the reporter intracellularly. This can be done directly as described above by observing the intracellular location of a reporter that is a simple label or can take advantage of secondary effects of the reporter. For example, as described below, disrupting the binding of the nonstructural protein NS5A with the cytoplasmic membrane by disrupting the amphipathic helix results in translocation of the nonstructural protein to the nucleus. Thus, if the reporter includes a nuclear localization signal, the disruption of interaction with the cytoplasmic membrane can be measured indirectly by assessing the effects of translocation of the helix and its reporter functions to the nucleus as will be described in further detail below.

In another aspect, the invention is directed to methods of treating HCV by administering to a subject in need of such treatment an agent or protocol identified by the methods described above or by an agent or protocol which disrupts the interaction of an amphipathic helix derived from HCV nonstructural proteins with cellular membranes or with an agent that binds to said helix. The invention is also directed to agents and protocols identified by the method of the invention. The nature of some of the agents and protocols which will disrupt the binding of these helices to cellular membranes is apparent without the necessity for carrying out the above-described assays. For example, one approach is to employ the amphipathic helix itself as a competitor for the helix as it exists in the infective agent. Thus, peptides having the amino acid sequence corresponding to the sequence in the helices of the various HCV nonstructural proteins can be used as pharmaceuticals to compete with the helices contained in the nonstructural proteins themselves. In addition, molecules which mimic the pattern of hydrophilic or hydrophobic faces of the helix can be employed. Peptides which contain non-amide bonds but which retain the same essential backbone shape could also be used, as could aptamers which assemble to obtain the essential features of the helix. It may be possible by ascertaining the three-dimensional structure of the helix, the appropriate antibodies, or aptamers to design rationally organic molecules that assume the same charge/spatial configuration. Thus, the invention also includes these embodiments.

In another aspect, the invention is directed to a peptide of not more than about 60 amino acid residues, which is an HCV nonstructural protein amphipathic helix, where the peptide optionally contains non-peptide isosteric linkages, and where the peptide is optionally coupled to an additional heterologous second peptide or to an additional component.

In yet another aspect, the invention provides an isolated peptide that interferes with the binding of an amphipathic helix derived from HCV nonstructural proteins with cellular membranes.

In still another aspect, the invention provides a peptide that inhibits the association of an amphipathic helix present in the N-terminus of an HCV nonstructural protein with cytoplasmic membranes of a cell and having an amino acid sequence SGSWLRDVWDWICTVLTDFKTWLQSKL (SEQ ID NO: 14), and variants and mutants thereof, and wherein the peptide is identified by assessing the ability of the peptide to interfere with the binding of an amphipathic helix present in the N-terminus of an HCV nonstructural protein with cytoplasmic membranes of a eukaryotic cell, where a peptide which interferes with binding is identified as useful in treating HCV infection.

In yet another aspect, the invention provides a method of screening for a peptide useful as an inhibitor of the binding of an HCV nonstructural protein with cytoplasmic membranes of a eukaryotic cell by contacting an amphipathic helix present in the N-terminus of an HCV nonstructural protein with cytoplasmic membranes of a eukaryotic cell, both in the presence and absence of a test compound, wherein a decreased level of binding in the presence of the compound as compared to the level in the absence is indicative of a peptide inhibitor.

In another embodiment, the invention provides an isolated peptide selected from complementary peptides or competitive inhibitors, functional fragments, mutants or variants thereof, wherein the isolated peptide causes inhibition of infection, replication, or pathogenesis of Hepatitis C Virus in vitro or in vivo when introduced into a host cell containing said virus, and wherein said isolated peptide exhibits an $IC_{50}$ in the range of from about 0.0001 nM to about 100 μM in an in vitro assay for at least one step in infection, replication, or pathogenesis of said virus.

In yet another embodiment, the invention provides a composition of one or more isolated peptides of the invention, functional fragments, mutants or variants thereof, and a carrier, a diluent, an excipient or a buffer.

In still another embodiment, the invention provides a pharmaceutical composition of one or more isolated peptides of the invention, functional fragments, mutants or variants thereof, and a pharmaceutically acceptable carrier, diluent, excipient, or buffer.

In another embodiment, the invention provides a method of preventing or treating HCV infection in a patient in need thereof, comprising administering to said patient an anti-HCV effective amount of an isolated peptide of the invention, functional fragments, mutants or variants thereof.

In another embodiment, the invention provides use of an isolated peptide selected from the peptide of the invention, functional fragments, mutants or variants thereof in the preparation of a medicament for the prevention or treatment of HCV infection in a human patient in need thereof.

In yet another embodiment, the invention provides a method of treatment of HCV infection in a patient in need thereof, comprising administering to said patient an anti- HCV effective amount of an isolated peptide of the invention, comprising the NS5A amphipathic helix of a functional fragment thereof.

BRIEF DESCRIPTION OF THE DRAWINGS

FIG. 1 shows amino acid sequences (SEQ ID NOS:1-13) which comprise amphipathic helices in the N-terminal region of NS4B, NS5A and NS5B of Hepatitis C virus genotype 1a. Helices of NS5A from a variety of isolates are particularly exemplified.

FIGS. 2A-2J show the helical conformation of sequences in the various isolates of NS5A (SEQ ID NOS: 469 and 5-13, respectively).

FIGS. 3A-3C, upper two panels, show the effect of the alterations to the helical structure on the cellular distribution pattern of NS5A. FIG. 3A shows the pattern obtained when the helix is not disrupted; FIGS. 3B and 3C show the patterns obtained when the helix is deleted or the hydrophobic face is disrupted.

FIG. 4B shows the localization pattern of the fusion protein of the helix with GFP; FIG. 4A shows the pattern for GFP alone, and FIG. 4C shows the pattern obtained when the hydrophobic face of the helix is disrupted.

FIGS. 5A and 5B, lower panels, show the results of these assays.

FIGS. 6A-6C show the results of a membrane floatation assay for binding of the NS5A amphipathic helix with microsomal membrane.

DETAILED DESCRIPTION OF THE INVENTION

Figure 3A:
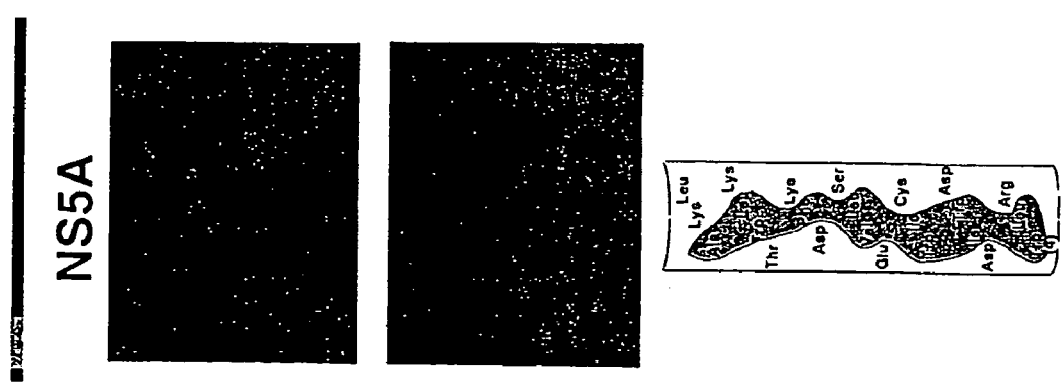
FIGS. 3A-3C, lower panels, show the conformation of amino acid sequences in positions 4-27 of NS5A which form the N-terminal helix in the native protein (FIG. 3A; SEQ ID NO:297) but wherein the helical structure is deleted (FIG. 3B; SEQ ID NO: 297) or wherein the hydrophobic region is interrupted (FIG. 3C; SEQ ID NO: 470).

The Hepatitis C virus has been well studied and the genome has been completely sequenced. The genome of HCV is a single-stranded RNA of 9.6 kb that encodes a single approximately 3,010 amino acid polyprotein. This polyprotein is proteolytically processed into structural proteins and nonstructural proteins. HCV, like other positive strand RNA viruses, is thought to replicate in association with cytoplasmic membranes; and the approximately 447 amino acid nonstructural protein, NS5A is known to associate with host cell membranes. This protein is thus believed to play a key role in replication. The discovery of alternative treatments has been hampered by the lack of a cell culture model for HCV. The present invention overcomes this problem, and provides a convenient assay for identifying agents that can directly and specifically curtail the course of HCV infection. As noted above, the present invention resides in the discovery of a mechanism to disrupt association between certain nonstructural proteins of the virus and cytoplasmic membranes.

Administration of peptides and proteins intracellularly has been limited by the lack of consistent and efficient uptake across the cell membrane. However, various membrane translocation sequences (MTS) have been identified which allow the transduction of peptides across the plasma membrane (for example, References 10, 13, 14, 16, 17, 20, 21 and 22). While unknown, it is hypothesized that the mechanism of the transduction is that an MTS is able to transport both peptides and full-length proteins into the cytoplasm of cells. It is believed that the separate peptides form a noncovalent complex in solution that is then transported into the cell.

It has now been found that an amphipathic helix consisting of about 20-25 amino acids is critical to the association of NS5A with cytoplasmic membranes, for example endoplasmic reticulum (ER), as are similar helices found in NS4B and NS5B. As shown below, when the amphipathic nature of the helix is disrupted, NS5A no longer associates with cell membranes; in addition, the helix when coupled to other substances, including other proteins, effects association of the carried component to the cell's cytoplasmic membranes. As used herein, "cytoplasmic membrane" refers to a structure contained in the cellular cytoplasm, which can generally be recognized as a membrane structure for example, membranes of the endoplasmic reticulum (ER). The membranes may include protein receptors or other elements in addition to the more hydrophobic portions of the membrane per se which may account at least in part for the association of the amphipathic helix to the "cytoplasmic membrane". No theory is advanced as to the mechanism whereby the amphipathic helix associates itself with the cytoplasmic membrane, and thus the precise elements contained in the membrane, which are responsible for this association, are not defined. The observations related to the screening methods described below are not dependent on any definition: intracellular embodiments of these assays rely on direct observation of the cellular distribution of the helix and its label and studies which involve membrane preparations ex vivo employ compositions of cytoplasmic membranes as conventionally prepared, without regard to substructure. This amphipathic helix feature is found in nonstructural proteins of isolates of many strains of HCV of various geographical origins. It is also demonstrated below that disruption of the amphipathic nature of the helix of NS5A prevents replication of HCV RNA.

FIG. 1 shows the amino acid sequences of the amphipathic helices that have been found near to the N-terminus of three nonstructural proteins from prototype genotype 1a representing amino acids 7-34 of NS4B (SEQ ID NO: 1), amino acids 5-26 of NS5A (SEQ ID NO: 2), and two amphipathic helical regions of NS5B, amino acids 65-87 (SEQ ID NO: 3) and 107-125 (SEQ ID NO: 4). This figure also shows the relevant sequences in NS5A for additional genotypes 1b (acc. No. P26663) (SEQ ID NO: 5); 2a (acc. No. P26660) (SEQ ID NO: 6); 2b (acc. No. AB030907) (SEQ ID NO: 7); 3a-K (acc. No. D28917) (SEQ ID NO: 8); 3a-NZL (acc. No. D17763) (SEQ ID NO: 9); 3b (acc. No. D49374) (SEQ ID NO: 10); 4a (acc. No. Y11604) (SEQ ID NO: 11); 10a (acc. No. D63821) (SEQ ID NO: 12); and 11a (acc. No. D63822) (SEQ ID NO: 13). The sequences listed in FIG. 1 are not an exhaustive list of the amino acid sequences of amphipathic helices of these three nonstructural proteins. NS4B and NS5B may be expanded similarly to NS4A in FIG. 1. Although the sequences per se are not completely homologous, they are all capable of forming amphipathic helices. (See FIGS. 2A-2J which show these helices from the NS5A proteins.) Thus, it is clear that the presence of the N-terminal amphipathic helix, containing a sequence of approximately 20-25 amino acids is widespread in the nonstructural proteins of HCV and in various isolates.

As used herein, the term "HCV nonstructural protein amphipathic helix" refers to a sequence of at least 15 amino acids, preferably at least 20 amino acids and preferably not more than 30, more preferably not more than 25 amino acids which has the amino acid sequence selected from the group consisting of those set forth in FIG. 1, or which is at least 80% homologous, preferably at least 90% homologous and more preferably at least 95% homologous to at least one of said sequences and which retains the ability to form an amphipathic helix. While it is known that certain amino acid substitutions will result in peptides, which, while they retain the required degree of homology (sequence identity), will disrupt the formation of the helix, the nature of these substitutions is already understood by those of ordinary skill and can be avoided, or purposefully used, as desired. Insertion of, for example, disruptive proline residues, is understood to be undesirable. Thus, it is well within ordinary skill to substitute one or more amino acids in these sequences to obtain substitute helices with the required degree or homology, avoiding unsuccessful substitutions.

It should be noted that in certain embodiments of the invention, the amphipathic helix may be other than a peptide; for example, it may constitute a pseudopeptide where the native peptide linkages are substituted by isosteres as is understood in the art. Similarly, alternative polymeric structures can be designed which mimic the charge and shape distribution of these amphipathic helices and mutants and variants thereof. These homologs and analogs are included within the scope of the invention and are useful both in therapeutic protocols and in assay systems for ascertaining alternative compounds and protocols which will be useful in treating HCV infection.

As used herein, the term "amino acid" is applicable not only to cell membrane-permeant peptides, but also to amphipathic helices and anti-HCV peptides useful as pharmaceutical agents, i.e., all the individual components of the present compositions.

The term "amino acid" is used herein in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, β-alanine, ornithine, etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

The incorporation of non-natural amino acids, including synthetic non-native amino acids, substituted amino acids, or one or more D-amino acids into the present anti-HCV peptides of the present invention is advantageous in a number of different ways. D-amino acid-containing peptides exhibit increased stability in vitro or in vivo compared to L-amino acid-containing counterparts. Thus, the construction of peptides incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. When it is desirable to allow the peptide, etc., to remain active for only a short period of time, the use of L-amino acids therein will permit endogenous peptidases, proteases, etc., in a cell to digest the molecule in vivo, thereby limiting the cell's exposure to the molecule. Additionally, D-peptides, etc., cannot be processed efficiently for major histocompatibility complex class II-restricted presentation to T helper cells, and are therefore less likely to induce humoral immune responses in the whole organism.

One factor that can be considered in making such changes is the hydropathic index of amino acids. The importance of the hydropathic amino acid index in conferring interactive biological function on a protein has been discussed by Kyte and Doolittle (1982, *J. Mol. Biol.*, 157: 105-132). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide, polypeptide, or protein can be substituted for other amino acids having a similar hydropathic index or score and produce a resultant peptide, etc., having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101, herein incorporated by reference, discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant peptide, etc., having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the anti-HCV peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine.

It should be noted that changes which are not expected to be advantageous can also be useful if these result in the production of functional sequences. Since small peptides, etc., can be easily produced by conventional solid phase synthetic techniques, the present invention includes peptides, etc., such as those discussed herein, containing the amino acid modifications discussed above, alone or in various combinations. To the extent that such modifications can be made while substantially retaining the activity of the peptide, they are included within the scope of the present invention. The utility of such modified peptides, etc., can be determined without undue experimentation by, for example, the methods described herein.

Based on the present discoveries, various methods to identify agents and protocols which would be effective in treating HCV are made possible. In their simplest form, since binding between the helix and the cytoplasmic membrane is a necessary condition for association of the nonstructural protein with the membrane and is required for the virus to replicate, compounds which simply bind the helix compete with the cellular membranes for this association. When the helix is contained in a substantially larger molecule, such as existing in the context of a significantly longer amino acid sequence, it is possible that the remaining portion of the molecule or amino acid sequence may itself contain elements that are capable of affecting binding. Thus, in the assays of the invention, appropriate controls may be required to ensure that it is the interaction of the helix with the compounds tested or the membranes tested that is being measured. Compounds that bind to the helix would inhibit the required cellular binding, and by identifying compounds that bind with high affinity to the helix compounds that would be successful in interfering with the binding will be found. By "high affinity" is meant binding with a dissociation constant of $<10^{-4}$, preferably $<10^{-6}$, and more preferably $<10^{-8}$. Dissociation constants can be determined using methods generally known in the art; for example the helix could be bound to solid support and labeled compound at varying concentrations supplied wherein the amount of label coupled to solid support can be readily determined.

Alternatively, the peptide comprising the helix can be displayed using standard phage display techniques and the phage tested for ability to bind to compounds that are coupled to solid supports. Phage display is also utilized to screen random peptides to screen for competitive inhibitors of the amphipathic helix. Such peptides would block virus from binding to the receptor.

There are a variety of techniques well known in the art for assessing binding of compounds to targets. A wide variety of detectable labels can be used, and the assays can be conducted in heterogeneous or homogeneous formats. For example, the compound itself can be labeled for detection of its ability to transport label to solid support, to which solid support has been bound the amphipathic helix or, vice versa, the amphipathic helix can be labeled and the compound to be tested can be coupled to solid support. The assay can also be conducted in a homogeneous format using fluorescence techniques, for example, where the fluorescence of a fluorescent label attached to the compound is altered by virtue of its binding to a peptide the size of the amphipathic helix or larger.

The amphipathic helix itself can be supplied in the context of the nonstructural protein or fragment thereof or can be supplied per se or as a fusion protein that contains a label, such as green fluorescent protein.

In a variation of this extracellular format, the effect of individual compounds or mixtures of compounds on the binding of the amphipathic helix or a protein containing it with a membrane preparation can be evaluated. Techniques similar to those described above may be used—e.g., the membrane preparation may be labeled and the amphipathic helix or protein containing it coupled to solid support or displayed using phage. The coupling of the label to solid support containing the helix or relevant protein or to the phage displayed helix in the presence and absence of compound or mixtures of compounds can be determined. These assays can be conducted in homogeneous format by using fluorescence labeling, for example, of the amphipathic helix. A wide variety of such protocols is known in the art, and the essential feature is determination of the effect of the compound or a mixture of compounds on the binding of the amphipathic helix or a protein containing it and the membrane preparation. Perhaps a particularly convenient embodiment of this method would involve a fusion between the amphipathic helix and green fluorescent protein which could be produced very conveniently using recombinant techniques; assessment of the binding of this fusion to the membrane preparation either in a heterogeneous or homogeneous format can then be performed.

As further described below, in Example 3, an assay for binding of the amphipathic helix to the microsomal membrane can be performed by treating a microsomal or cytoplasmic membrane preparation in vitro with a peptide containing the helix and distributing the contents of the reaction mixture in a sedimentation gradient. The helix coupled to membrane will reside in a relatively low density portion of the gradient and is thus separated from mere debris that is found at the bottom of the gradient. The floated helix can be detected in the appropriate gradient fraction using polyacrylamide gel electrophoresis. The helix may be labeled for example, with a radioisotope or a coupled fluorescent label such as green fluorescent protein used in a fusion. This assay can be used to screen for compounds or protocols that disrupt binding to the microsomal membrane by conducting the assay in the presence and absence of the protocols or compounds and comparing the results.

In addition to the above-described methods that can be conducted extracellularly, the effect of various protocols and compounds or mixtures of compounds on the behavior in terms of binding to cytoplasmic membranes of the relevant amphipathic helix can be determined in a variety of intracellular assays. Any eukaryotic cells may be used, but typically and most conveniently, mammalian cells or yeast cells are used in these assays.

Intracellular assays can be performed by generating desired peptide constructs intracellularly from recombinant expression systems. Alternatively, the assays can be conducted by first preparing the labeled amphipathic helix or protein containing said helix and introducing the derivatized helix into the cells using cell-penetrating peptides. The compounds to be tested may be introduced in the same manner. Such cell-penetrating peptides are described, for example, in a review article by Lindgrin, M., et al., in *TiPS* (2000) 21:99-103, the contents of which are incorporated herein by reference to describe an exemplary list of such cell-penetrating peptides. These peptides can be coupled to any substance to facilitate the entry of said substance into a eukaryotic cell.

In another embodiment, MTS is able to transport both peptides and full-length proteins into the cytoplasm of cells with or without covalent linkage or crosslinking. (For example, Reference 14.) It is believed that the separate peptides form a noncovalent complex in solution that is then transported into the cell. In one embodiment, the peptides are NS4B or NS5A.

The ability to deliver peptides and proteins into the intracellular milieu for investigational studies or therapeutic applications has previously been limited by the lack of consistent and efficient uptake across the cell membrane. However, a number of reports in the last couple of years have identified various membrane translocation sequences (For example, see references 10, 13, 14, 16, 17, 20, 21, 22) that allow the transduction of peptides across the plasma membrane. The mechanism of transduction is not yet clear, but it has been shown that it is not due to receptor-mediated uptake, or in conjunction with a known transport mechanism. In the initial reports, the MTS was covalently linked to the peptide or protein that was to be delivered into the cell, but recently an MTS was identified that was able to transport both peptides and full-length proteins into the cytoplasm of cells in the absence of covalent linkage or crosslinking (14). Apparently, the separate peptides form a noncovalent complex in solution that is then transported into the cell.

In the most direct forms of such assays, the change in intracellular distribution of the labeled amphipathic helix either supplied per se or in the context of a larger protein can be determined. A wide variety of labels can be used; perhaps the most convenient is a fusion with green fluorescent protein, or simple coupling of the amphipathic helix or the protein containing it to a detectable fluorescent label. The location of the labeled helix or protein containing it can then be observed by a variety of methods including direct observation and histological techniques. Thus, in one example, the effect of a candidate compound or protocol directly on the ability of the helix to bind to cellular membranes can be assessed by coupling the helix to a reporter which is detectable; most convenient are labels which are fusion proteins formed with the helix, such as green fluorescent protein. The intracellular locations of the reporter in the presence and absence of the candidate protocol compound can then be compared. The corresponding labeled helix, which has been mutated to disrupt the amphipathic helical conformation, can conveniently be used as a control. Compounds or protocols that are able to disrupt the binding of the helix with the membrane can readily be identified when their presence results in less label associated with cell membranes.

If histological techniques are used, the label can be less direct; for example, the helix might be fused to a protein that can be detected with a labeled antibody or may be fused to an enzyme that can be detected in the presence of a substrate. Once the cells are fixed histologically, the supplementary reagents can be added for detection.

Another embodiment of this uses cells harboring a vector or plasmid expression NS5A or HCV replicon with a wild-type amphipathic helix in NS5A. The cells are exposed to a control or candidate inhibitor. At the end of the assay, the cells are fixed and stained for NS5A by indirect immunofluorescence. A compound is deemed inhibitory if it alters the normal membrane associated staining of NS5A.

Test compounds that appear to interrupt the ability of the amphipathic helix to bind to the cellular membranes, or which are shown to disrupt the normal binding pattern of the amphipathic helix can be confirmed as anti-HCV agents in a standard colony formation assay. In this assay, an HCV replicon is supplied with a drug resistance marker, such as neomycin resistance. When neomycin-sensitive cells are infected with the replicon and grown on neomycin-containing medium or G418, for example, only cells wherein replication can occur will be able to form colonies. The diagnostic replicon can be used to infect neomycin-sensitive cells in the presence and absence of the compound that has been shown to disrupt the amphipathic helix/membrane binding, and such compounds result in destroying or decreasing the ability of the infected cells to form colonies. Alternatively, RNA replicon levels can be measured to identify the effect of the compound.

When intracellular formats are used, in addition to testing compounds and mixtures of compounds, as noted above, it is possible to test the effect of protocols which involve various regimes of treatment, including, in addition to providing compounds, various antisense techniques, and various forms of environmental stress such as pH changes, temperature changes, mechanical disturbances and the like.

In addition to the foregoing, somewhat more sophisticated methods to assess the impact of compounds and protocols on the intracellular location of substances containing the amphipathic helices derived from Hepatitis C nonstructural proteins can be employed. For example, it is demonstrated below that disruption of the amphipathic helix in NS5A, in addition to causing the protein to fail to associate with cytoplasmic membranes, directs this protein to the nucleus. Therefore, the assay methods can include features in the substance containing the amphipathic helix that act as nuclear localization signals (NLS), many of which are well known in the art. Under these conditions the label can constitute a functionality which exerts its effect in the nucleus, and the disruption of binding of the amphipathic helix with the cytoplasmic membrane can be detected by a reporter function associated with the helix which exerts its effects in the nucleus. Such effects would be, for example, enhancement or repression of the expression of a detectable protein; this would involve including transactivators, transcription factors, or repressors in the construct containing the helix and the NLS. Of course, the nuclear localization signal—derived constructs can also be detected in the nucleus directly, using a direct detectable label of the sort described above—e.g., GFP, a partner in an antibody/antigen interaction, or an enzymatic activity, or a radiolabel.

For example, in one preferred format, the amphipathic helix or a larger protein comprising said helix is coupled to a nuclear localization signal and to a transactivator. The host cell is modified to contain an expression system for a detectable protein, for example, green fluorescent protein in its genome. The transactivator then can effect the expression of the green fluorescent protein under conditions wherein the protocol or compound to be tested disrupts the binding of the amphipathic helix with the cytoplasmic membrane, thus permitting the nuclear localization signal to transport the construct to the nucleus where the transactivator can effect expression of the GFP. Alternative proteins whose expression can be detected are those, such as GFP, that are detectable per se or may be detectable by virtue of their effects on cellular growth, such as his3, leu2, β-galactosidase, β-glucoronidase, SV40T antigen, chloramphenicol acetyl transferase (CAT), hygromycin B phosphotransferase, SEAP or cell surface antigens such as CD4. In addition to transactivators, transcription factors which enhance expression include derivatives of lexa, cI, or gal4 DNA binding domains fused to activation domains of B42, VP16 and the like.

Again, the essential feature is the detection of the effect of the proposed protocol, compounds or mixtures of compounds on the interaction of the amphipathic helix, whether supplied per se or in the context of a larger protein, with the cytoplasmic membranes. The foregoing suggested assay formats are merely exemplary and a wide variety of such formats will be apparent to one of skill in the art. Any such assay method is appropriate; the design of such assays and forms of label draws on a wide literature available to the practitioner.

By conducting the foregoing assays, compounds and/or protocols are identified which will be effective in treating HCV infection. By "treating" is meant both therapeutic and prophylactic treatment, and refers to a desirable effect on viral load, or symptomology, or any desirable outcome which mitigates the negative consequences of the typical progress of HCV infection. The term "treat" is not to be construed to imply absolute cure or absolute prevention. Any helpful amelioration or repression of the infection is sufficient to meet this definition.

Compounds thus identified can be administered in conventional ways using standard pharmaceutical formulations such as those set forth in *Remington's Pharmaceutical Sciences*, latest edition, Mack Publishing Co., Easton, Pa., incorporated herein by reference. (See also, References 23-33.) Various enteral or parenteral routes of administration may be used, including administering by injection, such as intravenous, intramuscular, subcutaneous and the like, or by oral administration or by suppository. In addition, sustained release compositions can also be used.

The terms "an effective amount," "an anti-HCV effective amount," or a "pharmaceutically effective amount" of a peptide of the present invention as applied to such molecules refers to an amount of a peptide, or combination of two or more peptides as disclosed herein, effective in reducing or ameliorating conditions, symptoms, or disorders associated with HCV infection or associated pathogenesis in patients, and/or in reducing viral levels in vitro or in vivo.

Effective amounts of peptides for the treatment or prevention of HCV infections, delivery vehicles containing peptides or constructs encoding the same, agonists, and treatment protocols, can be determined by conventional means. For example, the medical practitioner can commence treatment with a low dose of one or more peptides in a subject or patient in need thereof, and then increase the dosage, or systematically vary the dosage regimen, monitor the effects thereof on the patient or subject, and adjust the dosage or treatment regimen to maximize the desired therapeutic effect. Further discussion of optimization of dosage and treatment regimens can be found in Benet et al., in *Goodman & Gilman's The Pharmacological Basis of Therapeutics*, Ninth Edition, Hardman et al., Eds., McGraw-Hill, New York, (1996), Chapter 1, pp. 3-27, and L. A. Bauer, in *Pharmacotherapy, A Pathophysiologic Approach*, Fourth Edition, DiPiro et al., Eds., Appleton & Lange, Stamford, Conn., (1999), Chapter 3, pp. 21-43, and the references cited therein, to which the reader is referred.

The dosage levels and mode of administration will be dependent on the nature of the compound identified and the particular situation of the subject. Optimization of routes of administration, dosage levels, and adjustment of protocols, including monitoring systems to assess effectiveness of the treatment are routine matters well within ordinary skill. Protocols which are identified using the intracellular assays set forth above must, of course, be modified in the context of treatment of subjects, and this, too, falls within the skill of the practitioner.

Typically, the compounds that are identified by the methods of the invention will be "small molecules"—i.e., synthetic organic structures typical of pharmaceuticals. Examples of such "small molecules" are found, for example, in the *Physicians' Desk Reference* (with respect to approved drugs), the *Merck Index*, and the *U.S. Pharmacopoeia*. However, such compounds may also include peptides, peptidomimetics, nucleic acids, peptide nucleic acids, carbohydrates, lipids, and the like. As noted above, the HCV nonstructural protein amphipathic helix used in these assays may be the native helix, both alone and in the context of a larger protein and the assays may also utilize a homologous form of the helix included within the definition above which retains the spatial and charge configuration of the native form.

In addition to compounds identified by means of the foregoing assays, protocols and substances useful in treating HCV infection can be formulated and utilized a priori. For example, the helix itself, or a functional fragment thereof can readily be used in treatment by virtue of its ability to bind the helix as it resides in an HCV non-structural protein itself or to compete with the helix as it resides in an HCV non-structural protein itself for sites on the cytoplasmic membrane to which the helix will bind. Thus, formulations of the HCV nonstructural protein amphipathic helix or functional fragment thereof can be used directly to treat HCV infection. Typically, these formulations will contain peptides bearing the helix of less than 60 amino acids, in another embodiment less than 50 amino acids, in another embodiment less than 30 amino acids, and, in yet another embodiment less than 25 amino acids in another embodiment, not be less than 4 amino acids, and may, in addition to the peptide region bearing the helix, further contain components to enhance membrane penetration. The peptides comprising the helix may be as short as 10-15 amino acids, 6-9 amino acids or 4-6 amino acids, so long as functionality in terms of competitive binding, or inhibition of binding, is retained. Methods to synthesize such peptides are, of course, well known, both direct and recombinant methods may be used. Thus, a peptide useful in the method of the invention as to its helix-based antiviral activity will typically contain from about 4 to 60 amino acids, and certainly far less than the several hundred amino acids contained in the native viral protein from which it can be derived. This relatively short peptide may optionally be coupled to additional sequence either for labeling, or, more typically, for conferring the ability to enter cells. Such membrane penetration facilitators are known, for example, the HIV-tat peptide or MTSs described herein, are able to introduce non-native proteins into cells. The peptides to be administered will thus contain a portion comprising the amphipathic helix and a heterologous portion for facilitating cellular entry. Entry can also be facilitated by liposomes or cationic polymers, for example. However, wild type NS5A is able to cross the membrane without the assistance of a facilitator. Wild type NS5A is capable of entering the cell without any previously described MTS peptide or other facilitator.

As used herein "functional" refers to a protein, peptide, helix or antibody, or fragment thereof, which possesses the ability to inhibit the binding of a nonstructural HCV protein, for example, NS4B or NS5A, to a cell membrane.

The peptides useful in the methods of the invention can also be generated in the subject to be treated by virtue of administering expression systems for those peptides consisting entirely of gene-encoded amino acids. These expression systems may be introduced as naked DNA, as expression vectors suitable for transfection of mammalian cells, or preferably using adenoviral or retroviral or other suitable viral vectors.

As described above, however, these competitor peptides need not be the native sequences per se and need not even be peptides per se, but may contain isosteric linkages or other polymeric features that result in similar charge/shape features as compared to the native helices.

Peptides, or compounds with similar charge/shape features and having the activity of the peptides described herein, can be identified by phage display using wild-type amphipathic helix and a mutant amphipathic helix peptides as positive and negative selectors, respectively.

The compositions or agents of the invention may comprise, consist essentially of, or consist of the peptide sequences disclosed herein. The phrase "consists essentially of or consisting essentially of" or the like, when applied to anti-HCV peptides encompassed by the present invention refers to peptide sequences like those disclosed herein, but which contain additional amino acids (or analogs or derivatives thereof as discussed above). Such additional amino acids, etc., however, do not materially affect the basic and novel characteristic(s) of these peptides in modulating, attenuating, or inhibiting HCV infection, replication, and/or pathogenesis, including the specific quantitative effects of these peptides, compared to those of the corresponding peptides disclosed herein.

In one approach, the agent may be a transdominant inhibitor of the membrane association function whereby forms of the amphipathic helix that interfere with the ability of the helix to form oligomers can be used. Thus, by generating or providing a mutant form of the helix containing one or more amino acid substitutions, this form may associate with the native helix to provide an inactive form or rendering it unable to dimerize or oligomerize with additional native forms. In one approach, the decoy peptide is mutated to convert hydrophobic amino acids to hydrophilic ones thus destroying the hydrophobic face of the helix. For example, mutated versions of the peptide sequence for NS5A strains would include

```
SGSWLRDDWDWECEVLSDDKTWLKAK     (SEQ ID NO: 15)
or
SGSWLRDDWDWECTVLTDDKTWLQSKL.   (SEQ ID NO: 16)
```

SEQ ID NOS:15 and 16 are used as PEP2 in Example 4, below.

In another approach, the agent is a competitive inhibitor of the amphipathic helix. These competitive inhibitors may interrupt the binding between the helix and the membrane, achieving the desired effect. Such inhibitors may be fragments of the wild type sequence of the amphipathic sequence or variants or mutants thereof. Fragments of the HCV nonstructural proteins that may be used as competitive inhibitors may include, but are not limited to:

```
                                         (SEQ ID NO: 462)
YIEQGMMLAEQFKQKALGLLQTASRHAEV, (NS4B 6-34)

(SEQ ID NO: 3)
QDVLKEVKAAASKVKANLLSVEE, (NS5B 65-87)
and
                                         (SEQ ID NO: 4)
DVRCHARKAVAHINSVWKD. (NS5B 107-125)
```

Another competitive inhibitor of NS5A would include: SGSWLRDVWDWICTVLTDFKTWLQSKL (SEQ ID NO:14) and variants and mutants thereof. Variants and mutants of this peptide would include a peptide with one or more of the following amino acid substitutions: substitute of L at amino acid 16 by A or K; or substitution of the T at amino acid 17 by A; or substitution of the D at amino acid 18 by A; or substitution of the F at amino acid 19 by A; or substitution of the K at amino acid 20 by A; or substitution of the W at amino acid 22 by A; or substitution of the L at amino acid 23 by K, and derivatives thereof. Another such mutant of HS5A is: SGSX$_1$X$_2$X$_3$X$_4$X$_5$X$_6$X$_7$X$_8$X$_9$X$_{10}$X$_{11}$X$_{12}$X$_{13}$X$_{14}$X$_{15}$X$_{16}$X$_{17}$X$_{18}$X$_{19}$X$_{20}$QSK L (SEQ ID NO: 467), where X$_1$ is W, A or F; X$_2$ is L, A or K; X$_3$ is R, A or N; X$_4$ is D, A or S; X$_5$ is V, I, D or S; X$_6$ is W, A or F; X$_7$ is D, A or S; X$_8$ is W, A or F; X$_9$ is I, E or L; X$_{10}$ is C, A or S; X$_{11}$ is T, E, A or W; X$_{12}$ is V, D or S; X$_{13}$ is L, A or K; X$_{14}$ is T, S, A or W; X$_{15}$ is D, A or S; X$_{16}$ is F, D, or L; X$_{17}$ is K, A or L; X$_{18}$ is T, A or W; X$_{19}$ is W, A or F; and X$_{20}$ is L, A or K. In another embodiment, X$_1$, X$_2$, X$_4$, X$_6$, X$_8$, X$_{10}$, X$_{13}$, X$_{15}$, X$_{16}$ or X$_{20}$ may be D or X$_{16}$ is A. Where the agent is a competitive inhibitor, some of the above mutations would enhance the inhibitory activity of the peptide, others would completely or partially abolish the inhibitory activity of the peptide. Mutations may be observed alone or in combination, for example, any one substitution, X$_{1-20}$, occurs within the context of the wild type sequence at any one time, a combination of two mutations such as: X$_5$ and X$_9$, X$_5$ and X$_{16}$, or X$_9$ and X$_{16}$ or three mutations are found in the same peptide, X$_5$, with X$_9$, and X$_{16}$. Additional mutations of the above inhibitor may include the sequence:

X$_1$X$_2$DVWDWICTX$_3$X$_4$X$_5$X$_6$X$_7$X$_8$X$_9$ (SEQ ID NO:468) wherein when X$_1$ and X$_2$ are present, X$_1$ is L and X$_2$ is R; wherein X$_1$ and X$_2$ are present, X$_3$X$_4$X$_5$X$_6$X$_7$X$_8$ and X$_9$ are optionally present, and when X$_3$, X$_4$, X$_5$, X$_6$, X$_7$, X$_8$ and X$_9$ are present, X$_3$ is V, X$_4$ is L, X$_5$ is T, X$_6$ is D, X$_7$ is F, X$_8$ is K and X$_9$ is T; and wherein X$_6$ is present, X$_3$, X$_4$ and X$_5$ are all present, wherein X$_6$ is D, X$_3$ is V, X$_4$ is L, and X$_5$ is T. In particular where the sequence is LRDVWDWICTVLT-DFKT (SEQ ID NO: 463, LRDVWDWICT (SEQ ID NO:464) or DVWDWICTVLTD (SEQ ID NO: 465). In another embodiment, the competitive inhibitor may be SWLRDVWDWIC (SEQ ID NO:466).

A mutant and competitive inhibitor, of NS4B may include the sequence:

X$_1$X$_2$X$_3$X$_4$X$_5$X$_6$X$_7$X$_8$X$_9$X$_{10}$X$_{11}$X$_{12}$X$_{13}$X$_{14}$X$_{15}$X$_{16}$X$_{17}$X$_{18}$X$_{19}$

X$_{20}$X$_{21}$X$_{22}$X$_{23}$X$_{24}$X$_{25}$X$_{26}$X$_{27}$X$_{28}$X$_{29}$ where X$_1$ is Y, A or H; X$_2$ is I, E or L; X$_3$ is E, A or Q; X$_4$ is Q, V or R; X$_5$ is G, A or D; X$_6$ is M, E or C; X$_7$ is M, E or C; X$_8$ is L, E or Q; X$_9$ -continued is A, D or S; X₁₀ is E, A or Q; X₁₁ is Q, V, or R; X₁₂ is F, D or L; X₁₃ is K, I or Q; X₁₄ is Q, V, or R; X₁₅ is K, I or Q; X₁₆ is A, D or G; X₁₇ is L, A or K; X₁₈ is G, E or S; X₁₉ is L, A or K; X₂₀ is L, A or K; X₂₁ is Q, V or R; X₂₂ is T, A or W; X₂₃ is A, D or G; X₂₄ is S, D or A; X₂₅ is R, L or W; X₂₆ is Q, V or R; X₂₇ is A, D or G; and X₂₈ is E, A or Q.

While the majority of the above mutations and substitutions are conservative (i.e. wild type hydrophobic residues are substituted with additional hydrophobic residues (for example, A to F), charged residues are substituted with similarly charged residues, etc.), it is noted that nonconservative substitutions may also be performed. For example, where a wild type hydrophobic residue is substituted with a hydrophilic residue, or a negatively charged residue (for example, D) is substituted with a positively charged residue (for example, K).

Where the agent is a competitive inhibitor, some of the above mutations would enhance the inhibitory activity of the peptide, others would completely or partially abolish the inhibitory activity of the peptide. Mutations may be observed alone or in combination, for example, any one substitution, $X_{1-28}$, occurs within the context of the wild type sequence at any one time, a combination of two mutations such as: $X_2$ and $X_5$, $X_2$ and $X_{19}$, or $X_5$ and $X_{19}$ or three mutations are found in the same peptide, $X_2$, with $X_5$, and $X_{19}$.

In another embodiment, the agent may be a complementary peptide to the helix. Complementary peptides may interrupt the binding between the helix and the membrane, achieving the desired effect. Such complementary peptides may also inhibit the formation of the amphipathic helix, may interact or bind to the helix to inhibit binding of the helix to cellular membranes, or may otherwise inhibit the amphipathic helices.

For example, the HCV genomic RNA sequence that codes for the NS4B amphipathic helix in the HCV genotype 1A sequence is:

UACAUCGAGCAAGGGAUGAUGCUCGCUGAGCAGU (SEQ ID NO: 17)
UCAAGCAGAAGGCCCUCGGCCUCCUGCAGACCGC
GUCCCGCCAAGCAGAG.

(Kolykhalov, A. A. and Rice, C. M., *Science* 277 (5325), 570-574 (1997); GenBank Accession No.: AF009606.) The protein translation of the above sequence is: YIEQGMMLAEQFKQKALGLLQTASRQAE (SEQ ID NO: 18). The reverse complement cDNA sequence corresponding to the HCV genomic RNA sequence that codes for the NS4B amphipathic helix (GenBank Accession No.: AF009606) is: CTCTGCTTGGCGGGACGCGGTCTGCAGGAGGCCGAGGGCCTTCTGCTTGA ACTGCTCAGCGAGCATCATCCCTTGCTCGATGTA (SEQ ID NO: 19). The complementary peptide translated from the reverse complement sequence is: LCLAGRGLQEAEGLLLELLSEHHPLLDV (SEQ ID NO: 20). This complementary peptide, as a whole, or in part, may be active as an HCV antiviral or may be useful in the prediction of small molecules that are HCV antivirals. In one embodiment a fragment of this complementary peptide comprising 6-27 amino acids may be used in the discovery of HCV antivirals. Table 1 sets forth exemplary peptides (SEQ ID NOS: 21-295) of this embodiment.

TABLE 1

All smaller NS4B complementary peptides with 6 or more amino acids:

| Sequence | Sequence Identification Number |
|---|---|
| LQEAEG | SEQ ID NO: 21 |
| CLAGRG | SEQ ID NO: 22 |
| LELLSE | SEQ ID NO: 23 |
| GLQEAE | SEQ ID NO: 24 |
| LLELLS | SEQ ID NO: 25 |
| QEAEGL | SEQ ID NO: 26 |
| RGLQEA | SEQ ID NO: 27 |
| LAGRGL | SEQ ID NO: 28 |
| GRGLQE | SEQ ID NO: 29 |
| ELLSEH | SEQ ID NO: 30 |
| LLLELL | SEQ ID NO: 31 |
| LCLAGR | SEQ ID NO: 32 |
| HPLLDV | SEQ ID NO: 33 |
| AEGLLL | SEQ ID NO: 34 |
| AGRGLQ | SEQ ID NO: 35 |
| EAEGLL | SEQ ID NO: 36 |
| LSEHHP | SEQ ID NO: 37 |
| HHPLLD | SEQ ID NO: 38 |
| EGLLLE | SEQ ID NO: 39 |
| SEHHPL | SEQ ID NO: 40 |
| LLSEHH | SEQ ID NO: 41 |
| EHHPLL | SEQ ID NO: 42 |
| GLLLEL | SEQ ID NO: 43 |
| LELLSEH | SEQ ID NO: 44 |
| ELLSEHH | SEQ ID NO: 45 |
| LLELLSE | SEQ ID NO: 46 |
| LLSEHHP | SEQ ID NO: 47 |
| HHPLLDV | SEQ ID NO: 48 |
| GLLLELL | SEQ ID NO: 49 |
| LAGRGLQ | SEQ ID NO: 50 |
| LSEHHPL | SEQ ID NO: 51 |
| LCLAGRG | SEQ ID NO: 52 |

TABLE 1-continued

All smaller NS4B complementary peptides with 6 or more amino acids:

| Sequence | Sequence Identification Number |
|---|---|
| LQEAEGL | SEQ ID NO: 53 |
| AGRGLQE | SEQ ID NO: 54 |
| AEGLLLE | SEQ ID NO: 55 |
| GRGLQEA | SEQ ID NO: 56 |
| RGLQEAE | SEQ ID NO: 57 |
| QEAEGLL | SEQ ID NO: 58 |
| SEHHPLL | SEQ ID NO: 59 |
| EHHPLLD | SEQ ID NO: 60 |
| GLQEAEG | SEQ ID NO: 61 |
| EGLLLEL | SEQ ID NO: 62 |
| LLLELLS | SEQ ID NO: 63 |
| EAEGLLL | SEQ ID NO: 64 |
| CLAGRGL | SEQ ID NO: 65 |
| CLAGRGLQ | SEQ ID NO: 66 |
| QEAEGLLL | SEQ ID NO: 67 |
| LAGRGLQE | SEQ ID NO: 68 |
| LCLAGRGL | SEQ ID NO: 69 |
| AGRGLQEA | SEQ ID NO: 70 |
| LLLELLSE | SEQ ID NO: 71 |
| LELLSEHH | SEQ ID NO: 72 |
| AEGLLLEL | SEQ ID NO: 73 |
| EGLLLELL | SEQ ID NO: 74 |
| LLSEHHPL | SEQ ID NO: 75 |
| GRGLQEAE | SEQ ID NO: 76 |
| EAEGLLLE | SEQ ID NO: 77 |
| RGLQEAEG | SEQ ID NO: 78 |
| LLELLSEH | SEQ ID NO: 79 |
| SEHHPLLD | SEQ ID NO: 80 |
| LSEHHPLL | SEQ ID NO: 81 |
| LQEAEGLL | SEQ ID NO: 82 |
| ELLSEHHP | SEQ ID NO: 83 |
| GLLLELLS | SEQ ID NO: 84 |
| EHHPLLDV | SEQ ID NO: 85 |
| GLQEAEGL | SEQ ID NO: 86 |
| LLSEHHPLL | SEQ ID NO: 87 |
| LELLSEHHP | SEQ ID NO: 88 |
| RGLQEAEGL | SEQ ID NO: 89 |
| ELLSEHHPL | SEQ ID NO: 90 |
| LCLAGRGLQ | SEQ ID NO: 91 |
| AGRGLQEAE | SEQ ID NO: 92 |
| GLLLELLSE | SEQ ID NO: 93 |
| LSEHHPLLD | SEQ ID NO: 94 |
| EGLLLELLS | SEQ ID NO: 95 |
| GLQEAEGLL | SEQ ID NO: 96 |
| AEGLLLELL | SEQ ID NO: 97 |
| QEAEGLLLE | SEQ ID NO: 98 |
| SEHHPLLDV | SEQ ID NO: 99 |
| LLLELLSEH | SEQ ID NO: 100 |
| GRGLQEAEG | SEQ ID NO: 101 |
| CLAGRGLQE | SEQ ID NO: 102 |
| EAEGLLLEL | SEQ ID NO: 103 |
| LAGRGLQEA | SEQ ID NO: 104 |
| LLELLSEHH | SEQ ID NO: 105 |
| LQEAEGLLL | SEQ ID NO: 106 |
| LSEHHPLLDV | SEQ ID NO: 107 |
| LELLSEHHPL | SEQ ID NO: 108 |
| RGLQEAEGLL | SEQ ID NO: 109 |
| LLSEHHPLLD | SEQ ID NO: 110 |
| AEGLLLELLS | SEQ ID NO: 111 |
| GLQEAEGLLL | SEQ ID NO: 112 |
| EGLLLELLSE | SEQ ID NO: 113 |
| LCLAGRGLQE | SEQ ID NO: 114 |
| LLLELLSEHH | SEQ ID NO: 115 |
| EAEGLLLELL | SEQ ID NO: 116 |
| GLLLELLSEH | SEQ ID NO: 117 |
| ELLSEHHPLL | SEQ ID NO: 118 |
| GRGLQEAEGL | SEQ ID NO: 119 |
| LQEAEGLLLE | SEQ ID NO: 120 |
| LLELLSEHHP | SEQ ID NO: 121 |
| CLAGRGLQEA | SEQ ID NO: 122 |
| QEAEGLLLEL | SEQ ID NO: 123 |
| AGRGLQEAEG | SEQ ID NO: 124 |

TABLE 1-continued

All smaller NS4B complementary peptides with 6 or more amino acids:

| Sequence | Sequence Identification Number |
|---|---|
| LAGRGLQEAE | SEQ ID NO: 125 |
| LLELLSEHHPL | SEQ ID NO: 126 |
| CLAGRGLQEAE | SEQ ID NO: 127 |
| RGLQEAEGLLL | SEQ ID NO: 128 |
| LAGRGLQEAEG | SEQ ID NO: 129 |
| LQEAEGLLLEL | SEQ ID NO: 130 |
| LLLELLSEHHP | SEQ ID NO: 131 |
| ELLSEHHPLLD | SEQ ID NO: 132 |
| AGRGLQEAEGL | SEQ ID NO: 133 |
| LLSEHHPLLDV | SEQ ID NO: 134 |
| LCLAGRGLQEA | SEQ ID NO: 135 |
| GLLLELLSEHH | SEQ ID NO: 136 |
| LELLSEHHPLL | SEQ ID NO: 137 |
| QEAEGLLLELL | SEQ ID NO: 138 |
| EGLLLELLSEH | SEQ ID NO: 139 |
| GRGLQEAEGLL | SEQ ID NO: 140 |
| AEGLLLELLSE | SEQ ID NO: 141 |
| GLQEAEGLLLE | SEQ ID NO: 142 |
| EAEGLLLELLS | SEQ ID NO: 143 |
| EGLLLELLSEHH | SEQ ID NO: 144 |
| RGLQEAEGLLLE | SEQ ID NO: 145 |
| GLLLELLSEHHP | SEQ ID NO: 146 |
| LQEAEGLLLELL | SEQ ID NO: 147 |
| GLQEAEGLLLEL | SEQ ID NO: 148 |
| LAGRGLQEAEGL | SEQ ID NO: 149 |
| GRGLQEAEGLLL | SEQ ID NO: 150 |
| QEAEGLLLELLS | SEQ ID NO: 151 |
| AEGLLLELLSEH | SEQ ID NO: 152 |
| AGRGLQEAEGLL | SEQ ID NO: 153 |
| LELLSEHHPLLD | SEQ ID NO: 154 |
| LCLAGRGLQEAE | SEQ ID NO: 155 |
| LLLELLSEHHPL | SEQ ID NO: 156 |
| LLELLSEHHPLL | SEQ ID NO: 157 |
| ELLSEHHPLLDV | SEQ ID NO: 158 |
| EAEGLLLELLSE | SEQ ID NO: 159 |
| CLAGRGLQEAEG | SEQ ID NO: 160 |
| CLAGRGLQEAEGL | SEQ ID NO: 161 |
| RGLQEAEGLLLEL | SEQ ID NO: 162 |
| LLELLSEHHPLLD | SEQ ID NO: 163 |
| GRGLQEAEGLLLE | SEQ ID NO: 164 |
| LCLAGRGLQEAEG | SEQ ID NO: 165 |
| LELLSEHHPLLDV | SEQ ID NO: 166 |
| EGLLLELLSEHHP | SEQ ID NO: 167 |
| EAEGLLLELLSEH | SEQ ID NO: 168 |
| GLQEAEGLLLELL | SEQ ID NO: 169 |
| AGRGLQEAEGLLL | SEQ ID NO: 170 |
| AEGLLLELLSEHH | SEQ ID NO: 171 |
| LAGRGLQEAEGLL | SEQ ID NO: 172 |
| QEAEGLLLELLSE | SEQ ID NO: 173 |
| LLLELLSEHHPLL | SEQ ID NO: 174 |
| LQEAEGLLLELLS | SEQ ID NO: 175 |
| GLLLELLSEHHPL | SEQ ID NO: 176 |
| EAEGLLLELLSEHH | SEQ ID NO: 177 |
| EGLLLELLSEHHPL | SEQ ID NO: 178 |
| AGRGLQEAEGLLLE | SEQ ID NO: 179 |
| LCLAGRGLQEAEGL | SEQ ID NO: 180 |
| GLLLELLSEHHPLL | SEQ ID NO: 181 |
| QEAEGLLLELLSEH | SEQ ID NO: 182 |
| RGLQEAEGLLLELL | SEQ ID NO: 183 |
| LLLELLSEHHPLLD | SEQ ID NO: 184 |
| LQEAEGLLLELLSE | SEQ ID NO: 185 |
| LLELLSEHHPLLDV | SEQ ID NO: 186 |
| GLQEAEGLLLELLS | SEQ ID NO: 187 |
| GRGLQEAEGLLLEL | SEQ ID NO: 188 |
| AEGLLLELLSEHHP | SEQ ID NO: 189 |
| CLAGRGLQEAEGLL | SEQ ID NO: 190 |
| LAGRGLQEAEGLLL | SEQ ID NO: 191 |
| LLLELLSEHHPLLDV | SEQ ID NO: 192 |
| AGRGLQEAEGLLLEL | SEQ ID NO: 193 |
| AEGLLLELLSEHHPL | SEQ ID NO: 194 |
| GLLLELLSEHHPLLD | SEQ ID NO: 195 |
| LQEAEGLLLELLSEH | SEQ ID NO: 196 |
| GLQEAEGLLLELLSE | SEQ ID NO: 197 |

TABLE 1-continued

All smaller NS4B complementary peptides with 6 or more amino acids:

| Sequence | Sequence Identification Number |
|---|---|
| LCLAGRGLQEAEGLL | SEQ ID NO: 198 |
| EAEGLLLELLSEHHP | SEQ ID NO: 199 |
| GRGLQEAEGLLLELL | SEQ ID NO: 200 |
| QEAEGLLLELLSEHH | SEQ ID NO: 201 |
| LAGRGLQEAEGLLLE | SEQ ID NO: 202 |
| CLAGRGLQEAEGLLL | SEQ ID NO: 203 |
| EGLLLELLSEHHPLL | SEQ ID NO: 204 |
| RGLQEAEGLLLELLS | SEQ ID NO: 205 |
| LAGRGLQEAEGLLLEL | SEQ ID NO: 206 |
| GLLLELLSEHHLPLLDV | SEQ ID NO: 207 |
| GRGLQEAEGLLLELLS | SEQ ID NO: 208 |
| AGRGLQEAEGLLLELL | SEQ ID NO: 209 |
| GLQEAEGLLLELLSEH | SEQ ID NO: 210 |
| RGLQEAEGLLLELLSE | SEQ ID NO: 211 |
| LQEAEGLLLELLSEHH | SEQ ID NO: 212 |
| CLAGRGLQEAEGLLLE | SEQ ID NO: 213 |
| QEAEGLLLELLSEHHP | SEQ ID NO: 214 |
| AEGLLLELLSEHHPLL | SEQ ID NO: 215 |
| EAEGLLLELLSEHHPL | SEQ ID NO: 216 |
| LCLAGRGLQEAEGLLL | SEQ ID NO: 217 |
| EGLLLELLSEHHPLLD | SEQ ID NO: 218 |
| LCLAGRGLQEAEGLLLE | SEQ ID NO: 219 |
| QEAEGLLLELLSEHHPL | SEQ ID NO: 220 |
| EAEGLLLELLSEHHPLL | SEQ ID NO: 221 |
| RGLQEAEGLLLELLSEH | SEQ ID NO: 222 |
| CLAGRGLQEAEGLLLEL | SEQ ID NO: 223 |
| GRGLQEAEGLLLELLSE | SEQ ID NO: 224 |
| LAGRGLQEAEGLLLELL | SEQ ID NO: 225 |
| AGRGLQEAEGLLLELLS | SEQ ID NO: 226 |
| GLQEAEGLLLELLSEHH | SEQ ID NO: 227 |
| EGLLLELLSEHHPLLDV | SEQ ID NO: 228 |
| AEGLLLELLSEHHPLLD | SEQ ID NO: 229 |
| LQEAEGLLLELLSEHHP | SEQ ID NO: 230 |
| CLAGRGLQEAEGLLLELL | SEQ ID NO: 231 |
| LQEAEGLLLELLSEHHPL | SEQ ID NO: 232 |
| GRGLQEAEGLLLELLSEH | SEQ ID NO: 233 |
| EAEGLLLELLSEHHPLLD | SEQ ID NO: 234 |
| AEGLLLELLSEHHPLLDV | SEQ ID NO: 235 |
| GLQEAEGLLLELLSEHHP | SEQ ID NO: 236 |
| RGLQEAEGLLLELLSEHH | SEQ ID NO: 237 |
| QEAEGLLLELLSEHHPLL | SEQ ID NO: 238 |
| LAGRGLQEAEGLLLELLS | SEQ ID NO: 239 |
| LCLAGRGLQEAEGLLLEL | SEQ ID NO: 240 |
| AGRGLQEAEGLLLELLSE | SEQ ID NO: 241 |
| AGRGLQEAEGLLLELLSEH | SEQ ID NO: 242 |
| GLQEAEGLLLELLSEHHPL | SEQ ID NO: 243 |
| GRGLQEAEGLLLELLSEHH | SEQ ID NO: 244 |
| LCLAGRGLQEAEGLLLELL | SEQ ID NO: 245 |
| CLAGRGLQEAEGLLLELLS | SEQ ID NO: 246 |
| RGLQEAEGLLLELLSEHHP | SEQ ID NO: 247 |
| LAGRGLQEAEGLLLELLSE | SEQ ID NO: 248 |
| QEAEGLLLELLSEHHPLLD | SEQ ID NO: 249 |
| LQEAEGLLLELLSEHHPLL | SEQ ID NO: 250 |
| EAEGLLLELLSEHHPLLDV | SEQ ID NO: 251 |
| RGLQEAEGLLLELLSEHHPL | SEQ ID NO: 252 |
| GLQEAEGLLLELLSEHHPLL | SEQ ID NO: 253 |
| AGRGLQEAEGLLLELLSEHH | SEQ ID NO: 254 |
| LAGRGLQEAEGLLLELLSEH | SEQ ID NO: 255 |
| GRGLQEAEGLLLELLSEHHP | SEQ ID NO: 256 |
| LCLAGRGLQEAEGLLLELLS | SEQ ID NO: 257 |
| LQEAEGLLLELLSEHHPLLD | SEQ ID NO: 258 |
| QEAEGLLLELLSEHHPLLDV | SEQ ID NO: 259 |
| CLAGRGLQEAEGLLLELLSE | SEQ ID NO: 260 |
| LCLAGRGLQEAEGLLLELLSE | SEQ ID NO: 261 |
| RGLQEAEGLLLELLSEHHPLL | SEQ ID NO: 262 |
| LQEAEGLLLELLSEHHPLLDV | SEQ ID NO: 263 |
| GRGLQEAEGLLLELLSEHHPL | SEQ ID NO: 264 |
| AGRGLQEAEGLLLELLSEHHP | SEQ ID NO: 265 |
| LAGRGLQEAEGLLLELLSEHH | SEQ ID NO: 266 |
| CLAGRGLQEAEGLLLELLSEH | SEQ ID NO: 267 |
| GLQEAEGLLLELLSEHHPLLD | SEQ ID NO: 268 |
| GLQEAEGLLLELLSEHHPLLDV | SEQ ID NO: 269 |
| AGRGLQEAEGLLLELLSEHHPL | SEQ ID NO: 270 |

TABLE 1-continued

All smaller NS4B complementary peptides with 6 or more amino acids:

| Sequence | Sequence Identification Number |
|---|---|
| CLAGRGLQEAEGLLLELLSEHH | SEQ ID NO: 271 |
| GRGLQEAEGLLLELLSEHHPLL | SEQ ID NO: 272 |
| RGLQEAEGLLLELLSEHHPLLD | SEQ ID NO: 273 |
| LAGRGLQEAEGLLLELLSEHHP | SEQ ID NO: 274 |
| LCLAGRGLQEAEGLLLELLSEH | SEQ ID NO: 275 |
| CLAGRGLQEAEGLLLELLSEHHP | SEQ ID NO: 276 |
| GRGLQEAEGLLLELLSEHHPLLD | SEQ ID NO: 277 |
| LCLAGRGLQEAEGLLLELLSEHH | SEQ ID NO: 278 |
| LAGRGLQEAEGLLLELLSEHHPL | SEQ ID NO: 279 |
| RGLQEAEGLLLELLSEHHPLLDV | SEQ ID NO: 280 |
| AGRGLQEAEGLLLELLSEHHPLL | SEQ ID NO: 281 |
| AGRGLQEAEGLLLELLSEHHPLLD | SEQ ID NO: 282 |
| CLAGRGLQEAEGLLLELLSEHHPL | SEQ ID NO: 283 |
| LCLAGRGLQEAEGLLLELLSEHHP | SEQ ID NO: 284 |
| GRGLQEAEGLLLELLSEHHPLLDV | SEQ ID NO: 285 |
| LAGRGLQEAEGLLLELLSEHHPLL | SEQ ID NO: 286 |
| AGRGLQEAEGLLLELLSEHHPLLDV | SEQ ID NO: 287 |
| LCLAGRGLQEAEGLLLELLSEHHPL | SEQ ID NO: 288 |
| LAGRGLQEAEGLLLELLSEHHPLLD | SEQ ID NO: 289 |
| CLAGRGLQEAEGLLLELLSEHHPLL | SEQ ID NO: 290 |
| LCLAGRGLQEAEGLLLELLSEHHPLL | SEQ ID NO: 291 |
| LAGRGLQEAEGLLLELLSEHHPLLDV | SEQ ID NO: 292 |
| CLAGRGLQEAEGLLLELLSEHHPLLD | SEQ ID NO: 293 |
| LCLAGRGLQEAEGLLLELLSEHHPLLD | SEQ ID NO: 294 |
| CLAGRGLQEAEGLLLELLSEHHPLLDV | SEQ ID NO: 295 |

In a particular embodiment, the complementary peptides of the invention are used, in whole or in part, in the prediction of small molecules that are HCV antivirals. "Small molecule" as defined above, may include synthetic organic structures typical of pharmaceuticals, and may also include peptides, nucleic acids, peptide nucleic acids, carbohydrates, lipids, and the like. Additionally, small molecules, as used herein, may include chemically synthesized peptidomimetics of the 6-mer to 9-mer peptides of the invention.

Additionally, the HCV genomic RNA sequence that codes for the NS5A amphipathic helix in the HCV genotype 1A sequence is: UGGCUAAGGGACAUCUGGGACUGGAUAUGCGAGGUGCUGAGCGACUUU AAGACCUGGCUGAAAGCCAAGCUC (SEQ ID NO: 296). (Kolykhalov, A. A. and Rice, C. M., *Science* 277 (5325), 570-574 (1997); GenBank Accession No.: AF009606.) The protein translation of the above sequence is: WLRDIWDWICEVLSDFKTWLKAKL (SEQ ID NO: 297). The reverse complement cDNA sequence corresponding to the HCV genomic RNA sequence that codes for the NS5A amphipathic helix (GenBank Accession No.: AF009606) is: GAGCTTGGCTTTCAGCCAGGTCTTAAAGTCGCTCAGCACCTCGCATATCCA GTCCCAGATGTCCCTTAGCCA (SEQ ID NO: 298). This reverse complement sequence contains a stop codon at codon 23. The complementary peptide translated from the reverse complement sequence is: ELGFQPGLKVAQHLAYPVPDVP (SEQ ID NO: 299). This complementary peptide, as a whole, or in part, may be active as an HCV antiviral or may be useful in the prediction of small molecules that are HCV antivirals. In one embodiment a fragment of this complementary peptide comprising 6-21 amino acids may is used in the discovery of HCV antivirals. Table 2 sets forth exemplary peptides (SEQ ID NOS: 300-451) of this embodiment.

TABLE 2

NS5A complementary peptides with 6 or more amino acids:

| Sequence | Sequence Identification Number |
|---|---|
| AQHLAY | SEQ ID NO: 300 |
| LGFQPG | SEQ ID NO: 301 |
| GLKVAQ | SEQ ID NO: 302 |
| ELGFQP | SEQ ID NO: 303 |
| PVPDVP | SEQ ID NO: 304 |
| FQPGLK | SEQ ID NO: 305 |
| GFQPGL | SEQ ID NO: 306 |
| VAQHLA | SEQ ID NO: 307 |
| LKVAQH | SEQ ID NO: 308 |
| HLAYPV | SEQ ID NO: 309 |
| KVAQHL | SEQ ID NO: 310 |
| QPGLKV | SEQ ID NO: 311 |
| LAYPVP | SEQ ID NO: 312 |
| YPVPDV | SEQ ID NO: 313 |
| QHLAYP | SEQ ID NO: 314 |
| PGLKVA | SEQ ID NO: 315 |
| AYPVPD | SEQ ID NO: 316 |
| QPGLKVA | SEQ ID NO: 317 |
| ELGFQPG | SEQ ID NO: 318 |
| HLAYPVP | SEQ ID NO: 319 |
| LAYPVPD | SEQ ID NO: 320 |
| AQHLAYP | SEQ ID NO: 321 |
| FQPGLKV | SEQ ID NO: 322 |
| KVAQHLA | SEQ ID NO: 323 |
| LGFQPGL | SEQ ID NO: 324 |
| AYPVPDV | SEQ ID NO: 325 |

TABLE 2-continued

NS5A complementary peptides with 6 or more amino acids:

| Sequence | Sequence Identification Number |
|---|---|
| PGLKVAQ | SEQ ID NO: 326 |
| LKVAQHL | SEQ ID NO: 327 |
| GLKVAQH | SEQ ID NO: 328 |
| VAQHLAY | SEQ ID NO: 329 |
| GFQPGLK | SEQ ID NO: 330 |
| QHLAYPV | SEQ ID NO: 331 |
| YPVPDVP | SEQ ID NO: 332 |
| AYPVPDVP | SEQ ID NO: 333 |
| PGLKVAQH | SEQ ID NO: 334 |
| QHLAYPVP | SEQ ID NO: 335 |
| LAYPVPDV | SEQ ID NO: 336 |
| LKVAQHLA | SEQ ID NO: 337 |
| GLKVAQHL | SEQ ID NO: 338 |
| GFQPGLKV | SEQ ID NO: 339 |
| AQHLAYPV | SEQ ID NO: 340 |
| VAQHLAYP | SEQ ID NO: 341 |
| KVAQHLAY | SEQ ID NO: 342 |
| ELGFQPGL | SEQ ID NO: 343 |
| LGFQPGLK | SEQ ID NO: 344 |
| FQPGLKVA | SEQ ID NO: 345 |
| HLAYPVPD | SEQ ID NO: 346 |
| QPGLKVAK | SEQ ID NO: 347 |
| ELGFQPGLK | SEQ ID NO: 348 |
| VAQHLAYPV | SEQ ID NO: 349 |
| LGFQPGLKV | SEQ ID NO: 350 |
| QPGLKVAQH | SEQ ID NO: 351 |
| KVAQHLAYP | SEQ ID NO: 352 |
| PGLKVAQHL | SEQ ID NO: 353 |
| FQPGLKVAQ | SEQ ID NO: 354 |
| GLKVAQHLA | SEQ ID NO: 355 |
| LAYPVPDVP | SEQ ID NO: 356 |
| HLAYPVPDV | SEQ ID NO: 357 |
| GFQPGLKVA | SEQ ID NO: 358 |
| AQHLAYPVP | SEQ ID NO: 359 |
| QHLAYPVPD | SEQ ID NO: 360 |
| LKVAQHLAY | SEQ ID NO: 361 |
| QPGLKVAQHL | SEQ ID NO: 362 |
| PGLKVAQHLA | SEQ ID NO: 363 |
| HLAYPVPDVP | SEQ ID NO: 364 |
| GLKVAQHLAY | SEQ ID NO: 365 |
| VAQHLAYPVP | SEQ ID NO: 366 |
| KVAQHLAYPV | SEQ ID NO: 367 |
| GFQPGLKVAQ | SEQ ID NO: 368 |
| QHLAYPVPDV | SEQ ID NO: 369 |
| AQHLAYPVPD | SEQ ID NO: 370 |
| FQPGLKVAQH | SEQ ID NO: 371 |
| ELGFQPGLKV | SEQ ID NO: 372 |
| LKVAQHLAYP | SEQ ID NO: 373 |
| LGFQPGLKVA | SEQ ID NO: 374 |
| QHLAYPVPDVP | SEQ ID NO: 375 |
| LKVAQHLAYPV | SEQ ID NO: 376 |
| VAQHLAYPVPD | SEQ ID NO: 377 |
| PGLKVAQHLAY | SEQ ID NO: 378 |
| LGFQPGLKVAQ | SEQ ID NO: 379 |
| KVAQHLAYPVP | SEQ ID NO: 380 |
| ELGFQPGLKVA | SEQ ID NO: 381 |
| GLKVAQHLAYP | SEQ ID NO: 382 |
| AQHLAYPVPDV | SEQ ID NO: 383 |
| FQPGLKVAQHL | SEQ ID NO: 384 |
| QPGLKVAQHLA | SEQ ID NO: 385 |
| GFQPGLKVAQH | SEQ ID NO: 386 |
| LGFQPGLKVAQH | SEQ ID NO: 387 |
| PGLKVAQHLAYP | SEQ ID NO: 388 |
| LKVAQHLAYPVP | SEQ ID NO: 389 |
| GFQPGLKVAQHL | SEQ ID NO: 390 |
| VAQHLAYPVPDV | SEQ ID NO: 391 |
| QPGLKVAQHLAY | SEQ ID NO: 392 |
| ELGFQPGLKVAQ | SEQ ID NO: 393 |
| AQHLAYPVPDVP | SEQ ID NO: 394 |
| KVAQHLAYPVPD | SEQ ID NO: 395 |
| FQPGLKVAQHLA | SEQ ID NO: 396 |
| GLKVAQHLAYPV | SEQ ID NO: 397 |
| LGFQPGLKVAQHL | SEQ ID NO: 398 |

TABLE 2-continued

NS5A complementary peptides with 6 or more amino acids:

| Sequence | Sequence Identification Number |
|---|---|
| VAQHLAYPVPDVP | SEQ ID NO: 399 |
| PGLKVAQHLAYPV | SEQ ID NO: 400 |
| GFQPGLKVAQHLA | SEQ ID NO: 401 |
| LKVAQHLAYPVPD | SEQ ID NO: 402 |
| QPGLKVAQHLAYP | SEQ ID NO: 403 |
| ELGFQPGLKVAQH | SEQ ID NO: 404 |
| GLKVAQHLAYPVP | SEQ ID NO: 405 |
| FQPGLKVAQHLAY | SEQ ID NO: 406 |
| KVAQHLAYPVPDV | SEQ ID NO: 407 |
| ELGFQPGLKVAQHL | SEQ ID NO: 408 |
| QPGLKVAQHLAYPV | SEQ ID NO: 409 |
| GFQPGLKVAQHLAY | SEQ ID NO: 410 |
| LGFQPGLKVAQHLA | SEQ ID NO: 411 |
| FQPGLKVAQHLAYP | SEQ ID NO: 412 |
| KVAQHLAYPVPDVP | SEQ ID NO: 413 |
| PGLKVAQHLAYPVP | SEQ ID NO: 414 |
| LKVAQHLAYPVPDV | SEQ ID NO: 415 |
| GLKVAQHLAYPVPD | SEQ ID NO: 416 |
| GLKVAQHLAYPVPDV | SEQ ID NO: 417 |
| PGLKVAQHLAYPVPD | SEQ ID NO: 418 |
| ELGFQPGLKVAQHLA | SEQ ID NO: 419 |
| LGFQPGLKVAQHLAY | SEQ ID NO: 420 |
| GFQPGLKVAQHLAYP | SEQ ID NO: 421 |
| QPGLKVAQHLAYPVP | SEQ ID NO: 422 |
| FQPGLKVAQHLAYPV | SEQ ID NO: 423 |
| LKVAQHLAYPVPDVP | SEQ ID NO: 424 |
| FQPGLKVAQHLAYPVP | SEQ ID NO: 425 |
| GFQPGLKVAQHLAYPV | SEQ ID NO: 426 |
| GLKVAQHLAYPVPDVP | SEQ ID NO: 427 |
| PGLKVAQHLAYPVPDV | SEQ ID NO: 428 |
| QPGLKVAQHLAYPVPD | SEQ ID NO: 429 |
| ELGFQPGLKVAQHLAY | SEQ ID NO: 430 |
| LGFQPGLKVAQHLAYP | SEQ ID NO: 431 |
| GFQPGLKVAQHLAYPVP | SEQ ID NO: 432 |
| FQPGLKVAQHLAYPVPD | SEQ ID NO: 433 |
| QPGLKVAQHLAYPVPDV | SEQ ID NO: 434 |
| PGLKVAQHLAYPVPDVP | SEQ ID NO: 435 |
| LGFQPGLKVAQHLAYPV | SEQ ID NO: 436 |
| ELGFQPGLKVAQHLAYP | SEQ ID NO: 437 |
| ELGFQPGLKVAQHLAYPV | SEQ ID NO: 438 |
| QPGLKVAQHLAYPVPDVP | SEQ ID NO: 439 |
| LGFQPGLKVAQHLAYPVP | SEQ ID NO: 440 |
| FQPGLKVAQHLAYPVPDV | SEQ ID NO: 441 |
| GFQPGLKVAQHLAYPVPD | SEQ ID NO: 442 |
| FQPGLKVAQHLAYPVPDVP | SEQ ID NO: 443 |
| LGFQPGLKVAQHLAYPVPD | SEQ ID NO: 444 |
| GFQPGLKVAQHLAYPVPDV | SEQ ID NO: 445 |
| ELGFQPGLKVAQHLAYPVP | SEQ ID NO: 446 |
| LGFQPGLKVAQHLAYPVPDV | SEQ ID NO: 447 |
| ELGFQPGLKVAQHLAYPVPD | SEQ ID NO: 448 |
| GFQPGLKVAQHLAYPVPDVP | SEQ ID NO: 449 |
| ELGFQPGLKVAQHLAYPVPDV | SEQ ID NO: 450 |
| LGFQPGLKVAQHLAYPVPDVP | SEQ ID NO: 451 |

The peptides that mimic the helices and functional fragments thereof are administered in formulations and by routes well understood. A variety of methods for introducing such substances are known, typically, by injection, aerosol administration, suppository, and, with proper design, oral administration. This general statement is true as well with respect to providing expression systems for peptides represented by the helix mimics.

In addition to the peptides or other compounds of the invention, combination therapies including known HCV inhibitors can be utilized in the present invention. For example, it may be desirable to administer both a peptide or peptides of the invention in combination with interferon to a subject infected with HCV. Other drugs or compounds known in the art to be effective against HCV, can also be used.

In one embodiment, the invention provides a method of screening compounds, to identify those that selectively inhibit the binding of HCV nonstructural proteins (for example, NS4B or NS5A) and cellular membranes. Methods known to those of skill in the art, can be readily adapted to detect interference with the binding of these components. The method of screening may involve high-throughput techniques. For example, to screen for compounds that selectively inhibit the binding of HCV nonstructural proteins and cellular membranes, a synthetic reaction mix, a viral fragment or component, or a preparation of any thereof, comprising an HCV nonstructural protein and a labeled substrate or ligand of such polypeptide is incubated in the absence or the presence of a candidate molecule that may inhibit the binding of the HCV nonstructural proteins and the cellular membrane. The ability of the candidate molecule to inhibit the binding of the HCV nonstructural protein and the cellular membrane is reflected in decreased binding of the labeled ligand or decreased production of product from such substrate.

In another aspect, the screening can be performed by adding the candidate compound to intact cells that have been infected by HCV, or that contain an HCV replicon, and then examining the component of interest to demonstrate the effect on this component, or the effect on viral or replicon replication. An exemplary cell-based in vitro assay for this purpose is disclosed in PCT International Publication WO 02/18369. Alternatively, the screening can be performed by adding the test agent to in vitro translation reactions and then proceeding with the established analysis. As another alternative, purified or partially purified components which have been determined to interact with one another by the methods described above can be placed under conditions in which the interaction between them would normally occur, with and without the addition of the candidate compound, and the procedures previously established to analyze the interaction can be used to assess the impact of the candidate compound. However their anti-HCV activity is initially assayed, peptide or other inhibitors of the present invention should cause inhibition of infection, replication, or pathogenesis of Hepatitis C Virus in vitro or in vivo when introduced into a host cell containing the virus, and exhibit an $IC_{50}$ in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 mM to 25 µM, more preferably from about 0.0001 nM to 10 µM, and even more preferably from about 0.0001 nM to 1 µM.

In another embodiment of the invention, the method of screening may be by phage display. A method of obtaining selective ligands that bind a chosen target is to select from a library of proteins or peptides displayed on phage. In order to obtain a novel binding protein against a chosen target, such as an amphipathic helix region of an HCV component, DNA molecules, each encoding a protein or peptide fragment thereof, and a structural signal calling for the display of the protein on the outer surface of a chosen genetic package (bacterial cell, bacterial spore or phage) are introduced into a genetic package. The protein is expressed and the potential binding domain is displayed on the outer surface of the package. The package is then exposed to the target. If the genetic package binds to the target, then it is confirmed that the corresponding binding domain is indeed displayed by the genetic package. Packages which display the binding domain (and thereby bind the target) are separated from those which do not. For example, in the present invention, the target may be the amphipathic helix or a mutated amphipathic helix. Potential peptides, which may then be used as anti-HCV agents, are screened by determination of which will bind to the amphipathic helix or a mutated amphipathic helix. Preferred peptides are those that not only bind to the amphipathic helix, but in addition, block or inhibit the amphipathic helix from binding to its receptor or binding site, thereby inhibiting infectivity. Examples of peptides identified by phage display are set forth in Table 3.

TABLE 3

Peptides identified by phage display as ligands of the amphipathic helix of NS5A:

| Sequence | Sequence Identification Number |
|---|---|
| HDSFANATGRFWP | SEQ ID NO: 454 |
| QGTSPSRLAVPLA | SEQ ID NO: 455 |
| ISSKTGMSSEPPS | SEQ ID NO: 456 |
| ILSSIDALGSDSH | SEQ ID NO: 457 |
| LDDRSVPTVISQR | SEQ ID NO: 458 |
| YPSKPGNVTPKAP | SEQ ID NO: 459 |
| QAQGERALK | SEQ ID NO: 460 |
| TDKRASPLTVQAR | SEQ ID NO: 461 |

In all of the embodiments of the invention, the active agent which will interact, generally, either with the sites on the cytoplasmic membrane to which the amphipathic helix binds or will interact with the amphipathic helix itself, may be derivatized or coupled to additional components. By "derivatives" of these agents is meant modifications thereof that do not interfere with their ability to interact with the sites or the helix, but may optionally confer some additional useful property. One particularly useful property is the ability to penetrate cell membranes, and preferred among the derivatives or conjugated forms are those coupled to such facilitators. An additional desired coupled component may be a labeling component such as a fluorescent dye, an enzyme, or a radioisotope. One particularly useful label is, for example, green fluorescent protein in any of its many colors and forms. Green fluorescent protein thus, includes, not only forms of this fluorescent protein that fluoresce green, but also those that fluoresce various other colors such as red and blue. These forms of the protein are commercially available as are recombinant materials for their production.

The compositions of the invention can be administered as conventional HCV therapeutics. The compositions of the invention may include more than one ingredient which interrupts the binding of the amphipathic helix to the membranes and more than one peptide of the invention.

The precise formulations and modes of administration of the anti-HCV compositions of the invention will depend on the nature of the anti-HCV agent, the condition of the subject, and the judgment of the practitioner. Design of such administration and formulation is routine optimization generally carried out without difficulty by the practitioner.

In addition to the assay methods, methods to identify compounds or protocols against HCV infection, and methods to treat HCV infections as set forth above, the invention provides compositions which are effective to elicit immunological responses to HCV in appropriate subjects, such as humans or other animals subject to HCV infection.

Administration may be performed using conventional methods, typically by injection. The elicited immunological response is helpful in general HCV prophylaxis.

The following examples are intended to illustrate but not to limit the invention.

EXAMPLES

Example 1

Effect of Helix Disruption on Membrane Association

Figure 3B:
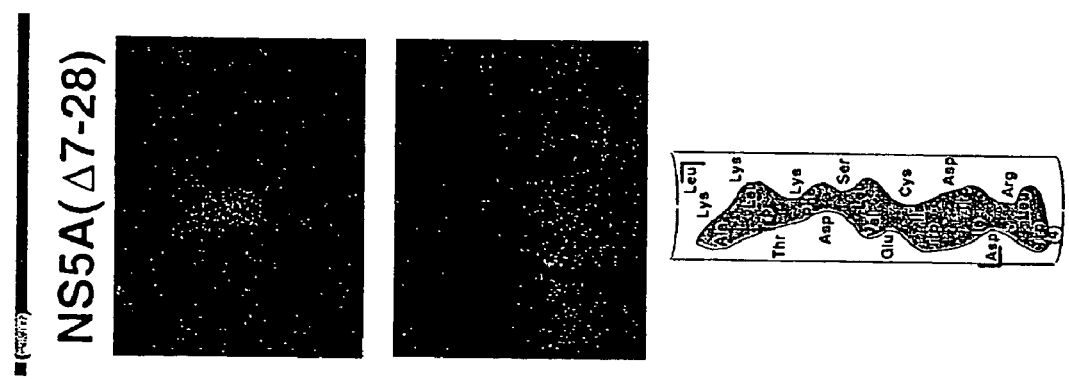
Figure 3C:
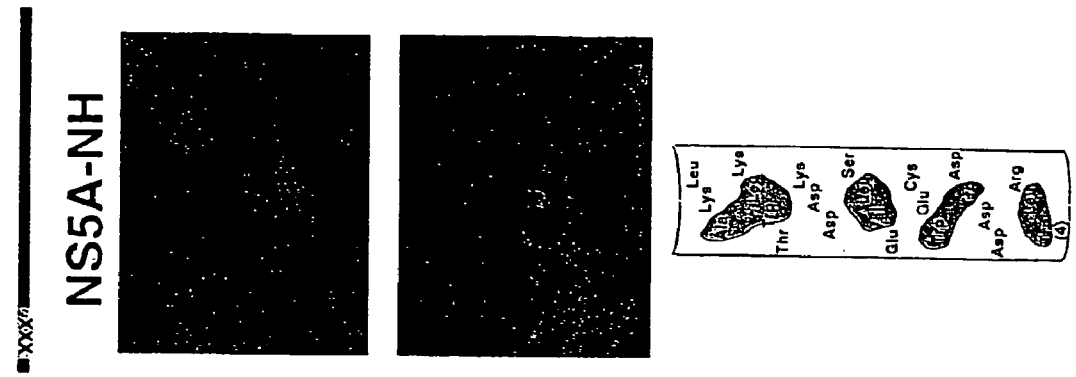

The bottom panels of FIGS. 3A-3C show the structures of the relevant portion of NS5A used in this example. FIG. 3A shows the amino acid sequence and helix formed at positions 4-27 in the NS5A protein of Hepatitis C virus genotype 1a. FIG. 3B shows the deletion of positions 7-27, thus deleting the helix, as shown by the brackets. This deletion was conducted by PCR mutagenesis essentially as described by Glenn, J. S., et al., *J. Virol* (1998) 72:9303-9306 on plasmid pBRTM/HCV 827-3011 which encodes the HCV nonstructural proteins as described by Grakoui, A., et al., *J. Virol.* (1993) 67:1385-1395. This vector encodes the NS proteins under the T7 promoter and encephalomyocarditis internal ribosome entry site control elements and directs the synthesis and processing of proteins NS3, NS4A, NS4B, NS5A and NS5B. FIG. 3C shows a mutant which was obtained using PCR mutagenesis as described above using a primer (5'-TCCGGCTCCTGGCTAAGGGACGACTGGGA- (SEQ ID NO: 452)

CTGGGAATGCGAGGTGCTGAGCGACGATAAGAC-

C-3')

in which codons isoleucine-8, isoleucine-12, and phenylalanine-19 of NS5A were changed to encode aspartate, glutamate, and aspartate, respectively. This results in disruption of the hydrophobic region of the helix.

Each of these plasmids was expressed and distribution of the NS5A protein, which is produced by the plasmids in cells, was observed. A liver derived cell line, Huh-7, was first infected with recombinant vaccinia virus encoding T7-RNA polymerase and then transfected with pBRTM/HCV 827-3001, or by this plasmid modified as described in FIGS. 3B and 3C.

After incubation to effect protein production, the cells were fixed with formaldehyde and immunostained with a monoclonal antibody against NS5A and a Texas Red-labeled donkey anti-mouse secondary antibody essentially as described by Glenn, J. S., et al., *J. Virol.* (1990) 64:3104-3107. As shown in the upper panel of FIG. 3A, perinuclear punctuate vesicular staining suggestive of a Golgi-like intracellular distribution pattern was readily observed, as was, occasionally, a somewhat reticulin chicken-wire-like staining pattern, characteristic of the ER Both patterns have been reported previously when NS5A is expressed either alone or in combination with other HCV NS proteins using a variety of expression systems. See, for example, Kim, J. E., et al., *Arch. Virol.* (1999) 144:329-343; Huang, Y., et al., *Biochem. Biophys. Res. Commun.* (2001) 281:732-740.

However, when the construct of FIG. 3B, containing a deleted portion of NS5A was expressed, as shown in the upper panel of FIG. 3B, cytoplasmic membrane localization was abolished and a nuclear localization pattern was obtained. A cryptic nuclear localization signal in the NS5A C-terminal domain has previously been reported by Ide, Y., et al., *Gene* (1996) 182:203-211.

When the construct described in FIG. 3C, which disrupts the hydrophobic face of the helix, is expressed in these cells, again, as shown in the upper panel of FIG. 3C, the cytoplasmic membrane localization pattern was lost and localization to the nucleus was observed.

FIGS. 3A-3C show these results at two magnification levels. The uppermost panel in each case shows results for a single cell and the intermediate panel shows results for a number of cells. As shown in the intermediate panels in FIGS. 3B and 3C, occasionally distribution of the dye throughout the cell was observed rather than localization to the nucleus. However, even in these cases, no specific localization to the cytoplasmic membrane could be detected.

Example 2

Intracellular Location of GFP-Labeled Helix

Three constructs were made. First, as a control, the HCV encoding sequences of pBRTM/HCV 827-3011 were replaced with the coding sequence for jellyfish *Aequorea Victoria* green fluorescent protein (GFP) using a PCR cloned insert from plasmid C109 which contains E-GFP (Clontech), to obtain "T7-GFP." A fragment of the NS5A gene encoding the amphipathic helix was fused into frame with the sequence encoding the N-terminus of GFP in T7-GFP by creating a common PstI site using PCR mutagenesis. This permits junction of the first 31 amino acids of NS5A to the 5' side of serine-2 of the GFP-encoding sequence in T7-GFP. The resulting vector was labeled "T7-5AGFP." A similar vector, designated "T7-5ANHGFP" was constructed in a manner similar to "T7-5AGFP" except that the corresponding segment from the mutated form of NS5A set forth in FIG. 3C was employed in place of the wildtype helix. Thus, "T7-5ANHGFP" is similar to "T7-5AGFP" except that in the NS5A helix, Ile at position 8 is converted to Asp, Ile at position 12 is converted to Glu, and Phe at position 19 is converted to Asp.

Figure 4C:
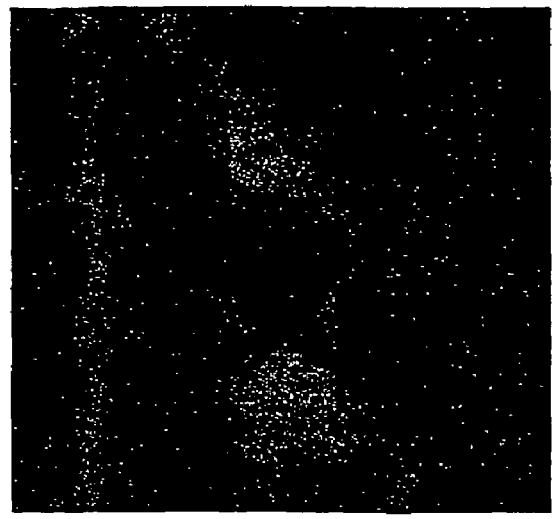
FIGS. 4A-4C show the distribution patterns of the N-terminal amphipathic helix of NS5A coupled to green fluorescent protein (GFP) in comparison to suitable controls.
Figure 4B:
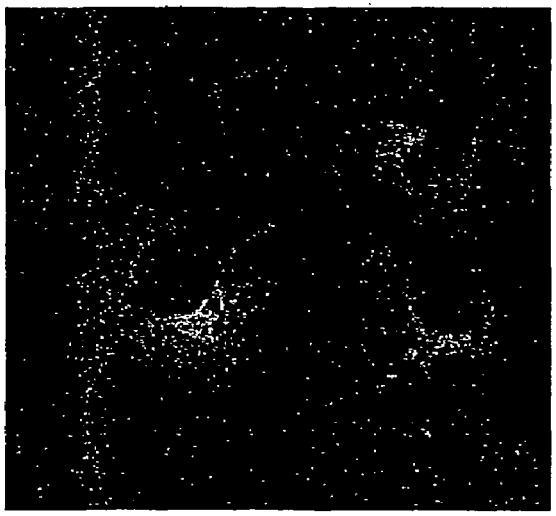
Figure 4A:
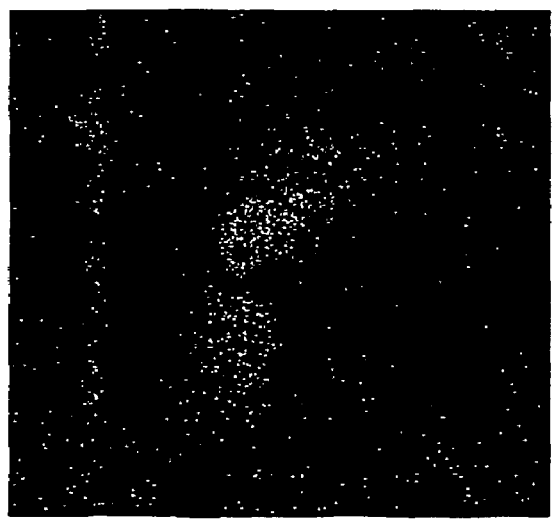

These constructs were used to effect expression of GFP or of the GFP fusions in Huh-7 cells as described in Example 1 and the distribution of fluorescence was evaluated with the results as shown in FIGS. 4A-4C. As shown in FIG. 4A, cells expressing GFP alone show a wide diffuse pattern including concentration in the nucleus. Cells expressing 5AGFP show distribution of fluorescence similar to that of the NS5A protein itself with a Golgi-like intracellular distribution pattern and ER staining. Cells expressing 5ANH-GFP failed to show this pattern but instead mimic the distribution pattern of GFP.

Example 3

Effect of Helix Disruption on HCV RNA Replication

Comparative high efficiency, second generation, bicistronic, subgenomic RNA replicons of HCV described by Blight, K. J., et al., *Science* (2001) 290:1972-1974 were constructed with a neomycin-resistance gene. Similar constructs were made with wildtype NS5A and with NS5A altered in the amphipathic helix as described in Examples 1 and 2. Diagrams of these constructs are shown in the upper panels of FIGS. 5A and 5B.

The construct containing the wildtype NS5A, Bart79I, was made by PCR mutagenesis of HCVrep1bBartMan/AvaII (Blight, supra) such that nucleotide 5336 was changed from a G to T resulting in a change in NS5A codon 1179 from serine to isoleucine. This mutation results in a dramatic increase in replication efficiency of the HCV subgenomic replicon. Bart5X79I (containing the modified helix) was made by PCR mutagenesis of Bart79I using a primer (5'-G<u>A</u>TTGGGATTGG<u>GA</u>ATGCACGGTGTTGACT (SEQ ID NO: 453) GAT<u>GA</u>CAAGACCTGG-3')

in which codons valine-8, isoleucine-12, and phenylalanine-19 of NS5A were changed to encode aspartate, glutamate, and aspartate, respectively. All mutations were confirmed by DNA sequencing.

The RNA replication efficiency was then assayed by ability to establish G418-resistant colonies after transfection of Huh-7 cells as follows: Replicon RNA's were prepared by in vitro transcription with T7-RNA polymerase of ScaI-linearized plasmids (Bart79I or Bart5X79I) followed by DNase treatment and purification. Replicons were then electroporated into Huh-7 cells and neomycin-resistant colonies selected by inclusion of 1 mg/ml G418 in the culture media. Methods were essentially as described by Blight (supra). Colonies were detected by staining with cresyl violet. Multiple independent preparations of replicons and replication assays yielded similar results.

Figure 5A:
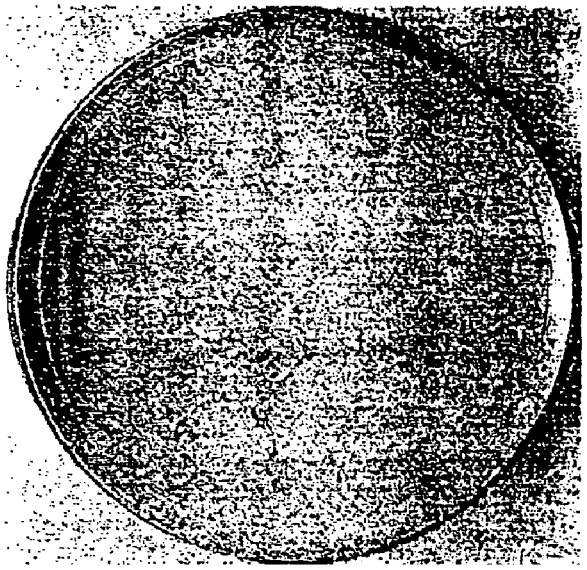
FIGS. 5A and 5B, upper panels, show schematics of subgenomic replicons of HCV used in HCV replication assays.
Figure 5B:
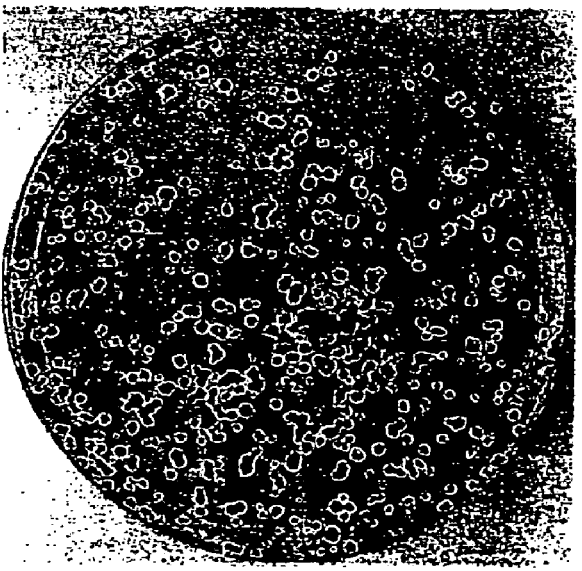

As shown in FIG. 5A, lower panel, the replicon with wildtype NS5A N-terminus gave rise to numerous colonies while disrupting the amphipathic nature of the N-terminal helix results in a dramatic inhibition of HCV genome replication as shown in the lower panel of FIG. 5B.

There was no decreased transfection efficiency or any decrease in the ability to establish colonies when control experiments using plasmids encoding drug resistance marker along with only the wildtype or mutant NS5A proteins were used in place of the replicons above, thus establishing that the results were not due to an increased cytotoxicity associated with mutant NS5A.

Example 4

Floatation Assay

In this membrane floatation assay, the ability of the NS5A amphipathic helix to bind to a preparation of microsomal membranes was tested. NS5A proteins, both the NS5A wildtype or mutant amphipathic helix (described in Example 1), were in vitro translated and [$^{35}$S]-labeled using the Promega TNT reticulocyte lysate kit. Plasmids pC5A or pC5ANH were used as transcription templates. Aliquots of the reactions were combined with a membrane fraction derived from Huh-7 cells, with or without synthetic peptides, and overlayed with a 5-40% OptiPrep step gradient. After centrifugation for 4 hrs at 40,000 xg in a SW60 rotor, 500 ml fractions were collected from the top and the proteins in each gradient fraction were precipitated and analyzed by SDS-PAGE. The percentage of protein "floating" to the top of the gradient with membranes (fraction 2 from the top) was then quantified using a Molecular Dynamics phosphorimager.

FIGS. 6A and 6B show a comparison of the results for wildtype and mutant forms. The numbers correspond to Optiprep gradient (5-40%) fraction number. Non-membrane associated proteins remain at the bottom (right side) of the gradient, whereas membranes—and associated proteins— "float" towards less dense gradient fractions present at the top (left side). As shown, in the reaction mixture containing wildtype, the synthesized NS5A floated toward the top of the gradient coupled with the membrane. This was not found in the case of the mutant form. In both cases, there was a degree of non-specific binding associated with fractions that settle to the bottom of the gradient. An advantage of this method is elimination of the artifacts caused by non-specific binding, as illustrated by the labeling of high density fractions in both mixtures.

FIG. 6C shows the percentage of NS5A wildtype or mutant protein that float with the membrane fractions as a percentage of the total synthesized. As seen, 25% of the wildtype, but only 0.8% of the mutant, was associated with the membrane.

Figure 7A:
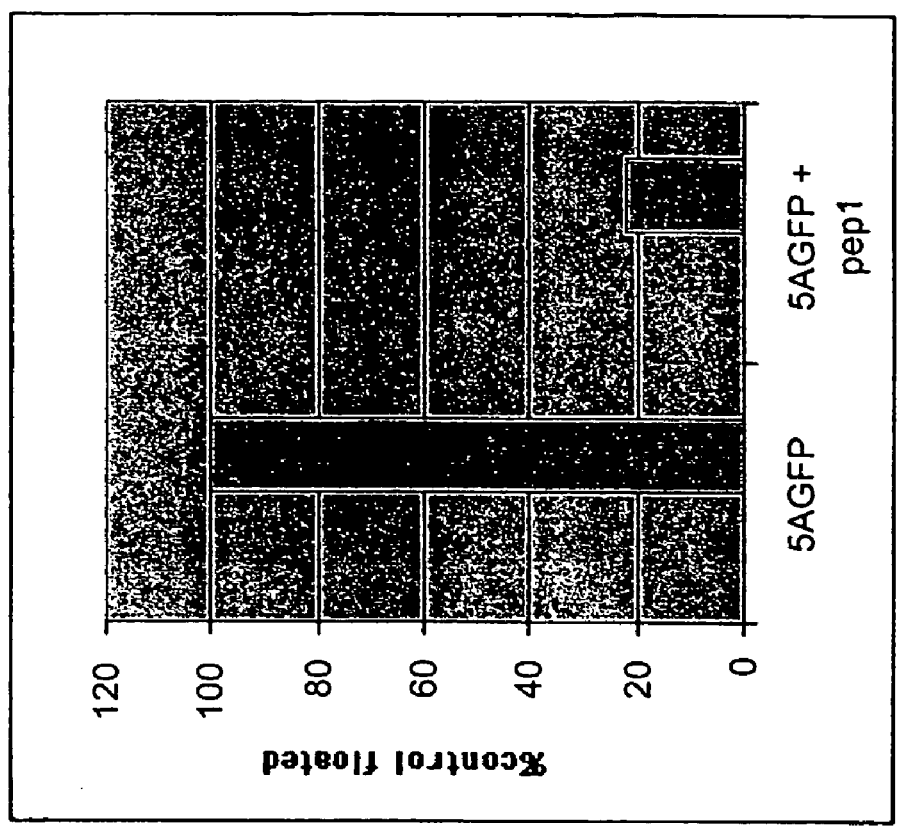
FIGS. 7A and 7B show the effects of a peptide useful as an anti-HCV agent on binding of NS5A to the microsomal membrane using a floatation assay.
Figure 7B:
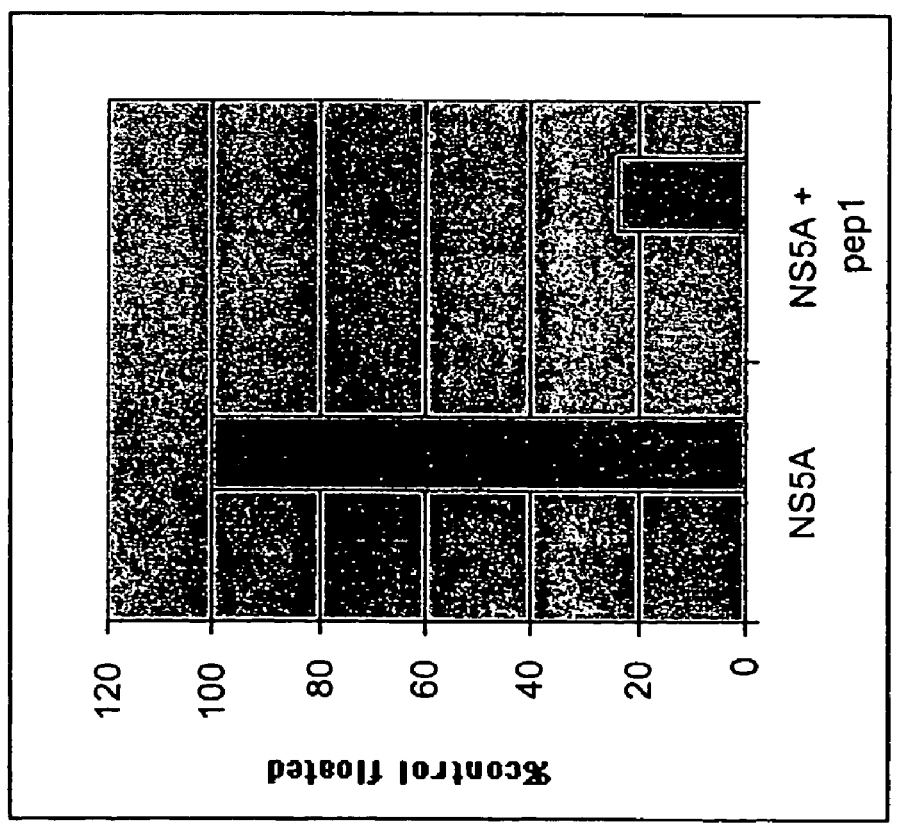

FIGS. 7A and 7B show the results of a similar floatation experiment in the presence and absence of a test peptide that is a competitive inhibitor of the NS5A helix. This peptide contains amino acids 1-27 of NS5A with a C-terminal "flag" DYKD. The assay described in the preceding paragraph was repeated in the presence and absence of this peptide. As shown in FIG. 7A, the percentage of NS5A floated in the absence of peptide is arbitrarily normalized to 100%; in comparison with this, the presence of the test peptide lowered the percentage to about 21%.

Similarly, the assay was modified by using, in place of NS5A, a fusion protein consisting of the amphipathic helix of NS5A with green fluorescent protein. As can be seen in FIG. 7B, the amount of labeled NS5A floated with the membrane was set in the absence of test peptide at 100%. In comparison, the presence of the test peptide lowered the percentage floated to about 21%.

Moreover, as shown in FIG. 6C, a synthetic peptide designed to mimic the wild type AH not only competitively inhibited membrane association of NS5A, but did so in a dose-dependent manner. The maximal extent of inhibition achieved pharmacologically was comparable to that obtained by genetic mutation of the AH. In addition, the synthetic peptide appears equally effective against NS5A derived from different genotypes (data not shown), including those most refractory to current therapies. This convenient membrane floatation assay has also proven well-suited for current efforts focused on studying the mechanistic details of the AH membrane-targeting domain, and ideal for guiding ongoing development of peptidomimetic compounds designed to resemble key elements, or bind to specific features, of the AH. Such compounds represent an exciting potential addition to current anti-HCV combination therapy regimens.

Figure 8:
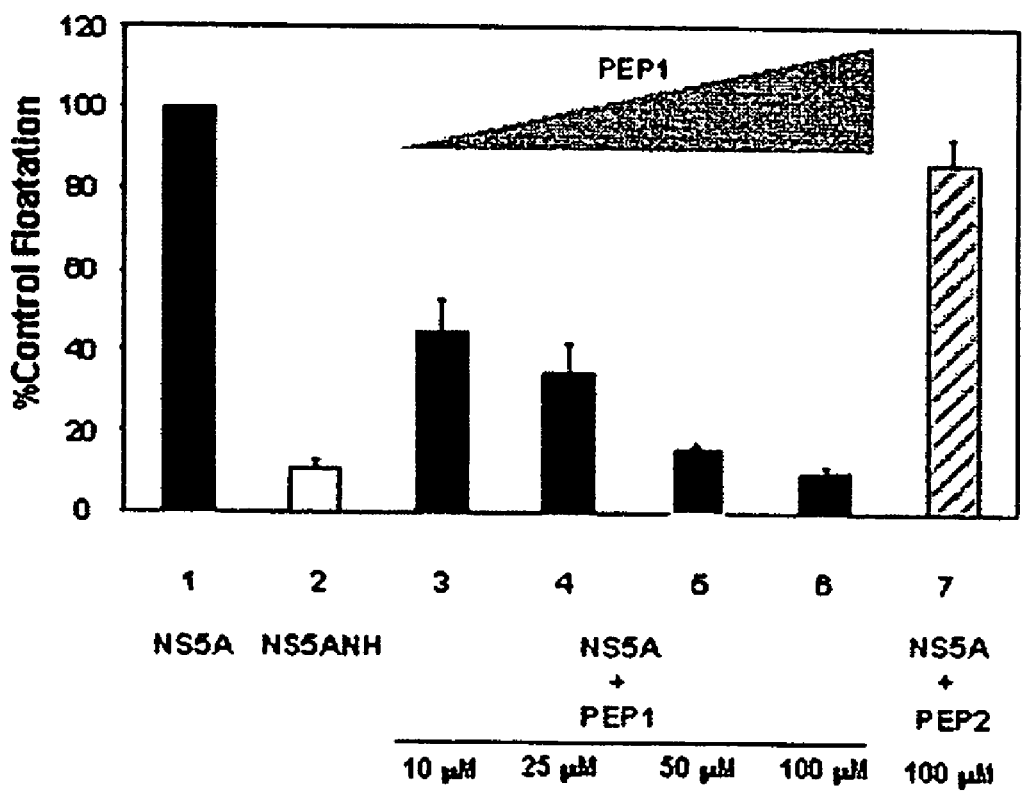
FIG. 8 shows pharmacologic inhibition of NS5A membrane association.

FIG. 8 shows Pharmacologic inhibition of NS5A membrane association. Huh-7 cells-derived membranes were treated with PEP1 (a peptide mimicking the wild type amphipathic helix of NS5A), PEP2 (a control peptide) or mock-treated with water. PEP1 (a peptide that corresponds to the wild type N-terminal amphipathic helix of NS5A (amino acids 1-26) with a C-terminal FLAG tag) and PEP2 (which is identical to PEP1 except amino acids isoleucine-8, isoleucine-12, and phenylalanine-19 of NS5A were changed to aspartate, glutamate, and aspartate, respectively) were synthesized by AnaSpec Inc. In-vitro translated NS5A (or NS5ANH) was incubated with membranes and various concentrations of peptides or water prior to analysis by membrane floatation assays set forth above. The amount of NS5A floating with no peptide treatment typically is ~30% of the total iii-vitro translated NS5A. For comparison between treatment conditions, results were normalized to the no-treatment control. The percent of NS5A (or NS5ANH) floating with the membranes under the indicated conditions was determined as in FIG. 6A and expressed relative to mock-treated control. Error bars represent standard error of the mean.

While the invention has been described in detail with reference to certain preferred embodiments thereof, it will be understood that modifications and variations are within the spirit and scope of that which is described and claimed.

REFERENCES

1. Araga S, Blalock J E. Use of complementary peptides and their antibodies in B-cell-mediated autoimmune disease: prevention of experimental autoimmune myasthenia gravis with a peptide vaccine. Immunomethods. 1994 October; 5(2):130-5.
2. Araga S, Galin F S, Kishimoto M, Adachi A, Blalock J B. Prevention of experimental autoimmune myasthenia gravis by a monoclonal antibody to a complementary peptide for the main immunogenic region of the acetylcholine receptors. J. Immunol. 1996 Jul. 1; 157(1):386-92.
3. Araga S, LeBoeuf R D, Blalock J E. Prevention of experimental autoimmune myasthenia gravis by manipulation of the immune network with a complementary peptide for the acetylcholine receptor. Proc Natl Acad Sci U.S.A. 1993 Sep. 15; 90(18):8747-51.
4. Blalock J E, Bost K L. Binding of peptides that are specified by complementary RNAs. Biochem J. 1986 Mar. 15; 234(3):679-83.
5. Blalock J E, Whitaker J N, Benveniste E N, Bost K L. Use of peptides encoded by complementary RNA for generating anti-idiotypic antibodies of predefined specificity. Methods Enzymol. 1989; 178:63-74.
6. Bost K L, Blalock J E. Complementary peptides as interactive sites for protein binding. Viral Immunol. 1989 Winter; 2(4):229-38.
7. Bost K L, Blalock J E. Preparation and use of complementary peptides. Methods Enzymol. 1989; 168:16-28.
8. Bost K L, Blalock J E. Production of anti-idiotypic antibodies by immunization with a pair of complementary peptides. J Mol. Recogrit. 1989 April; 1(4):179-83.
9. Bost K L, Smith E M, Blalock J E. Similarity between the corticotropin (ACTH) receptor and a peptide encoded by an RNA that is complementary to ACTH mRNA. Proc Natl Acad Sci USA. 1985 March; 82(5):1372-5.
10. Hawiger, J., *Noninvasive intracellular delivery of functional peptides and proteins.* Current Opinion in Chemical Biology, 1999. 3: p. 89-94.
11. Holsworth D D, Kiely J S, Root-Bernstein R S, Overhiser R W. Antisense-designed peptides: a comparative study focusing on possible complements to angiotensin II. Pept Res. 1994 Jul-Aug; 7(4):185-93.
12. Kolykhalov, A. A. and Rice, C. M. (Science 277 (5325), 570-574 (1997).
13. Maria Lindgren, M. H., Alain Prochiantz, and Ulo Langel, *Cell-penetrating peptides.* Trends in Pharmacological Sciences, 2000. 21: p. 99-103.
14. May C. Morris, J. D., Jean Mery, Frederic Heitz and Gilles Divita, *A peptide carrier for the delivery of biologically active proteins into mammalian cells.* Nature Biotechnology, 2001. 19: p. 1173-1176.
15. Pfister R R, Haddox J L, Blalock J E, Sommers C I, Coplan L, Villain M. Synthetic complementary peptides inhibit a neutrophil chemoattractant found in the alkali-injured cornea. Cornea. 2000 May; 19(3):384-9.
16. Mauricio Rojas, J. P. D., Zhongjia Tan, and Yao-Zhong Lin, *Genetic engineering of proteins with cell membrane permeability.* Nature Biotechnology, 1998. 16: p. 370-375.
17. Anne Scheller, B. W., Matthias Meizig, Michael Bienert, and Johannes Oehlke, *Evidence for an amphipathicity independent cellular uptake of amphipathic cell-penetrating peptides.* European Journal of Biochemistry, 2000. 267: p. 6043-6049.
18. Swords B H, Carr D J, Blalock J E, Berecek K H. An antibody directed against a peptide encoded by RNA complementary to mRNA for vasopressin recognizes putative vasopressin receptors. Neuroendocrinology. 1990 April; 51(4):487-92.
19. Weigent D A, Clarke B L, Blalock J E. Peptide design using a genetically patterned binary code: growth hormone-releasing hormone as a model. Immunomethods. 1994 October; 5(2):91-7.
20. Xue Yan Liu, D. R., Ruth Ann Veach, Danya Liu, Sheila Timmons, Robert D. Collins, and Jacek Hawiger, *Peptide-directed suppression of a pro-inflammatory cytokine response.* The Journal of Biological Chemistry, 2000. 275: p. 16774-16778.
21. Yunfeng Zhao, D. L., John Burkett, Heinz Kohler, *Chemical engineering of cell penetrating antibodies.* Journal of Immunological Methods, 2001. 254: p. 137-145.
22. Lianshan Zhang, T. R. T., Xue-Yan Liu, Sheila Timmons, Ann D. Colosia, Jacek Hawiger and James P. Tam, *Preparation of functionally active cell-permeable peptides by single-step ligation of two peptide modules.* Proc. Natl. Acad. Sci. USA, 1998. 95: p. 9184-9189.
23. Badkar, A., Talluri, K., Tenjarla, S., Jaynes, J., Banga, A., *In Vitro Release Testing of a Peptide Gel.* Pharm. Technol., 44-52 (January 2000).
24. Bernkop-Schnurch, A. *Chitosan and its derivatives: potential excipients for peroral peptide delivery systems.* Int. J. Pharm. 194, 1-13 (2000).
25. Gonda, I., *The Ascent of Pulmonary Drug Delivery.* J. Pharm. Sci. 89, 940-945 (2000).
26. Jung, T. Kamm, W., Breitenbach, A., Kaiserling, E., Xiao, J. X., Kissel, T., *Biodegradable nanoparticles for oral delivery of peptides: is there a role for polymers to affect mucosal uptake?* Eur. J. Pharm. Biopharm. 50, 147-160 (2000).
27. Latham, P., *Therapeutic Peptides Revisited.* Nat. Biotech. 17, 755-757 (1999).
28. Pillai, O., Nair, V., Poduri, R., Pancchagnula, R., *Transdermal Iontophoresis. Part II: Peptide and Protein Delivery.* Methods Find. Exp. Clin. Pharmacol. 21(3): 229-240 (1999).
29. Sakuma, S. Hayashi, M., Akashi, M., *Design of nanoparticles composed of graft copolymers for oral peptide delivery.* Advanced Drug Delivery Reviews 47, 21-37 (2001).
30. Takeuchi, H., Yamamoto, H., Kawashima, Y. *Mucoadhesive nanoparticulate systeme for peptide drug delivery.* Advanced Drug Delivery Reviews 47, 39-51 (2001).
31. Veronese, F. M., Morpugo, M., Bioconjugation in pharmaceutical chemistry. II Farmaco 54, 497-516 (1999).
32. Veuillex, F., Kalia, Y. N., Jacques, Y., Dashusses, J., Buri, P., *Factors and strategies for improving buccal absorption of peptides.* Eur. J. Pharm. Biopharm. 51, 93-109 (2001).
33. Wang, W., Jiang, J., Ballard, C. E., Wang, B., *Prodrug Approaches to the Improved Delivery of Peptide Drugs.* Cur. Pharm. Des. 5, 265-287 (1999).

What is claimed is:

1. A method for assessing activity of a candidate compound in interfering with binding of a Hepatitis C virus (HCV) nonstructural protein with a eukaryotic cell cytoplasmic membrane, comprising:
assessing, in the presence and absence of a candidate compound, binding of a polypeptide comprising an amphipathic helix of an N-terminal region of an HCV nonstructural protein with cytoplasmic membranes of a eukaryotic cell, wherein the non-structural protein is NS4B or NS5A;
wherein reduced binding in the presence of the candidate compound relative to a level of binding in the absence of the candidate compound indicates activity of the candidate compound in interfering with binding of HCV nonstructural protein to the cytoplasmic membranes.

2. The method of claim 1, wherein the assessing is performed extracellularly.

3. The method of claim 2, wherein the assessing comprises determining the ability of a compound to bind to the amphipathic helix.

4. The method of claim 2, wherein the cytoplasmic membranes are a cell membrane preparation, and wherein said assessing comprises determining the binding of the amphipathic helix to the cell membrane preparation in the presence of a candidate compound and in the absence of a candidate compound, wherein a decrease in the binding of the amphipathic helix to the cell membrane preparation in the presence of the compound as compared to binding in the absence of the compound identifies the compound as interfering with binding of the amphipathic helix to the cytoplasmic membranes of the eukaryotic cell.

5. The method of claim 1, wherein the method is performed intracellularly in a eukaryotic cell.

6. The method of claim 5, wherein the amphipathic helix is coupled to a detectable label and the intracellular distribution of the label is assessed in the presence of a candidate compound, wherein the candidate compound is identified as interfering with binding of the HCV nonstructural protein to a eukaryotic cytoplasmic membrane when its presence results in an intracellular distribution of the label which does not show binding to cytoplasmic membranes in comparison to the distribution of the label in the absence of the compound.

7. The method of claim 6, wherein the detectable label is green fluorescent protein.

8. The method of claim 1, wherein the eukaryotic cell is a mammalian cell.

9. The method of claim 1, wherein the non-structural protein is NS4B.

10. The method of claim 1, wherein the non-structural protein is NS5A.

11. The method of claim 1, wherein the candidate compound is a peptide.

12. A method of identifying a peptide that inhibits the binding of an HCV nonstructural protein to a cytoplasmic membrane of a eukaryotic cell, comprising contacting a polypeptide comprising an amphipathic helix of an N-terminal region of an HCV nonstructural protein with cytoplasmic membranes of a eukaryotic cell in the presence and absence of a test peptide, wherein the non-structural protein is NS5A; and assessing binding of the amphipathic helix of the polypeptide to the cytoplasmic membranes;

wherein a decreased level of binding of the amphipathic helix to the cytoplasmic membrane in the presence of the test peptide as compared to a level of binding of the amphipathic helix to the cytoplasmic membrane in the absence of the test peptide indicates the test peptide inhibits the binding of an HCV nonstructural protein to a cytoplasmic membrane of a eukaryotic cell.

13. The method of claim 12, wherein the peptide has the amino acid sequence as set forth in one of SEQ ID NOs:1-16.

14. The method of claim 12, wherein the eukaryotic cell is a mammalian cell.

15. The method of claim 12, wherein the polypeptide comprises a detectable label.

16. The method of claim 15, wherein the detectable label is a fluorescent label or a radioisotope.

17. The method of claim 16, wherein the fluorescent label is a green fluorescent protein.

* * * * *